US011155544B2

(12) United States Patent
Goldstein et al.

(10) Patent No.: US 11,155,544 B2
(45) Date of Patent: Oct. 26, 2021

(54) HETEROCYCLE COMPRISING TYROSINE KINASE INHIBITORS

(71) Applicant: Principia Biopharma Inc., South San Francisco, CA (US)

(72) Inventors: David M. Goldstein, Redwood City, CA (US); Timothy D. Owens, Redwood City, CA (US)

(73) Assignee: Principia Biopharma Inc., South San Francisco, CA (US)

( * ) Notice: Subject to any disclaimer, the term of this patent is extended or adjusted under 35 U.S.C. 154(b) by 0 days.

(21) Appl. No.: 16/523,979

(22) Filed: Jul. 26, 2019

(65) Prior Publication Data

US 2019/0345159 A1    Nov. 14, 2019

Related U.S. Application Data

(63) Continuation of application No. 15/738,051, filed as application No. PCT/US2016/039070 on Jun. 23, 2016, now abandoned.

(60) Provisional application No. 62/183,969, filed on Jun. 24, 2015, provisional application No. 62/271,715, filed on Dec. 28, 2015.

(51) Int. Cl.
*C07D 471/04* (2006.01)
*C07D 487/04* (2006.01)
*A61P 19/02* (2006.01)

(52) U.S. Cl.
CPC ............ *C07D 471/04* (2013.01); *A61P 19/02* (2018.01); *C07D 487/04* (2013.01)

(58) Field of Classification Search
CPC .......................... C07D 471/04; C07D 487/04
See application file for complete search history.

(56) References Cited

U.S. PATENT DOCUMENTS

| | | | |
|---|---|---|---|
| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1 | 3/2014 | Goldstein |
| 8,759,358 B1 | 6/2014 | Goldstein |
| 8,828,426 B2 | 9/2014 | Shah et al. |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens et al. |
| 9,994,576 B2 | 6/2018 | Owens et al. |
| 10,092,569 B2 | 10/2018 | Masjedizadeh et al. |
| 10,456,403 B2 | 10/2019 | Masjedizadeh et al. |
| 10,485,797 B2 | 11/2019 | Gourlay |
| 10,533,013 B2 | 1/2020 | Owens et al. |
| 2003/0153752 A1 | 8/2003 | Hirst et al. |
| 2003/0187001 A1 | 10/2003 | Calderwood et al. |
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |
| 2006/0079494 A1 | 4/2006 | Santi et al. |
| 2006/0275376 A1 | 12/2006 | Guimberteau et al. |
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |

(Continued)

FOREIGN PATENT DOCUMENTS

| | | |
|---|---|---|
| CN | 1274280 A | 11/2000 |
| CN | 1681483 A | 10/2005 |

(Continued)

OTHER PUBLICATIONS

2012 ICD-9-CM Diagnosis Code 372.30: Conjunctivitis, unspecified, retrieved Aug. 4, 2016 (1 page).

(Continued)

*Primary Examiner* — Valerie Rodriguez-Garcia
(74) *Attorney, Agent, or Firm* — McNeill Baur PLLC

(57) ABSTRACT

The present disclosure provides compounds of formula (I) that are tyrosine kinase inhibitors, in particular Bruton tyrosine kinase ("BTK") inhibitors, and are therefore useful for the treatment of diseases treatable by inhibition of BTK such as cancer, autoimmune, inflammatory, and thromboembolic diseases. Also provided are pharmaceutical compositions containing such compounds and processes for preparing such compounds.

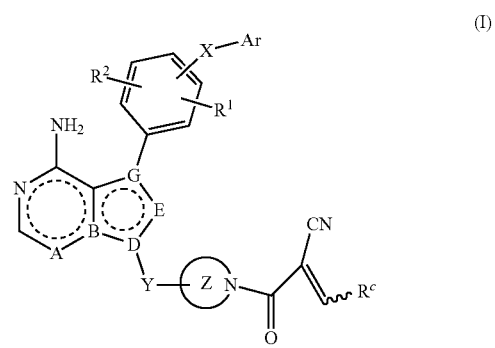

(I)

4 Claims, No Drawings

(56) References Cited

U.S. PATENT DOCUMENTS

| | | |
|---|---|---|
| 2008/0076921 A1 | 3/2008 | Honigberg et al. |
| 2008/0146643 A1 | 6/2008 | Billen et al. |
| 2008/0176865 A1 | 7/2008 | Billen et al. |
| 2008/0260818 A1 | 10/2008 | Penhasi et al. |
| 2009/0215750 A1 | 8/2009 | Bamberg et al. |
| 2009/0215788 A1 | 8/2009 | Elworthy et al. |
| 2009/0306396 A1 | 12/2009 | Toyoshima et al. |
| 2010/0113520 A1 | 5/2010 | Miller |
| 2010/0144705 A1 | 6/2010 | Miller |
| 2010/0152143 A1 | 6/2010 | Priebe et al. |
| 2010/0254905 A1 | 10/2010 | Honigberg et al. |
| 2011/0021518 A1 | 1/2011 | Magnuson et al. |
| 2011/0086866 A1 | 4/2011 | Chen et al. |
| 2012/0028981 A1 | 2/2012 | Miller |
| 2012/0071497 A1 | 3/2012 | Buggy et al. |
| 2013/0079327 A1 | 3/2013 | Yamamoto et al. |
| 2013/0197014 A1 | 8/2013 | Chen et al. |
| 2014/0094459 A1* | 4/2014 | Goldstein ............... A61P 19/02 514/234.2 |
| 2014/0142099 A1 | 5/2014 | Owens |
| 2014/0221398 A1 | 8/2014 | Goldstein et al. |
| 2014/0256734 A1 | 9/2014 | Lawson et al. |
| 2014/0303190 A1 | 10/2014 | Goldstein |
| 2014/0364410 A1 | 12/2014 | Owens et al. |
| 2015/0140085 A1 | 5/2015 | Goldstein |
| 2015/0353557 A1 | 12/2015 | Goldstein et al. |
| 2015/0353562 A1 | 12/2015 | Goldstein |
| 2016/0045503 A1 | 2/2016 | Goldstein et al. |
| 2016/0257686 A1 | 9/2016 | Owens |
| 2016/0376277 A1* | 12/2016 | Desai ................. A61P 37/06 514/210.16 |
| 2018/0015088 A1 | 1/2018 | Nunn et al. |
| 2018/0162861 A1 | 6/2018 | Goldstein et al. |
| 2018/0193274 A1 | 7/2018 | Nunn et al. |
| 2018/0305350 A1 | 10/2018 | Goldstein et al. |
| 2019/0231784 A1 | 8/2019 | Ferdous et al. |
| 2020/0038405 A1 | 2/2020 | Masjedizadeh et al. |
| 2020/0101059 A1 | 4/2020 | Gourlay et al. |
| 2020/0190092 A1 | 6/2020 | Owens et al. |

FOREIGN PATENT DOCUMENTS

| | | |
|---|---|---|
| CN | 1874761 A | 12/2006 |
| CN | 101610676 A | 12/2009 |
| CN | 101730699 A | 6/2010 |
| CN | 101805341 A | 8/2010 |
| CN | 101880243 A | 11/2010 |
| CN | 102159214 A | 8/2011 |
| CN | 103096716 A | 5/2013 |
| CN | 103534258 A | 1/2014 |
| CN | 104640861 A | 5/2015 |
| CN | 105753863 A | 7/2016 |
| EP | 0461546 A2 | 12/1991 |
| EP | 0493767 A2 | 7/1992 |
| EP | 0908457 A1 | 4/1999 |
| EP | 2443929 A1 | 4/2012 |
| EP | 2578585 A1 | 4/2013 |
| FR | 2535721 A1 | 5/1984 |
| GB | 2447933 A | 10/2008 |
| JP | 56-63950 A | 5/1981 |
| JP | 02-1450 A | 1/1990 |
| JP | 04-177244 A | 6/1992 |
| JP | 2005-239657 A | 9/2005 |
| JP | 2010-504324 A | 2/2010 |
| JP | 2010-235628 A | 10/2010 |
| JP | 2014-513729 A | 6/2014 |
| JP | 2014-517838 A | 7/2014 |
| JP | 6203848 | 9/2017 |
| WO | WO 95/24190 A2 | 9/1995 |
| WO | WO 95/31432 A1 | 11/1995 |
| WO | WO 98/41499 A1 | 9/1998 |
| WO | WO 99/14216 A1 | 3/1999 |
| WO | WO 99/18938 | 4/1999 |
| WO | WO 01/72751 A1 | 10/2001 |
| WO | WO 02/066463 A1 | 8/2002 |
| WO | WO 03/037890 A2 | 5/2003 |
| WO | WO 03/050080 A1 | 6/2003 |
| WO | WO 03/068157 A2 | 8/2003 |
| WO | WO 03/082807 A2 | 10/2003 |
| WO | WO 2004/016259 A1 | 2/2004 |
| WO | WO 2004/074283 A2 | 9/2004 |
| WO | WO 2005/020929 A2 | 3/2005 |
| WO | WO 2005/023773 A1 | 3/2005 |
| WO | WO 2005/030184 A2 | 4/2005 |
| WO | WO 2005/085210 A1 | 9/2005 |
| WO | WO 2006/086634 A2 | 8/2006 |
| WO | WO 2006/134468 A1 | 12/2006 |
| WO | WO 2007/043401 A1 | 4/2007 |
| WO | WO 2007/087068 A2 | 8/2007 |
| WO | WO 2007/130075 A1 | 11/2007 |
| WO | WO 2007/142755 A2 | 12/2007 |
| WO | WO 2008/005954 A2 | 1/2008 |
| WO | WO 2008/006032 A1 | 1/2008 |
| WO | WO 2008/039218 A2 | 4/2008 |
| WO | WO 2008/054827 A2 | 5/2008 |
| WO | WO 2008/061740 A1 | 5/2008 |
| WO | WO 2008/072053 A2 | 6/2008 |
| WO | WO 2008/072077 A2 | 6/2008 |
| WO | WO 2008/116064 A2 | 9/2008 |
| WO | WO 2008/121742 * | 10/2008 |
| WO | WO 2008/121742 A2 | 10/2008 |
| WO | WO 2009/140128 A2 | 11/2009 |
| WO | WO 2009/143477 A1 | 11/2009 |
| WO | WO2010/009342 * | 1/2010 |
| WO | WO 2010/009342 A2 | 1/2010 |
| WO | WO 2010/014930 A2 | 2/2010 |
| WO | WO 2010/065898 A2 | 6/2010 |
| WO | WO 2011/031896 A2 | 3/2011 |
| WO | WO 2011/046964 A2 | 4/2011 |
| WO | WO 2011/060440 A2 | 5/2011 |
| WO | WO 2011/144585 A1 | 11/2011 |
| WO | WO 2011/152351 A1 | 12/2011 |
| WO | WO 2011/153514 * | 12/2011 |
| WO | WO 2011/153514 A2 | 12/2011 |
| WO | WO 2012/021444 A1 | 2/2012 |
| WO | WO 2012/158764 A1 | 11/2012 |
| WO | WO 2012/158795 A1 | 11/2012 |
| WO | WO 2012/158810 A1 | 11/2012 |
| WO | WO 2012/158843 * | 11/2012 |
| WO | WO2012/158843 * | 11/2012 |
| WO | WO 2012/158843 A2 | 11/2012 |
| WO | WO 2013/003629 A2 | 1/2013 |
| WO | WO 2013/010136 A2 | 1/2013 |
| WO | WO2013/010380 * | 1/2013 |
| WO | WO 2013/010380 A1 | 1/2013 |
| WO | WO2013/010868 * | 1/2013 |
| WO | WO 2013/010868 A1 | 1/2013 |
| WO | WO 2013/010869 A1 | 1/2013 |
| WO | WO 2013/041605 A1 | 3/2013 |
| WO | WO 2013/059738 A1 | 4/2013 |
| WO | WO 2013/102059 A1 | 7/2013 |
| WO | WO 2013/116382 A1 | 8/2013 |
| WO | WO 2013/185082 A2 | 12/2013 |
| WO | WO 2013/191965 A1 | 12/2013 |
| WO | WO 2014/004707 A1 | 1/2014 |
| WO | WO 2014/022569 A1 | 2/2014 |
| WO | WO 2014/039899 * | 3/2014 |
| WO | WO 2014/039899 A1 | 3/2014 |
| WO | WO 2014/068527 A1 | 5/2014 |
| WO | WO 2014/078578 A1 | 5/2014 |
| WO | WO 2014/164558 A1 | 10/2014 |
| WO | WO 2015/127310 A1 | 8/2015 |
| WO | WO 2015/132799 A2 | 9/2015 |
| WO | WO 2017/041536 A1 | 3/2017 |
| WO | WO 2017/066014 A1 | 4/2017 |

OTHER PUBLICATIONS

Abstract for Neplyuev, V.M. (1979), "Studies of triacylmethanes VII. 1,1,3,3-Tetraacyl-3-arylazo-1-propenes," *Zhurnal Organicheskoi Khimii*, 15(3): 563-566 (1 page).

(56) References Cited

OTHER PUBLICATIONS

Abstract for Neplyuev, V.M. (1983), "Nitration and nitrosation of 1,1,3,3-tetraacyl-1-propenes" *Ukrainskii Khimicheskii Zhurnal (Russian Edition)*, 49(2):192-194 (1 page).
Abdulahad, W.H. et al. (2012), "Immune regulation and B-cell depletion therapy in patients with primary Sjögren's syndrome," *J. Autoimmun*, 239(1): 103-111 (2012).
American Cancer Society. Can Non-Hodgkin's Lymphoma be Prevented? (2016) Web: <https://www.cancer.org/cancer/non-hodgkin-lymphoma/causes-risks--prevention/prevention.html> (3 pages).
Ansel, H.C. et al., "Pharmaceutical Dosage Forms and Drug Delivery Systems," Seventh Edition, Lippincott Williams & Wilkins, A Wolters Kluwer Company, Chapters 1-8, pp. 1-243 (1999).
Armesto, D. et al. (2010), "Efficient photochemical synthesis of 2-vinylcyclopropanecarbaldehydes, precursors of cyclopropane components present in pyrethroids, by using the oxa-di-π-methane rearrangement," *Tetrahedron*, 66: 8690-8697.
Arnold, L.D. et al. (2000), "Pyrrolo[2,3-d]pyrimidines Containing an Extended 5-Substituent as Potent and Selective Inhibitors of lck I," *Bioorg. Med. Chem. Lett.*, 10:2167-2170.
Arora, A. & E.M. Scholar (2005), "Role of Tyrosine Kinase Inhibitors in Cancer Therapy," *J. Pharmacol. Exp. Ther.*, 315(3):971-979.
Basheer, A. et al. (2007), "Enols of Substituted Cyanomalonamides," *J. Org. Chem.* 72:5297-5312.
Bastin, R.J. et al. (2000), "Salt Selection and Optimisation Procedures for Pharmaceutical New Chemical Entities," *Org. Process Res. Dev*, 4:427-435.
Berge, S.M. et al. (1977), "Pharmaceutical Salts," *J. Pharm. Sci.*, 66:1-19.
Bernhart, C.A. et al. (1983), "Synthesis and Antiarrhythmic activity of New [(Dialkylamino)alkyl]pyridylacetamides," *J. Med. Chem.*, 26:451-455.
Bradshaw, J. et al. (2015) "Prolonged and tunable residence time using reversible covalent kinase inhibitors," *Nat. Chem. Biol.*, 11:525-531 (with online methods) (10 pages).
Burchat, A.F. et al. (2000), "Pyrrolo[2,3-d]pyrimidines Containing an Extended 5-Substituent as Potent and Selective Inhibitors of lck II," *Bioorg. Med. Chem. Lett*, 10:2171-2174.
Burini, E. et al. (2005), "Efficient Synthesis of 4-Cyano 2,3-Dihydrooxazoles by Direct Amination of 2-Alkylidene 3-Oxo Nitriles," *Synlett*, 17: 2673-2675.
Calderwood, D.J. et al. (2002), "Pyrrolo[2,3-d]pyrimidines Containing Diverse N-7 Substituents as Potent Inhibitors of Lck," *Bioorg. Med. Chem. Lett.*, 12:1683-1686.
CAS RN 26272-41-3, STN entered Nov. 16, 1984 (1 page).
Certified English Translation of CN 105753863 A, published in Chinese dated Jul. 13, 2016 (57 pages).
Cohen, M.S. et al. (2005), "Structural Bioinformatics-Based Design of Selective, Irreversible Kinase Inhibitors," *Science*, 308:1318-1321.
Deng, Y.-R. et al. (2013), "Reversible phospho-Smad3 signalling between tumour suppression and fibrocarcinogenesis in chronic hepatitis B infection," *Clin. Exp. Immunol.*, 176:102-111.
Dias, A.L. & D. Jain (2013), "Ibrutinib: A New Frontier in the Treatment of Chronic Lymphocytic Leukemia by Bruton's Tyrosine Kinase Inhibition," *Cardiovasc Hematol Agents Med Chem*, 11(4):265-271.
Di Paolo, J.A. et al. (2011), "Specific Btk inhibition suppresses B cell- and myeloid cell-mediated arthritis," *Nat. Chem. Biol.*, 7:41-50.
Donald, A. et al. (2007), "Rapid Evolution of 6-Phenylpurine Inhibitors of Protein Kinase B through Structure-Based Design," *J. Med. Chem.*, 50:2289-2292.
Elinson, M.N. et al. (1998), "Electrochemical transformation of cyanoacetic ester and alkylidenecyanoacetic esters into 3-substituted 1,2-dicyanocyclopropane-1,2-dicarboxylates," *Russian Chemical Bulletin*, 47(6):1133-1136.

Elliott, M. et al., "The Pyrethrins and Related Compounds. Part XVIII. Insecticidal 2,2-Dimethylcyclopropanecarboxylates with New Unsaturated 3-Substituents," Journal of the Chemical Society, Perkin Transactions 1: Organic and Bio-Organic Chemistry (1972-1999) (1974), (21), 2470-2474.
Elliott, M. et al. (1976), "Insecticidal activity of the Pyrethrins and Related Compounds X.$^a$ 5-Benzyl-3-furylmethyl 2,2-dimethylcyclopropanecarboxylates with ethylenic substituents at position 3 on the cyclopropane ring," *Pestic. Sci.*, 7: 499-502.
English Language Abstract for JP 42008308 B4, published Apr. 8, 1967, by Yoshitomi Pharmaceutical Industries, Ltd. (1 page).
Evans, E.K. et al. (2013), "Inhibition of Btk with CC-292 Provides Early Pharmacodynamic Assessment of Activity in Mice and Humans," *J. Pharm. Exp. Ther.*, 346(2):219-28.
Fioravanti, S. et al. (2006), "Parallel Solution-Phase Synthesis of Acrylonitrile Scaffolds Carrying $_L$-α-Amino Acidic or D-Glycosyl Residues," *J. Comb. Chem.*, 8: 808-811.
Ghoreschi, K. et al. (2009), "Janus kinases in immune cell signaling," *Immunol Rev.*, 228:273-287.
Grando, S.A. (2012), "Pemphigus autoimmunity: Hypotheses and realities," *Autoimmunity*, 45(1):7-35.
Gyoung, Y.S. et al. (2000), "Regiospecific synthesis of 2-allylated-5-substituted tetrazoles via palladium-catalyzed reaction of nitriles, trimethylsilyl azide, and allyl acetates," *Tetrahedron Lett.*, 41(21): 4193-4196.
Hackam, D.G. & D.A. Redelmeier (2006), "Translation of Research Evidence from Animals to Humans," *JAMA*, 296(14):1731-1732.
Hantschel, O. et al. (2007), "The Btk tyrosine kinase is a major target of the Bcr-Abl inhibitor dasatinib." *PNAS*, 104(33): 13283-13288.
Honigberg, L.A. et al. (2010), "The Bruton tyrosine kinase inhibitor PCI-32765 blocks B-cell activation and is efficacious in models of autoimmune disease and B-cell malignacy," *PNAS*, 107(29):13075-13080.
Jenner, G. (2001), "Steric effects in high pressure Knoevenagel reactions," *Tetrahedron Lett.*, 42(2): 243-245.
Johnson, M. & K.J. Corcoran, "Coding for Dry Eye," Optometric Management, Issue: Mar. 2004 (7 pages).
Jordan, V.C. (2003), "Tamoxifen: A Most Unlikely Pioneering Medicine," *Nat. Rev. Drug Discov.*, 2:205-213.
Kamath, S. & Buolamwini J.K. (2003), "Receptor-Guided Alignment-Based Comparative 3D-QSAR Studies of Benzylidene Malonitrile Tyrphostins as EGFR and HER-2 Kinase Inhibitors," *J. Med. Chem.*, 46:4657-4668.
Kamijo, S. et al. (2003), "Tetrazole synthesis via the palladium-catalyzed three component coupling reaction," *Molecular Diversity*, 6:181-192.
Kanwar, A.J. & K. Vinay (2012), "Rituximab in Pemphigus," *Indian J. Dermatol. Venereol. Leprol*. [serial online], 78:671-676, http://www.ijdvl.com/text.asp?2012/78/6/671/102354 (10 pages).
Knight, Z.A. et al. (2007), "A membrane capture assay for lipid kinase activity," *Nat. Protoc.*, 2(10):2459-2466.
Kojima, S. et al. (2004), "Stereoselective synthesis of activated cyclopropanes with an α-pyridinium acetamide bearing an 8-phenylmenthyl group as the chiral auxiliary," *Tetrahedron Lett.*, 45(18): 3565-3568.
Komura, K. et al. (2007), "Layered silicate PLS-1: a new solid base catalyst for C—C bond forming reactions," *Catal Commun.*, 8(4): 644-648.
Kotz, A. & W. Zorning, "The Action of Chloroform on Methylene and Methenyl Groups," *Journal fuer Praktische Chemie (Leipzig)*, Abstract, 74: 425-48 (1907).
Leopold, C.S., "A Practical Approach in the Design of Colon-specific Drug Delivery System," Wiley-VCH; Drug Targeting Organ-Specific Strategies, Chapter 6, pp. 157-170 (2001).
Li Zhensu, Medicinal Chemistry, Chemical Industry Press, China, Mar. 3, 1981, pp. 435-436 (2 pages).
Lou, Y. et al. (2012), "Bruton's Tyrosine Kinase Inhibitors: Approaches to Potent and Selective Inhibition, Preclinical and Clinical Evaluation for Inflammatory Diseases and B Cell Malignancies," *J. Med. Chem.*, 55(10): 4539-4550.

(56) References Cited

OTHER PUBLICATIONS

Maas, S. et al. (1999), "Conjugate Addition of Dialkylaluminum Chlorides to Alkylidenemalonic Acid Derivatives," *Synthesis*, 10: 1792-1798.

Maurya, R.A. et al. (2013), "Catalyst-free stereoselective cyclopropanation of electron deficient alkenes with ethyl diazoacetate," *RSC Adv.*, 3:15600-15603.

MedicineNet.com. Definition of Cancer. (2004) Web: <http://www.medterms.com> (1 page).

MedlinePlus. Autoimmune Diseases (2014) Web: <https://www.nlm.nih.gov/medlineplus/autoimmunediseases.html> (5 pages).

Meydan, N. et al. (1996), "Inhibition of acute lymphoblastic leukaemia by a Jak-2 inhibitor," *Nature*, 379:645-648.

Miller, R.M., "Electrophilic Fragment-Based Design of Reversible Covalent Kinase Inhibitors," *J. Am. Chem. Soc.*, 135(14):5298-5301.

Nakamura, M. et al. (2012), "Diquafosol Ophthalmic Solution for Dry Eye Treatment," *Adv Ther*, 29(7):579-589.

Pan, Z. et al. (2007), "Discovery of Selective Irreversible Inhibitors for Bruton's Tyrosine Kinase," *ChemMedChem*, 2:58-61.

Patani, G. & E. Lavoie (1996), "Bioisosterism: A Rational Approach in Drug Design," *Chem. Rev.*, 96:3147-3176.

Pennington, L.D. et al., "The Necessary Nitrogen Atom: A Versatile High-Impact Design Element for Multiparameter Optimization," *J. Med. Chem.*, ePub Feb. 8, 2017, 28 pages, DOI: 10.1021/acs.jmedchem.6b01807.

Porter, D.W. et al. (2014), "The discovery of potent, orally bioavailable pyrimidine-5-carbonitrile-6-alkyl CXCR2 receptor antagonists," *Bioorg. Med. Chem. Lett.*, 24: 3285-3290.

Proenca, F. & Costa, M. (2008), "A simple and eco-friendly approach for the synthesis of 2-imino and 2-oxo-2H-chromene-3-carboxamides,"*Green Chem.*, 10:995-998.

Rankin, A.L. et al. (2013), "Selective Inhibition of BTK Prevents Murine Lupus and Antibody-Mediated Glomerulonephritis," *J. Immunol.*, 191(9):4540-4550.

Rellos, P. et al. (2007), "Structure and Regulation of the Human Nek2 Centrosomal Kinase," *J. Biol. Chem.*, 282(9):6833-6842.

Robak, T. & E. Robak (2012), "Tyrosine kinase inhibitors as potential drugs for B-cell lymphoid malignancies and autoimmune disorders," *Expert Opin. Investig. Drugs*, 21(7):921-947.

Sammes, M.P., et al. (1971), "α-Cyano-sulphonyl Chlorides: Their Preparation and Reactions with Amines, Alcohols, and Enamines," *J. Chem. Soc.*, I:2151-2155.

Santilli, A.A. & T.S. Osdene (1964), "8,9,10,11-Tetrahydro-12H-benzo[5,6]quinoxalino[2,3-e][1,4]diazepin-12-ones. Examples of a New Heterocyclic Ring System," *J. Org. Chem.*, 29:2066-2068.

Santus, G. & R.W. Baker (1995), "Osmotic Drug Delivery: A Review of the Patent Literature," *J. Control. Release*, 35:1-21.

Schwarz, J.B. et al. (2005), "Novel Cyclopropyl β-Amino Acid Analogues of Pregabalin and Gabapentin That Target the $α_2$-δ Protein," *J. Med. Chem.*, 48:3026-3035.

Schwöbel, J. et al. (2010), "Prediction of Michael-Type Acceptor Reactivity toward Glutathione," *Chem. Res. Toxicol.*, 23, 1576-1585.

Serafimova, I.M. et al. (2012), "Reversible targeting of noncatalytic cysteines with chemically tuned electrophiles," *Nat. Chem. Biol.*, ePub Apr. 1, 2012, 6 pages, DOI: 10.1038/nchembio.925.

Stahl, P. Heirich & C.G. Wermuth (Eds.) (2002), Handbook of Pharmaceutical Salts: Properties, Selection, and Use, Wiley-VCH; pp. 1-374.

Stevens, C.V. et al. (2002), "Synthesis of Substituted Cyclopropylphosphonates by Michael Induced Ring Closure (MIRC) Reactions," *Synlett*, 7:1089-1092.

Structure-Based Search Results (May 9, 2011, 8:13 PM), SciFinder (2 pages).

Structure-Based Search Results (May 9, 2011, 8:23 PM), SciFinder (2 pages).

Structure-Based Search Results (May 9, 2011, 8:33 PM), SciFinder (2 pages).

Structure-Based Search Results (May 9, 2011, 9:06 PM), SciFinder (2 pages).

Structure-Based Search Results (May 10, 2011, 10:04 AM), SciFinder (6 pages).

Structure-Based Search Results (May 10, 2011, 10:20 AM), SciFinder (4 pages).

Structure-Based Search Results (May 10, 2011, 10:46 AM), SciFinder (4 pages).

Verhé, R. et al. (1978), "Preparation of 2,2-Dialkylcyclopropanes Geminally Substituted with Electron-Withdrawing Groups," *Synthesis*, 7:530-532.

Verhé, R. et al. (1978), "Thermal Lactonization of Brominated Alkylidenemalonates: Synthesis of 2-Buten-4-Olides," *Bulletin des Societes Chimiques Beiges*, 87(3):215-222.

Verhé, R. et al. (1981), "Synthesis of 1,1-Bis(Hydroxymethyl) Cyclopropanes," *Org. Prep. Proced. Int.*, 13(1):13-18.

Vo, N.H. et al. (1997), "Transformations of Resin-Bound Pyridinium Ylides: I. A Stereoselective Synthesis of 2,2,3-Trisubstituted Cyclopropanecarboxylates," *Tetrahedron Lett.*, 38(46):7951-7954.

Wang, K. et al. (2009), "Cyanoacetamide Multicomponent Reaction (I): Parallel Synthesis of Cyanoacetamides," *J. Comb. Chem.*, 11:920-927.

Wang, G.T. et al. (2010), "Substituted 4-amino-1H-pyrazolo[3,4-d]pyrimidines as multi-targeted inhibitors of insulin-like growth factor-I receptor (IGFIR) and members of ErbB-family receptor kinases," *Bioorg. Med. Chem. Lett.*, 20:6067-6071.

WebMD. 10 Ways to Prevent Psoriasis Flare-Ups. (2016) Web: <http://www.webmd.com/skin-problems-and-treatments/psoriasis/prevent-flare-ups> (8 pages).

WebMD. Multiple Sclerosis (MS)—Prevention. (2015) Web: < http://www.webmd.com/multiple-sclerosis/tc/multiple-sclerosis-ms-prevention> (4 pages).

Wells, G. et al. (2000), "Structural Studies on Bioactive Compounds. 32.[1] Oxidation of Tyrphostin Protein Tyrosine Kinase Inhibitors with Hypervalent Iodine Reagents," *J. Med. Chem.*, 43:1550-1562.

WhatisDryEye.com. Dry Eye vs. Conjunctivitis (2016) Web: <http://www.whatisdryeye.com/dry-eye-vs-conjunctivitis> (5 pages).

Wilding, I.R. et al. (1994), "Targeting of Drugs and Vaccines to the Gut," *Pharmac. Ther.*, 62:97-124.

Wissner, A. et al. (2003), "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," *J. Med. Chem.*, 46:49-63.

Xu, D. et al. (2012), "RN486, a Selective Bruton's Tyrosine Kinase Inhibitor, Abrogates Immune Hypersensitivity Responses and Arthritis in Rodents," *J. Pharm. Exp. Ther.*, 341(1):90-103.

Zhang, F. et al. (2009), "Organic base catalyzed carbonyl allylation of methyl trifluoropyruvate with activated alkenes," *Tetrahedron*, 65:83-86.

Zimmerman, H.E. & W. Chen (2002), "The Diverted Di-π-Methane Rearrangement; Mechanistic and Exploratory Organic Photochemistry," *Org. Lett.*, 4(7): 1155-1158.

Communication Pursuant to Article 94(3) EPC for European Patent Application No. 13731218.7, dated Sep. 23, 2015 (4 pages).

English Translation of Office Action dated Apr. 12, 2013, in Chinese Application No. 201080061570.1 (2 pages).

Extended European Search Report for European Patent Application No. 17152898.7, dated Mar. 8, 2017 (7 pages).

International Preliminary Report on Patentability, dated May 22, 2012, in International Application No. PCT/US2010/056890, filed Nov. 16, 2010, by the Regents of the University of California (10 pages).

International Search Report dated Jul. 28, 2011, in International Application No. PCT/US2010/056890, filed Nov. 16, 2010, by the Regents of the University of California (7 pages).

International Search Report and Written Opinion dated Jul. 5, 2012, in International Patent Application No. PCT/US2012/038092, filed May 16, 2012, by Principia Biopharma Inc. (8 pages).

(56) References Cited

OTHER PUBLICATIONS

International Search Report and Written Opinion dated Aug. 20, 2012, in International Patent Application No. PCT/US2012/038120, filed May 16, 2012, by Principia Biopharma Inc. (10 pages).
International Search Report and Written Opinion dated Jul. 25, 2012, in International Application No. PCT/US2012/038135, filed May 16, 2012, by Principia Biopharma Inc. (9 pages).
International Search Report and Written Opinion dated Jul. 9, 2012, in International Patent Application No. PCT/US2012/038163, filed May 16, 2012, by Principia Biopharma Inc. (8 pages).
International Search Report dated Feb. 1, 2013, for International Application No. PCT/US2012/038214, filed May 16, 2012, by the Regents of the University of California et al. (5 pages).
International Search Report and Written Opinion dated Sep. 3, 2013, in International Patent Application No. PCT/US2013/045266, filed Jun. 11, 2013, by Principia Biopharma Inc. (11 pages).
International Search Report and Written Opinion dated Oct. 1, 2013, in International Patent Application No. PCT/US2013/047958, filed Jun. 26, 2013, by Principia Biopharma Inc. (14 pages).
International Search Report and Written Opinion dated Nov. 18, 2013, in International Patent Application No. PCT/US2013/053042, filed Jul. 31, 2013, by Principia Biopharma Inc. (12 pages).
International Search Report and Written Opinion dated Nov. 5, 2013, in International Patent Application No. PCT/US2013/058614, filed Sep. 6, 2013, by Principia Biopharma Inc. (11 pages).
International Search Report and Written Opinion dated Apr. 22, 2015, in International Patent Application No. PCT/US2015/016963, filed Feb. 20, 2015, by Mohammad Reza Masjedizadeh et al. (10 pages).
International Search Report and Written Opinion dated Mar. 9, 2016, in International Patent Application No. PCT/US2015/066868, filed Dec. 18, 2015, by Steven Gourlay (13 pages).
International Search Report and Written Opinion dated Apr. 18, 2016, in International Patent Application No. PCT/US2015/000515, filed Dec. 23, 2015, by Philip A. Nunn et al. (11 pages).
International Search Report and Written Opinion dated Mar. 21, 2016, in International Patent Application No. PCT/US2015/000303, filed Dec. 23, 2015, by Philip Nunn et al. (12 pages).
International Search Report and Written Opinion dated Aug. 16, 2016, in International Patent Application No. PCT/US2016/035588, filed Jun. 2, 2016, by Principia Biopharma Inc. (10 pages).
International Search Report and Written Opinion dated Oct. 6, 2016, in International Patent Application No. PCT/US2016/039070, filed Jun. 23, 2016, by Principia Biopharma Inc. (18 pages).
International Search Report and Written Opinion dated Oct. 2, 2017, in International Patent Application No. PCT/US2017/040075, filed Jun. 29, 2017, by Principia Biopharma Inc. (9 pages).
U.S. Appl. No. 15/072,244, filed Mar. 16, 2016, by Principia Biopharma Inc.
U.S. Appl. No. 15/188,941, filed Jun. 21, 2016, by Principia Biopharma Inc.

\* cited by examiner

HETEROCYCLE COMPRISING TYROSINE KINASE INHIBITORS

This application is a continuation of application Ser. No. 15/738,051, filed Dec. 19, 2017, which is a U.S. national phase entry under 35 U.S.C. § 371 from PCT International Application No. PCT/US2016/039070, filed Jun. 23, 2016, which claims the benefit of U.S. Provisional Application No. 62/271,715, filed Dec. 28, 2015, and U.S. Provisional Application No. 62/183,969, filed Jun. 24, 2015, each of which is incorporated herein by reference herein in its entirety.

The present disclosure provides compounds that are tyrosine kinase inhibitors, in particular Bruton tyrosine kinase ("BTK") inhibitors, and are therefore useful for the treatment of diseases such as cancer, autoimmune, inflammatory, and thromboembolic diseases. Also provided are pharmaceutical compositions containing such compounds and processes for preparing such compounds.

BTK, a member of the Tec family non-receptor tyrosine kinases, is essential for B cell signaling downstream from the B-cell receptor. It is expressed in B cells and other hematopoietic cells such as monocytes, macrophages and mast cells. It functions in various aspects of B cell function that maintain the B cell repertoire (see Gauld S. B. et al., B cell antigen receptor signaling: roles in cell development and disease. Science, 296:1641-2. 2002.) Clinical validation of the role of B cells in rheumatoid arthritis (RA) has been provided by the efficacy of Rituxan (an anti-CD20 antibody), which depletes B cells as a mechanism of action (see Perosa F., et al., CD20-depleting therapy in autoimmune diseases: from basic research to the clinic. J Intern Med. 267:260-77. 2010 and Dörner T, et al. Targeting B cells in immune-mediated inflammatory disease: a comprehensive review of mechanisms of action and identification of biomarkers. Pharmacol Ther. 125:464-75. 2010.). BTK is known to be required for B cell development because patients with defective BTK gene lack mature B cells and suffer from X-linked agammaglobulinemia (see Rosen F. S., et al., The primary immunodeficiencies. N Engl J Med. 333:431-40. 1995). Notably, small-molecule BTK inhibitors in pre-clinical development have been shown to be efficacious in collagen-induced arthritis (see Pan Z., et al., Discovery of selective irreversible inhibitors for Bruton's tyrosine kinase. J. Med. Chem. 2:58-61. 2007). However, the potential advantage of a BTK inhibitor (beyond the inherent advantage of a small-molecule over a biologic) is that modulation of BTK can inhibit B cell function without permanent removal of the B cell itself. Therefore, the long periods of low B cell levels experienced with B cell antibodies like Rituxan should be avoidable by targeting BTK.

In addition, the diseases modifying activities of BTK are expected to extend beyond those of Rituxan because of effects on addition cellular targets that are involved in propagation of disease. For instance, antigen induced mast cell degranulation is impaired in mast cells derived from the bone marrow of BTK deficient mice, demonstrating that BTK is downstream of the FcεR1 receptor (see Setoguchi R., et al., Defective degranulation and calcium mobilization of bone-marrow derived mast cells from Xid and BTK-deficient mice. Immunol Lett. 64:109-18. 1998). A similar signaling module exists in monocytes and macrophages for the FcγR1 receptor and it has been shown that BTK inhibition with a selective BTK inhibitor modulates TNF production by human monocytes stimulated with human serum albumin immune complexes (see Mina-Osorio P, et al., Suppression of glomerulonephritis in lupus-prone NZB× NZW mice by RN486, a selective inhibitor of Bruton's tyrosine kinase. Arthritis Rheum. 65: 2380-91. 2013). Both mast cells and macrophages are thought to contribute to propagation of the inflammatory cytokine environment of the diseased synovium.

In addition to the peripheral and synovial effects of BTK inhibition described above, there is evidence that BTK inhibition will have bone protective effects in the inflamed joint (see Gravallese E. M., et al., Synovial tissue in rheumatoid arthritis is a source of osteoclast differentiation factor. Arthritis Rheum. 43:250-8. 2000). Studies with mice that are either deficient in BTK or have impaired BTK function have demonstrated that Rank ligand-induced osteoclast differentiation is impaired in the absence of BTK function (see Lee S. H., et. al., The tec family tyrosine kinase BTK Regulates RANKL-induced osteoclast maturation. J. Biol. Chem. 283:11526-34. 2008). Taken together these studies suggest a BTK inhibitor could inhibit or reverse the bone destruction that occurs in RA patients. Given the importance of B cells in autoimmune disease, BTK inhibitors could also have utility in other autoimmune diseases such as systemic lupus erythematosus (see Shlomchik M. J., et. al., The role of B cells in lpr/lpr-induced autoimmunity. J. Exp Med. 180:1295-1306. 1994). Notably, BTK inhibitors have been shown to display efficacy in the murine models of systemic lupus erythematosus, reducing autoantibody production and renal damage (see Honigberg L. A., The Bruton tyrosine kinase inhibitor PCI-32765 blocks B-cell activation and is efficacious in models of autoimmune disease and B-cell malignancy. Proc. Natl. Acad. Sci. 107:13075-80. 2010 and Mina-Osorio P, et al., Suppression of glomerulonephritis in lupus-prone NZB×NZW mice by RN486, a selective inhibitor of Bruton's tyrosine kinase. Arthritis Rheum. 65: 2380-91. 2013).

There is also potential for BTK inhibitors for treating allergic diseases (see Honigberg, L., et. al., The selective BTK inhibitor PCI-32765 blocks B cell and mast cell activation and prevents mouse collagen indiced arthritis. Clin. Immunol. 127 S1:S111. 2008). In addition, the irreversible inhibitor suppresses passive cutaneous anaphylaxis (PCA) induced by IgE antigen complex in mice (see Honigberg, L., et. al., The selective BTK inhibitor PCI-32765 blocks B cell and mast cell activation and prevents mouse collagen indiced arthritis. Clin. Immunol. 127 S1:S111. 2008). These findings are in agreement with those noted with BTK-mutant mast cells and knockout mice and suggest that BTK inhibitors may be useful for the treatment of asthma, an IgE-dependent allergic disease of the airway.

In addition, platelet aggregation in response to collagen or collagen-related peptide is impaired in XLA patients who lack BTK function (see Quek L. S, et al., A role for Bruton's tyrosine kinase (BTK) in platelet activation by collagen. Curr. Biol. 8:1137-40.1998). This is manifested by changes downstream from GPIV, such as phosphorylation of PLCgamma2 and calcium flux, which suggests potential utility in treating thromboembolic diseases.

Preclinical studies with a selective inhibitor of BTK have shown effects on spontaneous canine B cell lymphomas suggesting a potential utility in human lymphomas or other hematologic malignancies including chronic lymphocytic leukemia.

Accordingly, compounds that inhibit BTK would be useful in treatment for diseases such as autoimmune diseases, inflammatory diseases, thromboembolic disease's and cancer.

SUMMARY

In a first aspect, this disclosure is directed to a compound of Formula (I):

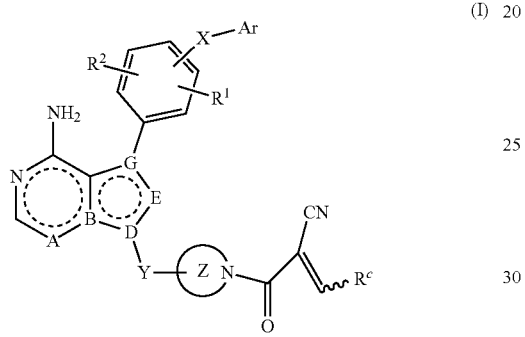

(I)

wherein:

$R^1$ and $R^2$ are independently hydrogen, alkyl, alkoxy, halolalkyl, or halo;

X is —O—, —CONR—, —NRCO—, or —NR—CO—NR' where R and R' are independently hydrogen or alkyl;

Ar is heteroaryl or phenyl, each ring optionally substituted with one, two, or three substituents independently selected from alkyl, halo, haloalkyl, alkoxy, and hydroxy;

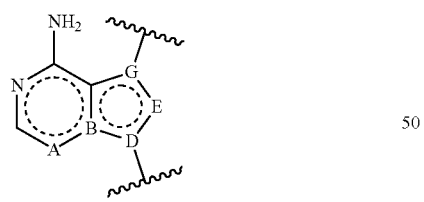

is a group of formula (i)-(x)

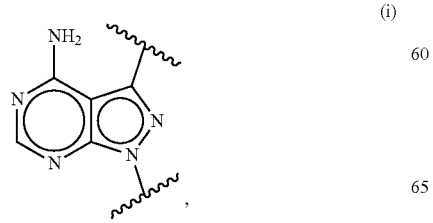

(i)

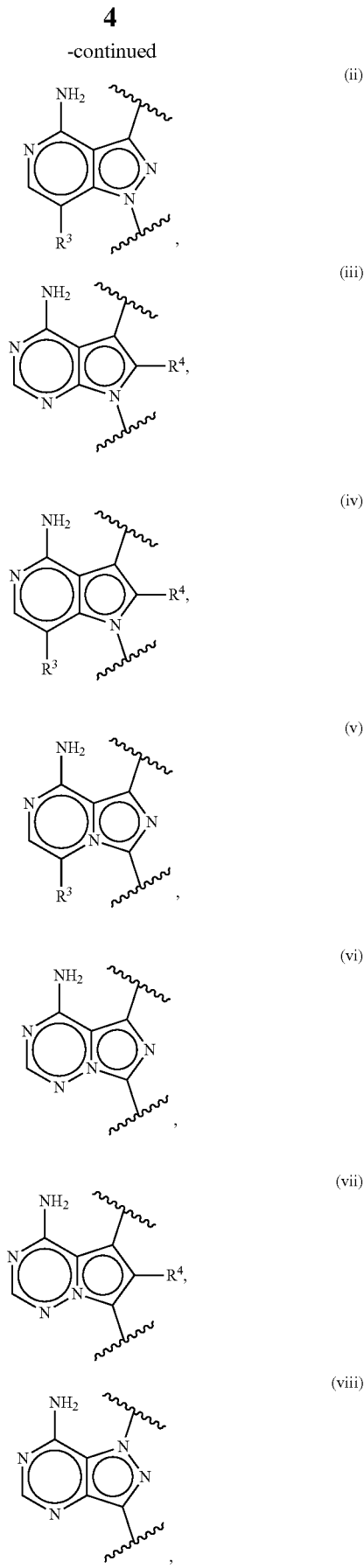

(ix)

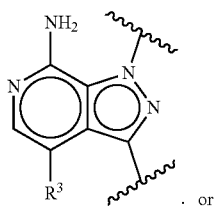

. or (x)

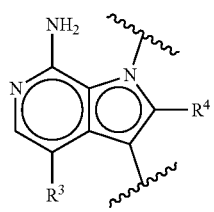

wherein:

R³ is hydrogen, alkyl, cyclopropyl, halo, haloalkyl, haloalkoxy, alkoxy, or cyano;

R⁴ is hydrogen, alkyl, or halo;

Y is bond or alkylene; or ring Z is heterocycloamino optionally substituted with one or two substituents independently selected from alkyl, hydroxy, alkoxy, and fluoro; and R^c is alkyl, cycloalkyl, hydroxyalkyl, alkoxyalkyl, -(alkylene)-NR⁶R⁷ (where R⁶ and R⁷ are independently hydrogen, alkyl, haloalkyl, hydroxyalkyl, alkoxyalkyl, cycloalkyl, or heterocyclyl wherein the heterocyclyl ring is optionally substituted with one or two substituents independently selected from alkyl, halo, hydroxy, hydroxyalkyl, alkoxyalkyl, acyl, and alkoxycarbonyl; or R⁶ and R⁷ together with the nitrogen atom to which they are attached form

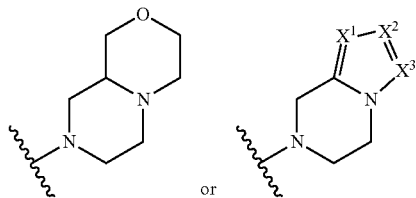

where one or two of X¹, X² and X³ are nitrogen and the rest are carbon and the ring is optionally substituted with one or two substituents independently selected from alkyl, haloalkyl, and halo), heterocyclylalkyl, or heterocyclyl, wherein the heterocyclyl and heterocyclyl in heterocyclylalkyl are independently substituted with one, two, or three substituents where two of the substituents are independently selected from hydrogen, alkyl, alkoxy, hydroxy, halo, amino, and oxo, and one of the substituent is hydrogen, alkyl, hydroxyalkyl, alkoxyalkyl, acyl, alkoxycarbonyl or heterocyclyl wherein the heterocyclyl ring is optionally substituted with one, two, or three substitutents independently selected from alkyl, halo, hydroxy, and alkoxy;

and/or a pharmaceutically acceptable salt thereof; provided that when

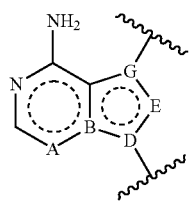

is a group of formula (i) or (iii), X is —O—, and Ar is phenyl optionally substituted with one, two, or three substituents independently selected from alkyl, halo, haloalkyl, alkoxy, and hydroxy, then R^c is heterocyclylalkyl wherein the heterocyclyl ring in heterocyclylalkyl is substituted with one, two, or three substituents where two substituents are independently selected from hydrogen, alkyl, alkoxy, hydroxy, halo, amino, and oxo, and one of the substituent is heterocyclyl that is substituted with alkyl or fluoro on the carbon atom of heterocyclyl that is attached to the heterocyclyl of heterocyclylalkyl.

In one embodiment, the compounds of Formula (I) and/or a pharmaceutically acceptable salt thereof (and any embodiments thereof disclosed herein) can form a reversible covalent bond with Cys481 of BTK.

In a second aspect, this disclosure is directed to a pharmaceutical composition comprising a compound of Formula (I) (or any of the embodiments thereof described herein), and/or a pharmaceutically acceptable salt thereof; and a pharmaceutically acceptable excipient.

(a) In embodiment (a) of the second aspect, the formulation is a solid oral formulation comprising:

(i) a compound of Formula (I) and/or a pharmaceutically acceptable salt thereof (or any embodiment thereof disclosed herein): and (ii) means for release of said compound and/or a pharmaceutically acceptable salt thereof in the intestine.

(b) In embodiment (b), of the second aspect, the formulation is a solid oral formulation comprising means for release of a therapeutically effective amount of a compound of Formula (I) and/or a pharmaceutically acceptable salt thereof (or any embodiment thereof disclosed herein) from said oral formulation in the intestine.

Within embodiment (a) or (b), in one embodiment the compound of Formula (I) and/or a pharmaceutically acceptable salt thereof (or any embodiment thereof disclosed herein) is released in the small intestine. Preferably, in jejunum and/or ileum.

In yet another embodiment of embodiment (a) or (b) and embodiments contained therein, the release of a compound of Formula (I) and/or a pharmaceutically acceptable salt thereof (or any embodiment thereof disclosed herein) in the intestine, including small intestine or region(s) thereof is achieved by coating (i) the compound of Formula (I) and/or a pharmaceutically acceptable salt thereof (or embodiments thereof disclosed herein); and/or (ii) the dosage form comprising a compound of Formula (I) (or embodiments thereof disclosed herein) and/or a pharmaceutically acceptable salt thereof; with a coating chosen from an enteric coating and/or a non-enteric time-delayed release coating.

In one embodiment, when the compound of Formula (I) and/or a pharmaceutically acceptable salt thereof (or embodiments thereof disclosed herein) and/or the dosage form comprising the compound of Formula (I) and/or a pharmaceutically acceptable salt thereof (or embodiments thereof disclosed herein) is coated with an enteric coating, the enteric coating is a polymer. In another embodiment, when the compound of Formula (I) and/or a pharmaceutically acceptable salt thereof and/or the dosage form comprising the compound of Formula (I) and/or a pharmaceutically acceptable salt thereof disclosed herein is coated with an enteric coating, the enteric coating is an anionic polymer such as selected from polymethacrylates (e.g., methacrylic acid ethacrylate poly, methacrylic acid methyl methacrylate poly); cellulose-based polymers (e.g., cellulose acetate phthalate CAP, cellulose acetate trimellitate CAT, cellulose acetate succinate CAS, hydroxypropylmethylcellulose phthalate HPMCP, hydroxypropylmethylcellulose acetate succinate HPMCAS), and polyvinyl derivatives such as polyvinyl acetate phthalate PVAP. In yet another embodiment, the enteric coating erodes in the gastrointestinal track having a pH from about 4.5 to about 7 or about 5.5 to about 7 to release the compound of Formula (I) and/or a pharmaceutically acceptable salt thereof (or embodiments thereof disclosed herein).

When a non-enteric coating is employed, the non-enteric time-delayed release dosage forms can be administered in fasted state and the time-delayed release coating can be designed to erode, burst, or become highly permeable in about 0.3 to about 3 hours or in about 0.5 to about 2 hours after administration to release the compound of Formula (I) (or embodiments thereof disclosed herein); and/or a pharmaceutically acceptable salt thereof.

In a third aspect, this disclosure is directed to a method of treating a disease treatable by inhibition of BTK in a mammal in need thereof which method comprises administering to the mammal in need thereof, a pharmaceutical composition comprising a therapeutically effective amount of a compound of Formula (I) (or any of the embodiments thereof described herein) and/or a pharmaceutically acceptable salt thereof, and a pharmaceutically acceptable excipient. In one embodiment the disease is cancer, autoimmune, inflammatory, or thromboembolic diseases. In another embodiment, the disease is Acute Disseminated Encephalomyelitis (ADEM), acute necrotizing hemorrhagic leukoencephalitis, acutedisseminatedencephalomyelitis, Addison's disease, agammaglobulinemia, alopecia areata, alopecia universalis, amyloidosis, ankylosing spondylitis, anti-GBM/Anti-IBM nephritis, antiphospholipid syndrome (APS), antiphospholipid antibody syndrome, aplastic anemia, arthritis, autoimmune angioedema, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, autoimmune hemolyticanemia, axonal & neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, coeliac disease, Cogans syndrome, cold agglutinin disease, congenital heart block, coxsackie myocarditis, CREST disease, Crohn's disease, demyelinating neuropathies, dermatitis herpetiformis, dermatomyositis, Devic's disease (neuromyelitis optica), diabetes, discoid lupus, Dressler's syndrome, dry eye, dysautonomia, endometriosis, eosinophilic esophagitis, eosinophilic fasciitis, erythema nodosum, essential mixed cryoglobulinemia, Evans syndrome, experimental allergic encephalomyelitis, fibromyalgia, fibrosing alveolitis, giant cell arteritis (temporal arteritis), giant cell myocarditis, glomerulonephritis, Goodpasture's syndrome, Granulomatosis with Polyangiitis (GPA) (formerly called Wegener's Granulomatosis), Graves' disease, Guillain-Barre syndrome, Guillain-Barre syndrome, Hashimoto's thyroiditis, hemolytic anemia, Henoch-Schonlein purpura, herpes gestationis, hypogammaglobulinemia, Idiopathic pulmonary fibrosis, idiopathic thrombocytopenic purpura (ITP), IgA nephropathy, IgG4-related sclerosing disease, immunoregulatory lipoproteins, inclusion body myositis, inflammatory bowel disease, interstitial cystitis, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (SLE), lupus including lupus nephritis, lyme disease, chronic, Meniere's disease, microscopic polyangiitis, mixed connective tissue disease (MCTD), mooren's ulcer, Mucha-Habermann disease, mucous membrane pemphigoid, multiple sclerosis, myasthenia gravis, myositis, narcolepsy, neuromyelitis optica (Devic's), neuromyotonia, neutropenia, ocular cicatricial pemphigoid, opsoclonus-myoclonus syndrome, optic neuritis, Ord's thyroiditis, osteoarthritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, pars planitis (peripheral uveitis), Parsonnage-Turner syndrome, peripheral neuropathy, perivenous encephalomyelitis, pernicious anemia, phemphigus such as phemphigus vulgaris and/or foliaceus, POEMS syndrome, polyarteritis nodosa, polymyalgia rheumatica, Polymyositis, Postmyocardial infarction syndrome, Postpericardiotomy syndrome, primary biliary cirrhosis, primary sclerosing cholangitis, primary biliary cirrhosis, progesterone dermatitis, psoriasis, psoriatic arthritis, psoriaticarthritis, pure red cell aplasia, pyoderma gangrenosum, raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, Still's disease, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, Type I, II, & III autoimmune polyglandular syndromes, ulcerative colitis, undifferentiated connective tissue disease (UCTD), uveitis, vasculitis, vesiculobullous dermatosis, vitiligo, vulvodynia, or lupus.

In one embodiment of the third aspect, the mammal is suffering from an autoimmune disease, e.g., inflammatory bowel disease, arthritis, lupus including Lupus Nephritis, rheumatoid arthritis, psoriatic arthritis, osteoarthritis, Still's disease, juvenile arthritis, diabetes, myasthenia gravis, Granulomatosis with Polyangiitis, Hashimoto's thyroiditis, Ord's thyroiditis, Graves' disease, Sjogren's syndrome, dry eye, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, phemphigus such as phemphigus vulgaris and/or foliaceus, bullous pemphigoid, age-related macular degeneration, diabetic macular edema, corneal transplantation, abdominal aortic aneurysm, mucous membrane pemphigoid, or vulvodynia. In another embodiment, the autoimmune disease is lupus, phemphigus vulgaris, myasthenia gravis, Sjogren's syndrome, dry eye, multiple sclerosis, Wegener's granulomatosis, autoimmune hemolytic anemia, idiopathic thrombocytopenic purpura, Granulomatosis with Polyangiitis, or rheumatoid arthritis.

In another embodiment of the third aspect, the mammal is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis. In another embodiment, the disease is atopic dermatitis.

In yet another embodiment of the third aspect, the mammal is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. In another embodiment of this aspect, the mammal is suffering from inflammatory skin disease which includes, by way of example, dermatitis, contact dermatitis, eczema, urticaria, rosacea, and scarring psoriatic lesions in the skin, joints, or other tissues or organs. In another embodiment, the inflammatory disease is asthma or dermatitis.

In yet another embodiment of the third aspect, the mammal is suffering from a cancer. In one embodiment, the cancer is a B-cell proliferative disorder, e.g., diffuse large B cell lymphoma, follicular lymphoma, chronic lymphocytic lymphoma (CLL), chronic lymphocytic leukemia, chromic myelogenous leukemia, B-ALL, Philadelphia chromosome positive B-ALL, B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, and lymphomatoid granulomatosis.

In yet another embodiment of the third aspect, the mammal is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a fourth aspect, the disclosure is directed to a compound of Formula (I) (and any embodiments thereof described herein) and/or a pharmaceutically acceptable salt thereof for use as a medicament. In one embodiment, the use of compound of Formula (I) and/or a pharmaceutically acceptable salt thereof is for treating a disease mediated by BTK, for example, the disease is an inflammatory disease, autoimmune disease, cancer, or thromboembolic diseases described in the third aspect and embodiments therein.

In a fifth aspect, the disclosure is directed to the use of a compound of Formula (I) (or any of the embodiments thereof described herein) and/or a pharmaceutically acceptable salt thereof, in the manufacture of a medicament for treating a disease in a mammal in which BTK contributes to the pathology and/or symptoms of the disease. In one embodiment of this aspect, the disease is cancer, autoimmune, inflammatory, or thromboembolic disease described in the third aspect and embodiments therein.

In any of the aforementioned aspects involving the treatment cancer, disclosed are further embodiments comprising administering the compound of Formula (I) (or any of the embodiments thereof described herein) and/or a pharmaceutically acceptable salt thereof, in combination with an anti-cancer agent. When combination therapy is used, the agents can be administered simultaneously (such as in a fixed combination drug product- or sequentially.

In a sixth aspect, this disclosure is directed to an intermediate of Formula (II):

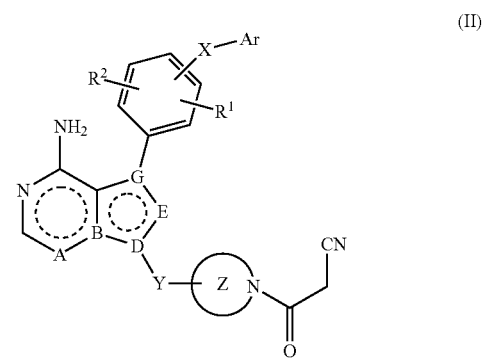

wherein:
R$^1$, R$^2$, X, Ar, Y, ring Z and

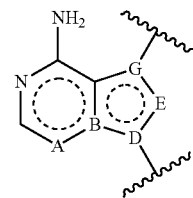

are as defined in the first aspect above;
or a salt thereof, provided that when X is —O—, and Ar is phenyl optionally substituted with one, two, or three substituents independently selected from alkyl, halo, haloalkyl, alkoxy, and hydroxy, then

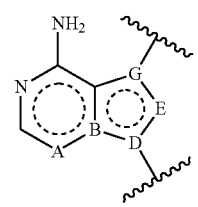

is not a group of formula (i) or (iii). In one embodiment,

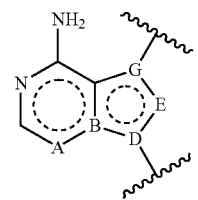

is a group of formula of (ii).

In a seventh aspect, provided is a process of preparing a compound of Formula (I) as defined in the first aspect above: or
and/or a pharmaceutical salt thereof;
comprising:
(a) reacting a compound of Formula (II'):

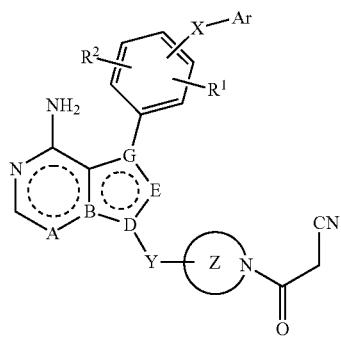

wherein:
$R^1$, $R^2$, X, Ar, Y, ring Z and

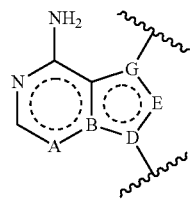

are as defined in the first aspect above;
with an aldehyde of formula $R^cCHO$ where $R^c$ is as defined in the first aspect; or
(b) reacting a compound of formula (III):

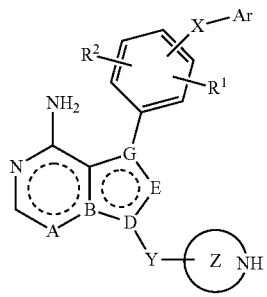

wherein:
$R^1$, $R^2$, X, Ar, Y, ring Z, and

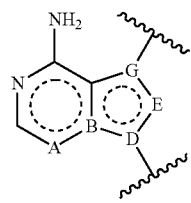

are as defined in the first aspect above;

with a compound of formula $R^cCH=C(CN)COL$ where L is a leaving group and $R^c$ is as defined in the first aspect above;
(c) optionally making an acid addition salt of a compound obtained from Steps (a) or (b) above;
(d) optionally making a free base of a compound obtained from Steps (a) or (b) above;
provided that when

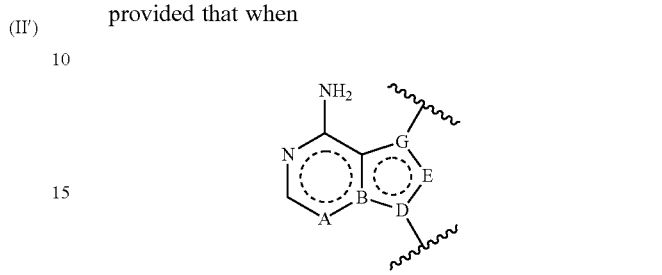

is a group of formula (i) or (iii), X is —O—, and Ar is phenyl optionally substituted with one, two, or three substituents independently selected from alkyl, halo, haloalkyl, alkoxy, and hydroxy, then $R^c$ is heterocyclylalkyl wherein the heterocyclyl ring in heterocyclylalkyl is substituted with one, two, or three substituents where two substituents are independently selected from hydrogen, alkyl, alkoxy, hydroxy, halo, amino, and oxo, and one of the substituent is heterocyclyl that is substituted with alkyl or fluoro on the carbon atom of heterocyclyl that is attached to the heterocyclyl of heterocyclylalkyl.

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with an alkoxy group, (in one embodiment one or two alkoxy groups), as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Acyl" means a —COR radical where R is alkyl, haloalkyl, or cycloalkyl, e.g., acetyl, propionyl, cyclopropylcarbonyl, and the like. When R is alkyl, the radical is also referred to herein as alkylcarbonyl.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Carboxy" means —COOH.

"Halo" means fluoro, chloro, bromo, or iodo; in one embodiment fluoro or chloro.

"Haloalkyl" means alkyl radical as defined above, which is substituted with one or one to five halogen atoms (in one embodiment fluorine or chlorine,) including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it can referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl. In one embodiment 2-hydroxyethyl, 2,3-dihydroxypropyl, and 1-(hydroxymethyl)-2-hydroxyethyl.

"Heterocyclyl" means a saturated or unsaturated monovalent monocyclic or bicyclic group (such as fused ring) of 4 to 10 ring atoms in which one or two ring atoms are heteroatom selected from N, O, and S(O)$_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, oxetanyl, pyrrolidino, piperidino, homopiperidino, 2-oxopyrrolidinyl, 2-oxopiperidinyl, morpholino, piperazino, tetrahydropyranyl, thiomorpholino, hexahydropyrrolo[1,2-a]pyrazin-6(2H)-one-yl, tetrahydro-1H-oxazolo[3,4-a]pyrazin-3(5H)-one-yl and the like. When the heterocyclyl ring is unsaturated it can contain one or two ring double bonds provided that the ring is not aromatic "Heterocyclylalkyl" means a -(alkylene)-R radical where R is heterocyclyl ring as defined above e.g., tetraydrofuranylmethyl, piperazinylmethyl, morpholinylethyl, and the like.

"Heterocycloamino" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group. When the heterocycloamino ring is unsaturated it can contain one or two ring double bonds provided that the ring is not aromatic.

"Heteroaryl" means a monovalent monocyclic or bicyclic aromatic radical of 5 to 10 ring atoms where one or more, (in one embodiment one, two, or three), ring atoms are heteroatom selected from N, O, and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Mammal" as used herein means domesticated animals (such as dogs, cats, and horses), and humans. In one embodiment, mammal is a human.

The present disclosure also includes the prodrugs of compounds of Formula (I) (or any of the embodiments thereof described herein) and/or a pharmaceutically acceptable salt thereof. The term prodrug is intended to represent covalently bonded carriers, which are capable of releasing the active ingredient of Formula (I) (or any of the embodiments thereof described herein) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) (or any of the embodiments thereof described herein) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) (or any of the embodiments thereof described herein) and/or a pharmaceutically acceptable salt thereof are also within the scope of this disclosure.

The present disclosure also includes polymorphic forms (amorphous as well as crystalline) and deuterated forms of compounds of Formula (I) (or any of the embodiments thereof described herein) and/or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms, as individual forms and mixtures thereof, are within the scope of this disclosure, unless the specific stereochemistry or isomeric form is specifically indicated.

Certain compounds of Formula (I) (or any of the embodiments thereof described herein) and/or a pharmaceutically acceptable salt thereof can exist as tautomers and/or geometric isomers. All possible tautomers and cis and trans isomers, as individual forms and mixtures thereof, are within the scope of this disclosure. Additionally, as used herein the term alkyl includes all the possible isomeric forms of said alkyl group albeit only a few examples are set forth. Furthermore, when the cyclic groups such as heteroaryl, heterocyclyl are substituted, they include all the positional isomers albeit only a few examples are set forth. Furthermore, all hydrate forms of a compound of Formula (I) (or any of the embodiments thereof described herein) and/or a pharmaceutically acceptable salt thereof are within the scope of this disclosure.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The phrase "heterocyclyl and heterocyclyl in heterocyclylalkyl are independently substituted with one, two, or three substituents where two of the substituents are independently selected from hydrogen, alkyl, alkoxy, hydroxy, halo, and oxo, and one of the substituent is hydrogen, alkyl, cycloalkyl, hydroxyalkyl, alkoxyalkyl, acyl, haloalkyl, alkylsulfonyl, alkoxycarbonyl, or heterocyclyl" in the definition of in $R^c$ in Formula (I) (and similar phrases elsewhere in the claim and/or specification) means that when heterocyclyl is substituted with one substituent, the substituent can selected from all the substituents listed. When heterocyclyl ring is substituted with two substituents, then both substituents can either be selected from hydrogen, alkyl, alkoxy, hydroxy, halo, and oxo or one of the two substituent is selected from hydrogen, alkyl, alkoxy, hydroxy, halo, and oxo and the other substituent is selected from hydrogen, alkyl, cycloalkyl, hydroxyalkyl, alkoxyalkyl, acyl, haloalkyl, alkylsulfonyl, alkoxycarbonyl, and heterocyclyl.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I) (or any of the embodiments thereof described herein), that, when administered to a mammal for treating a disease, is sufficient to effect such treatment for the disease. The "therapeutically effective amount" will vary depending on the compound, the disease and its severity and the age, weight, etc., of the mammal to be treated.

Representative compounds of the Disclosure are:

TABLE I

| Cpd No. | Name | MS M + 1 |
|---|---|---|
| 1 | (R)-2-(3-(4-amino-3-(2-fluoro-4-phenoxyphenyl)-1H-pyrazolo[4,3-c]pyridin-1-yl)piperidine-1-carbonyl)-4-methyl-4-(4-(oxetan-3-yl)piperazin-1-yl)pent-2-enenitrile | 666.3 |
| 2 | (R)-2-(3-(8-amino-1-(2-fluoro-4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile | 664.9 |
| 3 | (R)-2-(3-(4-amino-5-(2-fluoro-4-phenoxyphenyl)imidazo[5,1-f][1,2,4]triazin-7-yl)piperidine-1-carbonyl)-4-methyl-4-(4-(oxetan-3-yl)piperazin-1-yl)pent-2-enenitrile | |
| 4 | (R)-2-(3-(4-amino-5-(2-fluoro-4-phenoxyphenyl)-7H-pyrrolo[2,3-d]pyrimidin-7-yl)piperidine-1-carbonyl)-4-methyl-4-(4-(oxetan-3-yl)piperazin-1-yl)pent-2-enenitrile | |
| 5 | (S)-2-(3-(4-amino-5-(2-fluoro-4-phenoxyphenyl)-5H-pyrrolo[3,2-d]pyrimidin-7-yl)piperidine-1-carbonyl)-4-methyl-4-(4-(oxetan-3-yl)piperazin-1-yl)pent-2-enenitrile | |
| 6 | (R)-2-(3-(7-amino-1-(2-fluoro-4-phenoxyphenyl)-1H-pyrazolo[4,3-d]pyrimidin-3-yl)piperidine-1-carbonyl)-4-methyl-4-(4-(oxetan-3-yl)piperazin-1-yl)pent-2-enenitrile | |
| 7 | (R)-2-(3-(4-amino-3-(2-fluoro-4-phenoxyphenyl)-1H-pyrazolo[4,3-c]pyridin-1-yl)piperidine-1-carbonyl)-4-methyl-4-(4-(3-methyloxetan-3-yl)piperazin-1-yl)pent-2-enenitrile | 680.4 |
| 8 | (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(3-methyloxetan-3-yl)piperazin-1-yl)pent-2-enenitrile | 681.3 |
| 9 | (R)-2-(3-(4-amino-3-(2-fluoro-4-phenoxyphenyl)-1H-pyrazolo[4,3-c]pyridin-1-yl)piperidine-1-carbonyl)-4,4-dimethylpent-2-enenitrile | 539.2 |
| 10 | (R)-2-(3-(4-amino-3-(2-fluoro-4-phenoxyphenyl)-1H-pyrazolo[4,3-c]pyridin-1-yl)piperidine-1-carbonyl)-4-methyl-4-(4-methylpiperazin-1-yl)pent-2-enenitrile | 623.1 |

TABLE I-continued

| Cpd No. | Name | MS M + 1 |
|---|---|---|
| 11 | (R)-2-(3-(4-amino-3-(2-fluoro-4-phenoxyphenyl)-1H-pyrazolo[4,3-c]pyridin-1-yl)piperidine-1-carbonyl)-4-methyl-4-morpholinopent-2-enenitrile | 610.2 |
| 12 | (S)-2-(2-((4-amino-3-(2-fluoro-4-phenoxyphenyl)-1H-pyrazolo[4,3-c]pyridin-1-yl)methyl)pyrrolidine-1-carbonyl)-4-methyl-4-(4-methylpiperazin-1-yl)pent-2-enenitrile | 623.1 |
| 13 | (S)-2-(2-((4-amino-3-(2-fluoro-4-phenoxyphenyl)-1H-pyrazolo[4,3-c]pyridin-1-yl)methyl)pyrrolidine-1-carbonyl)-4-methyl-4-(4-(oxetan-3-yl)piperazin-1-yl)pent-2-enenitrile | 665.3 |
| 14 | (R)-2-(3-(4-amino-3-(2-fluoro-4-phenoxyphenyl)-1H-pyrazolo[4,3-c]pyridin-1-yl)piperidine-1-carbonyl)-4-methyl-4-(methyl(oxetan-3-yl)amino)pent-2-enenitrile | |
| 15 | (S)-4-(4-amino-1-((1-(2-cyano-4-methyl-4-(4-(oxetan-3-yl)piperazin-1-yl)pent-2-enoyl)pyrrolidin-2-yl)methyl)-1H-pyrazolo[4,3-c]pyridin-3-yl)-N-(pyridin-2-yl)benzamide | 675.3 |
| 16 | (S)-2-(2-((8-amino-1-(2-fluoro-4-phenoxyphenyl)imidazo[1,5-a]pyrazin-3-yl)methyl)pyrrolidine-1-carbonyl)-4,4-dimethylpent-2-enenitrile | 538.9 |
| 17 | (S)-2-(2-((8-amino-1-(2-fluoro-4-phenoxyphenyl)imidazo[1,5-a]pyrazin-3-yl)methyl)pyrrolidine-1-carbonyl)-4-methyl-4-morpholinopent-2-enenitrile | 609.9 |
| 18 | (S)-2-(2-((8-amino-1-(2-fluoro-4-phenoxyphenyl)imidazo[1,5-a]pyrazin-3-yl)methyl)pyrrolidine-1-carbonyl)-4-methyl-4-(methyl(oxetan-3-yl)amino)pent-2-enenitrile | 609.9 |
| 19 | (S)-2-(2-((8-amino-1-(2-fluoro-4-phenoxyphenyl)imidazo[1,5-a]pyrazin-3-yl)methyl)pyrrolidine-1-carbonyl)-4-methyl-4-(4-(oxetan-3-yl)piperazin-1-yl)pent-2-enenitrile | 665.3 |
| 20 | (S)-4-(4-amino-1-((1-(2-cyano-4-methyl-4-(4-methylpiperazin-1-yl)pent-2-enoyl)pyrrolidin-2-yl)methyl)-1H-pyrazolo[4,3-c]pyridin-3-yl)-N-(pyridin-2-yl)benzamide | 633.4 |
| 21 | (S)-4-(4-amino-1-((1-(2-cyano-4-methyl-4-morpholinopent-2-enoyl)pyrrolidin-2-yl)methyl)-1H-pyrazolo[4,3-c]pyridin-3-yl)-N-(pyridin-2-yl)benzamide | 620.3 |
| 22 | (S)-2-(2-((4-amino-3-(2-fluoro-4-phenoxyphenyl)-1H-pyrazolo[4,3-c]pyridin-1-yl)methyl)pyrrolidine-1-carbonyl)-4-methyl-4-morpholinopent-2-enenitrile | 610.2 |
| 23 | (R)-2-(3-(4-amino-3-(2-fluoro-4-phenoxyphenyl)-1H-pyrazolo[4,3-c]pyridin-1-yl)piperidine-1-carbonyl)-4-methyl-4-(1-(oxetan-3-yl)piperidin-4-yl)pent-2-enenitrile | 663.8 |
| 24 | (R)-2-(3-(4-amino-3-(2-fluoro-4-phenoxyphenyl)-1H-pyrazolo[4,3-c]pyridin-1-yl)piperidine-1-carbonyl)-4-methyl-4-(3-oxopiperazin-1-yl)pent-2-enenitrile | 623.3 |
| 25 | (R)-2-(3-(4-amino-3-(2-methyl-4-phenoxyphenyl)-1H-pyrazolo[4,3-c]pyridin-1-yl)piperidine-1-carbonyl)-4-methyl-4-(4-(oxetan-3-yl)piperazin-1-yl)pent-2-enenitrile | 661.0 |
| 26 | (R)-2-(3-(4-amino-3-(3-fluoro-4-phenoxyphenyl)-1H-pyrazolo[4,3-c]pyridin-1-yl)piperidine-1-carbonyl)-4-methyl-4-(4-(oxetan-3-yl)piperazin-1-yl)pent-2-enenitrile | 665.0 |
| 27 | (R)-2-(3-(4-amino-3-(3-methyl-4-phenoxyphenyl)-1H-pyrazolo[4,3-c]pyridin-1-yl)piperidine-1-carbonyl)-4-methyl-4-(4-(oxetan-3-yl)piperazin-1-yl)pent-2-enenitrile | 660.8 |
| 28 | (R)-2-(3-(4-amino-3-(4-(2,6-difluorophenoxy)phenyl)-1H-pyrazolo[4,3-c]pyridin-1-yl)piperidine-1-carbonyl)-4-methyl-4-(4-(oxetan-3-yl)piperazin-1-yl)pent-2-enenitrile | 682.9 |
| 29 | (R)-2-(3-(4-amino-3-(4-(2,3-difluorophenoxy)phenyl)-1H-pyrazolo[4,3-c]pyridin-1-yl)piperidine-1-carbonyl)-4-methyl-4-(4-(oxetan-3-yl)piperazin-1-yl)pent-2-enenitrile | 682.9 |
| 30 | (R)-4-(4-amino-1-(1-(2-cyano-4-methyl-4-(4-(oxetan-3-yl)piperazin-1-yl)pent-2-enoyl)piperidin-3-yl)-1H-pyrazolo[4,3-c]pyridin-3-yl)-N-(pyridin-2-yl)benzamide | 674.0 |
| 31 | (S)-2-(2-((4-amino-3-(2-fluoro-4-phenoxyphenyl)-1H-pyrazolo[4,3-c]pyridin-1-yl)methyl)pyrrolidine-1-carbonyl)-4-(4-ethyl-3-oxopiperazin-1-yl)-4-methylpent-2-enenitrile | 651.3 |
| 32 | (S)-2-(2-((4-amino-3-(2-fluoro-4-phenoxyphenyl)-1H-pyrazolo[4,3-c]pyridin-1-yl)methyl)pyrrolidine-1-carbonyl)-4-methyl-4-(4-methyl-3-oxopiperazin-1-yl)pent-2-enenitrile | 637.3 |
| 33 | (R)-2-(3-(4-amino-3-(2-fluoro-4-phenoxyphenyl)-1H-pyrazolo[4,3-c]pyridin-1-yl)piperidine-1-carbonyl)-4-methyl-4-(4-methyl-1-(oxetan-3-yl)piperidin-4-yl)pent-2-enenitrile | 677.2 |
| 34 | (R)-2-(3-(4-amino-3-(4-phenoxyphenyl)-1H-pyrazolo[4,3-c]pyridin-1-yl)piperidine-1-carbonyl)-4-methyl-4-(4-(oxetan-3-yl)piperazin-1-yl)pent-2-enenitrile | 647.3 |
| 35 | (R)-2-(3-(8-amino-1-(4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile | 646.8 |
| 36 | (R)-2-(3-(4-amino-5-(4-phenoxyphenyl)imidazo[5,1-f][1,2,4]triazin-7-yl)piperidine-1-carbonyl)-4-methyl-4-(4-(oxetan-3-yl)piperazin-1-yl)pent-2-enenitrile | |
| 37 | (S)-2-(3-(4-amino-5-(4-phenoxyphenyl)-5H-pyrrolo[3,2-d]pyrimidin-7-yl)piperidine-1-carbonyl)-4-methyl-4-(4-(oxetan-3-yl)piperazin-1-yl)pent-2-enenitrile | |
| 38 | (R)-2-(3-(7-amino-1-(4-phenoxyphenyl)-1H-pyrazolo[4,3-d]pyrimidin-3-yl)piperidine-1-carbonyl)-4-methyl-4-(4-(oxetan-3-yl)piperazin-1-yl)pent-2-enenitrile | |
| 39 | (R)-2-(3-(4-amino-3-(4-phenoxyphenyl)-1H-pyrazolo[4,3-c]pyridin-1-yl)piperidine-1-carbonyl)-4-methyl-4-(4-(3-methyloxetan-3-yl)piperazin-1-yl)pent-2-enenitrile | 661.3 |
| 40 | (R)-2-(3-(4-amino-3-(2-fluoro-4-phenoxyphenyl)-1H-pyrazolo[4,3-c]pyridin-1-yl)piperidine-1-carbonyl)-4-methyl-4-(4-ethyl-3-oxopiperazin-1-yl)pent-2-enenitrile | 651.3 |
| 41 | (R)-2-(3-(4-amino-3-(4-phenoxyphenyl)-1H-pyrazolo[4,3-c]pyridin-1-yl)piperidine-1-carbonyl)-4-(4-ethyl-3-oxopiperazin-1-yl)-4-methylpent-2-enenitrile | 633.3 |

TABLE I-continued

| Cpd No. | Name | MS M + 1 |
|---|---|---|
| 42 | (R)-2-(3-(4-amino-3-(4-phenoxyphenyl)-1H-pyrazolo[4,3-c]pyridin-1-yl)piperidine-1-carbonyl)-3-(4-methyl-1-(oxetan-3-yl)piperidin-4-yl)acrylonitrile | 618.3 |
| 43 | (R)-2-(3-(4-amino-3-(4-phenoxyphenyl)-1H-pyrazolo[4,3-c]pyridin-1-yl)piperidine-1-carbonyl)-3-(4-methyltetrahydro-2H-pyran-4-yl)acrylonitrile | 563.3 |
| 44 | (R)-2-(3-(4-amino-3-(4-(2-fluorophenoxy)phenyl)-1H-pyrazolo[4,3-c]pyridin-1-yl)piperidine-1-carbonyl)-4-methyl-4-(4-(oxetan-3-yl)piperazin-1-yl)pent-2-enenitrile | 664.7 |
| 45 | (R)-4-(4-amino-1-(1-(2-cyano-4-methyl-4-(4-methylpiperazin-1-yl)pent-2-enoyl)piperidin-3-yl)-1H-pyrazolo[4,3-c]pyridin-3-yl)-N-(pyridin-2-yl)benzamide | 633.0 |
| 46 | (R)-4-(4-amino-1-(1-(2-cyano-4-methyl-4-(methyl(oxetan-3-yl)amino)pent-2-enoyl)piperidin-3-yl)-1H-pyrazolo[4,3-c]pyridin-3-yl)-N-(pyridin-2-yl)benzamide | 620.2 |
| 47 | (R)-4-(4-amino-1-(1-(2-cyano-4-methyl-4-(4-(oxetan-3-yl)piperazin-1-yl)pent-2-enoyl)piperidin-3-yl)-1H-pyrazolo[4,3-c]pyridin-3-yl)-N-(pyridin-2-yl)benzamide | 675 |
| 48 | (R)-2-(3-(4-amino-3-(2-fluoro-4-phenoxyphenyl)-1H-pyrazolo[4,3-c]pyridin-1-yl)piperidine-1-carbonyl)-3-(4-methyltetrahydro-2H-pyran-4-yl)acrylonitrile | 581.5 |
| 49 | (R)-2-(3-(4-amino-3-(2-fluoro-4-phenoxyphenyl)-1H-pyrazolo[4,3-c]pyridin-1-yl)piperidine-1-carbonyl)-3-(4-methyl-1-(oxetan-3-yl)piperidin-4-yl)acrylonitrile | 636.3 |
| 50 | (R)-4-(4-amino-1-(1-(2-cyano-4-methyl-4-(4-(oxetan-3-yl)piperazin-1-yl)pent-2-enoyl)piperidin-3-yl)-1H-pyrazolo[4,3-c]pyridin-3-yl)-N-(4-fluoropyridin-2-yl)benzamide | 692.9 |
| 51 | (R)-2-(3-(8-amino-1-(2-fluoro-4-phenoxyphenyl)imidazo[1,5-a]pyrazin-3-yl)piperidine-1-carbonyl)-4-methyl-4-(4-methyl-3-oxopiperazin-1-yl)pent-2-enenitrile | 636.7 |
| 52 | (R)-2-(3-(8-amino-1-(4-phenoxyphenyl)imidazo[1,5-a]pyrazin-3-yl)piperidine-1-carbonyl)-4-methyl-4-(4-methyl-3-oxopiperazin-1-yl)pent-2-enenitrile | 618.8 |
| 53 | (R)-2-(3-(8-amino-1-(2-fluoro-4-phenoxyphenyl)imidazo[1,5-a]pyrazin-3-yl)piperidine-1-carbonyl)-3-(4-methyltetrahydro-2H-pyran-4-yl)acrylonitrile | 581.3 |
| 54 | (R)-2-(3-(8-amino-1-(4-phenoxyphenyl)imidazo[1,5-a]pyrazin-3-yl)piperidine-1-carbonyl)-3-(4-methyltetrahydro-2H-pyran-4-yl)acrylonitrile | 563.3 |
| 55 | (R)-2-(3-(8-amino-1-(2-fluoro-4-phenoxyphenyl)imidazo[1,5-a]pyrazin-3-yl)piperidine-1-carbonyl)-4-methyl-4-(4-(3-methyloxetan-3-yl)piperazin-1-yl)pent-2-enenitrile | 680.3 |
| 56 | (R)-methyl 4-(5-(3-(8-amino-1-(4-phenoxyphenyl)imidazo[1,5-a]pyrazin-3-yl)piperidin-1-yl)-4-cyano-2-methyl-5-oxopent-3-en-2-yl)piperazine-1-carboxylate | 649.3 |
| 57 | (R)-4-(4-acetylpiperazin-1-yl)-2-(3-(8-amino-1-(4-phenoxyphenyl)imidazo[1,5-a]pyrazin-3-yl)piperidine-1-carbonyl)-4-methylpent-2-enenitrile | 633.0 |
| 58 | (R)-methyl 4-(5-(3-(8-amino-1-(2-fluoro-4-phenoxyphenyl)imidazo[1,5-a]pyrazin-3-yl)piperidin-1-yl)-4-cyano-2-methyl-5-oxopent-3-en-2-yl)piperazine-1-carboxylate | 667.4 |
| 59 | (R)-4-(4-acetylpiperazin-1-yl)-2-(3-(8-amino-1-(2-fluoro-4-phenoxyphenyl)imidazo[1,5-a]pyrazin-3-yl)piperidine-1-carbonyl)-4-methylpent-2-enenitrile | 651.4 |
| 60 | (R)-2-(3-(8-amino-1-(2-fluoro-4-phenoxyphenyl)imidazo[1,5-a]pyrazin-3-yl)piperidine-1-carbonyl)-4,4-dimethylpent-2-enenitrile | 539.3 |
| 61 | (R)-2-(3-(8-amino-1-(4-phenoxyphenyl)imidazo[1,5-a]pyrazin-3-yl)piperidine-1-carbonyl)-4,4-dimethylpent-2-enenitrile | 521.3 |
| 62 | 2-((R)-3-(8-amino-1-(2-fluoro-4-phenoxyphenyl)imidazo[1,5-a]pyrazin-3-yl)piperidine-1-carbonyl)-4-methyl-4-((S)-6-oxohexahydropyrrolo[1,2-a]pyrazin-2(1H)-yl)pent-2-enenitrile | 663.4 |
| 63 | 2-((R)-3-(8-amino-1-(2-fluoro-4-phenoxyphenyl)imidazo[1,5-a]pyrazin-3-yl)piperidine-1-carbonyl)-4-methyl-4-((R)-6-oxohexahydropyrrolo[1,2-a]pyrazin-2(1H)-yl)pent-2-enenitrile | 663.4 |
| 64 | 2-((R)-3-(8-amino-1-(4-phenoxyphenyl)imidazo[1,5-a]pyrazin-3-yl)piperidine-1-carbonyl)-4-methyl-4-((S)-6-oxohexahydropyrrolo[1,2-a]pyrazin-2(1H)-yl)pent-2-enenitrile | 645.4 |
| 65 | 2-((R)-3-(8-amino-1-(4-phenoxyphenyl)imidazo[1,5-a]pyrazin-3-yl)piperidine-1-carbonyl)-4-methyl-4-((R)-6-oxohexahydropyrrolo[1,2-a]pyrazin-2(1H)-yl)pent-2-enenitrile | 645.4 |
| 66 | (R)-2-(3-(8-amino-1-(4-phenoxyphenyl)imidazo[1,5-a]pyrazin-3-yl)-4-methylpiperazine-1-carbonyl)-4,4-dimethylpent-2-enenitrile | 536.3 |
| 67 | (R)-2-(3-(8-amino-1-(4-phenoxyphenyl)imidazo[1,5-a]pyrazin-3-yl)-4-methylpiperazine-1-carbonyl)-3-(4-methyltetrahydro-2H-pyran-4-yl)acrylonitrile | 578.3 |
| 68 | 2-((R)-3-(8-amino-1-(4-phenoxyphenyl)imidazo[1,5-a]pyrazin-3-yl)piperidine-1-carbonyl)-4-methyl-4-((R)-3-oxotetrahydro-1H-oxazolo[3,4-a]pyrazin-7(3H)-yl)pent-2-enenitrile | |
| 69 | 2-((R)-3-(8-amino-1-(4-phenoxyphenyl)imidazo[1,5-a]pyrazin-3-yl)piperidine-1-carbonyl)-4-methyl-4-((S)-3-oxotetrahydro-3H-oxazolo[3,4-a]pyrazin-7(1H)-yl)pent-2-enenitrile | |
| 70 | 2-((R)-3-(8-amino-1-(2-fluoro-4-phenoxyphenyl)imidazo[1,5-a]pyrazin-3-yl)piperidine-1-carbonyl)-4-methyl-4-((R)-3-oxotetrahydro-1H-oxazolo[3,4-a]pyrazin-7(3H)-yl)pent-2-enenitrile | |
| 71 | 2-((R)-3-(8-amino-1-(2-fluoro-4-phenoxyphenyl)imidazo[1,5-a]pyrazin-3-yl)piperidine-1-carbonyl)-4-methyl-4-((S)-3-oxotetrahydro-1H-oxazolo[3,4-a]pyrazin-7(3H)-yl)pent-2-enenitrile | |
| 72 | (R)-2-(3-(4-amino-3-(2-fluoro-4-phenoxyphenyl)-1H-pyrazolo[4,3-c]pyridin-1-yl)piperidine-1-carbonyl)-4-methyl-4-(4-methyl-3-oxopiperazin-1-yl)pent-2-enenitrile | 637.4 | or a stereoisomer of any of the above compounds; or an E or Z isomer thereof;

and/or a pharmaceutically acceptable salt of any of the above compounds.

EMBODIMENTS

In embodiments 1-23 below, the present disclosure includes:

1. A compound of Formula (I) is as defined in the first aspect above and/or a pharmaceutically acceptable salt thereof 2. The compound of embodiment 1 and/or a pharmaceutically acceptable salt thereof wherein X is —O— and —X—Ar is attached at the 4 position of the phenyl ring substituted with $R^1$ and $R^2$, the carbon atom of the same phenyl ring attached to G being position 1.

3. The compound of embodiment 1 and/or a pharmaceutically acceptable salt thereof wherein X is —CONR— or —NRCO—. Within embodiment 3, in one embodiment, Ar is heteroaryl or phenyl where heteroaryl and phenyl are optionally substituted with one, two, or three substituents independently selected from alkyl, halo, haloalkyl, alkoxy, and hydroxy. Within embodiment 3, in another embodiment, Ar is pyridinyl, pyrimidinyl, thienyl, or pyrazinyl, optionally substituted with one, two, or three substituents independently selected from alkyl, halo, haloalkyl, alkoxy, and hydroxy. Within embodiment 3, in yet another embodiment, Ar is phenyl where phenyl is optionally substituted with one, two, or three substituents independently selected from alkyl, halo, haloalkyl, alkoxy, and hydroxy, preferably one or two fluoro.

4. The compound of embodiment 1 and/or a pharmaceutically acceptable salt thereof wherein X is —NR—CO—NR'.

5. The compound of any one of embodiments 1-4, including embodiments therein, and/or a pharmaceutically acceptable salt thereof wherein Ar is phenyl optionally substituted with one, two, or three substituents independently selected from alkyl, halo, haloalkyl, alkoxy, and hydroxy.

6. The compound of any one of embodiments 1-4, and/or a pharmaceutically acceptable salt thereof wherein Ar is phenyl optionally substituted with one, two, or three halo.

7. The compound of any one of embodiments 1-4 and/or a pharmaceutically acceptable salt thereof wherein Ar is phenyl or 2,6-difluorophenyl.

8. The compound of any one of embodiments 1-4, including embodiments therein, and/or a pharmaceutically acceptable salt thereof wherein Ar is heteroaryl optionally substituted with one, two, or three substituents independently selected from alkyl, halo, haloalkyl, alkoxy, and hydroxy. Within embodiment 8, Ar is pyridinyl, pyrimidinyl, thienyl, or pyrazinyl, optionally substituted with one, two, or three substituents independently selected from alkyl, halo, haloalkyl, alkoxy, and hydroxy.

9. The compound of any one of embodiments 1-8, including embodiments therein, and/or a pharmaceutically acceptable salt thereof wherein —X—Ar is attached at the 4 position of the phenyl ring substituted with $R^1$ and $R^2$, and (1) both $R^1$ and $R^2$ are H, or (2) one of $R^1$ and $R^2$ is H and the other is fluoro attached at the 2-position the phenyl ring, the carbon atom of the same phenyl ring attached to G being position 1.

10. The compound of any one of embodiments 1-9, including embodiments therein, and/or a pharmaceutically acceptable salt thereof wherein:

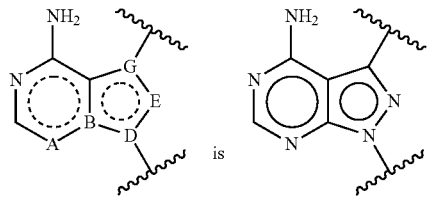

11. The compound of any one of embodiments 1-9, including embodiments therein, and/or a pharmaceutically acceptable salt thereof wherein:

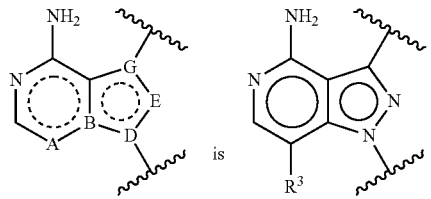

In one embodiment of embodiment 11, $R^3$ is hydrogen or halo. In another embodiment of embodiment 11, $R^3$ is hydrogen. In yet another embodiment of embodiment 11, $R^3$ is chloro or fluoro.

12. The compound of any one of embodiments 1-9, including embodiments therein, and/or a pharmaceutically acceptable salt thereof wherein:

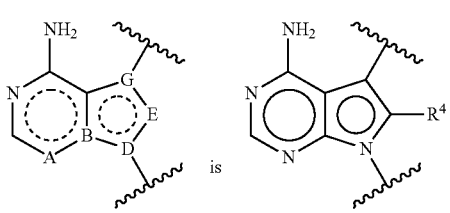

13. The compound of any one of embodiments 1-9, including embodiments therein, and/or a pharmaceutically acceptable salt thereof wherein:

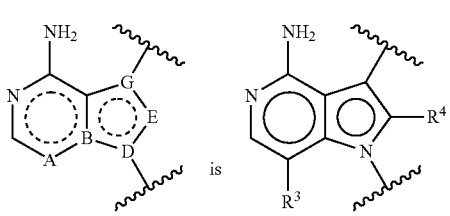

14. The compound of any one of embodiments 1-9, including embodiments therein, and/or a pharmaceutically acceptable salt thereof wherein:

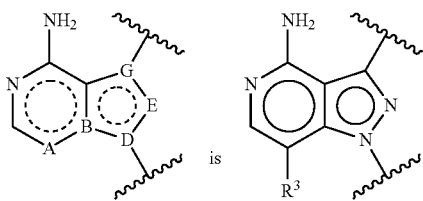

is

In one embodiment of embodiment 14, $R^3$ is hydrogen or halo. In another embodiment of embodiment 14, $R^3$ is hydrogen. In yet another embodiment of embodiment 14, $R^3$ is chloro or fluoro.

15. The compound of any one of embodiments 1-9, including embodiments therein, and/or a pharmaceutically acceptable salt thereof wherein:

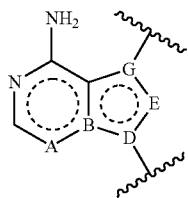

is a group of formula (vi)-(x) above.

16. The compound of any one of embodiments 1-15, including embodiments therein, and/or a pharmaceutically acceptable salt thereof wherein

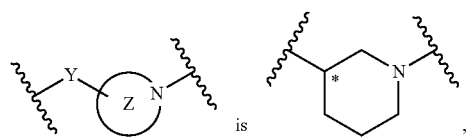

where the stereochemistry at *C is R, S or a mixture of R and S stereoisomers, preferably R.

17. The compound of any one of embodiments 1-15, including embodiments therein, and/or a pharmaceutically acceptable salt thereof wherein

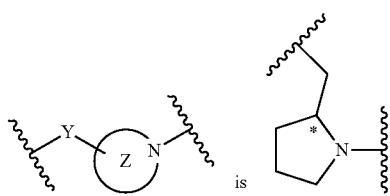

where the stereochemistry at *C is R, S or a mixture of R and S stereoisomers.

18. The compound of any one of embodiments 1-17, including embodiments therein, and/or a pharmaceutically acceptable salt thereof wherein $R^c$ is cycloalkyl. In one embodiment $R^c$ is cyclopropyl.

19. The compound of any one of embodiments 1-17, including embodiments therein, and/or a pharmaceutically acceptable salt thereof wherein $R^c$ is alkyl. In one embodiment of embodiment 19, $R^c$ is isopropyl or tert-butyl. In another embodiment of embodiment 19, $R^c$ is isopropyl.

20. The compound of any one of embodiments 1-17, including embodiments therein, and/or a pharmaceutically acceptable salt thereof wherein $R^c$ is -(alkylene)-$NR^6R^7$ (where $R^6$ and $R^7$ are independently hydrogen, alkyl, haloalkyl, hydroxyalkyl, alkoxyalkyl, cycloalkyl, or heterocyclyl. In one embodiment of embodiment 20, $R^c$ is —C(CH$_3$)$_2$NH$_2$, —C(CH$_3$)$_2$NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$N(CH$_2$CH$_3$)(oxetan-3-yl), —C(CH$_3$)$_2$N(CH$_3$)(oxetan-3-yl), or —C(CH$_3$)$_2$NH(oxetan-3-yl).

21. The compound of any one of embodiments 1-17, including embodiments therein, and/or a pharmaceutically acceptable salt thereof wherein $R^c$ is heterocyclyl optionally substituted with one, two, or three substituents where two of the optional substituents are independently selected from alkyl, alkoxy, hydroxy, halo, amino, and oxo, and one of the optional substituent is alkyl, hydroxyalkyl, alkoxyalkyl, acyl, or heterocyclyl. In one embodiment of embodiment 21, $R^c$ is oxetan-3-yl, 3-methyloxetan-3-yl, 3-ethyloxetan-3-yl, 3-fluorooxetan-3-yl, 3-aminooxetan-3-yl, 4-methylpiperidin-4-yl, 3-methylazetidin-3-yl, 1-methyl azetidin-3-yl, 4-methyl-4-tetrahydropyranyl, 4-methyl-1-(oxetan-3-yl)piperidin-4-yl, or 1,3-dimethylazetidin-3-yl, preferably methyloxetan-3-yl, 3-ethyloxetan-3-yl, 3-fluorooxetan-3-yl, 3-aminooxetan-3-yl, 4-methylpiperidin-4-yl, 3-methylazetidin-3-yl, 1-methylazetidin-3-yl, 4-methyltetrahydro-2H-pyran-4-yl, 4-methyl-4-tetrahydropyranyl or 1,3-dimethylazetidin-3-yl.

22. The compound of any one of embodiments 1-17, including embodiments therein, and/or a pharmaceutically acceptable salt thereof wherein $R^c$ is heterocyclylalkyl wherein the heterocyclyl in heterocyclylalkyl is optionally substituted with one, two, or three substituents where two of the optional substituents are independently selected from alkyl, alkoxy, hydroxy, halo, amino, and oxo, and one of the optional substituent is alkyl, hydroxyalkyl, alkoxyalkyl, acyl, haloalkyl, alkylsulfonyl, alkoxycarbonyl, or heterocyclyl wherein the heterocyclyl is optionally substituted with one or two substitutents independently selected from alkyl, halo, hydroxy, and alkoxy. In one embodiment of embodiment 22, $R^c$ is

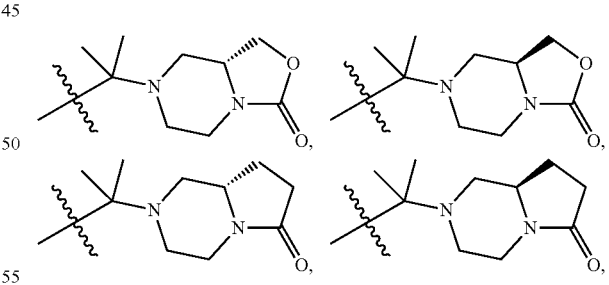

—C(CH$_3$)$_2$morpholin-4-yl, —C(CH$_3$)$_2$tetrahydropyran-4-yl, —C(CH$_3$)$_2$-4-methoxycarbonyl-piperazin-1-yl, —C(CH$_3$)$_2$-4-(oxetan-4-yl)piperazin-1-yl, —C(CH$_3$)$_2$-4-(oxetan-3-yl)piperazin-1-yl, —C(CH$_3$)$_2$-4-(3-methyloxetan-4-yl)piperazin-1-yl, —C(CH$_3$)$_2$-4-(3-methyloxetan-3-yl)piperazin-1-yl, —C(CH$_3$)$_2$-4-methoxycarbonylpiperazin-1-yl, —C(CH$_3$)$_2$-4-methylpiperazin-1-yl, —C(CH$_3$)$_2$-4-ethylpiperazin-1-yl, —C(CH$_3$)$_2$-4-isopropylpiperazin-1-yl, —C(CH$_3$)$_2$-4-(2-methoxyethyl)piperazin-1-yl, —C(CH$_3$)$_2$-4-acetylpiperazin-1-yl, —C(CH$_3$)$_2$-4-(3R,5S)-3,4,5-trimethylpiperazin-1-yl, —C(CH$_3$)$_2$-4-(3R,5S)-dimethylmorpholin-4-yl, —C(CH₃)₂-piperidin-1-yl, —C(CH₃)₂-3-oxo-piperazin-1-yl, —C(CH₃)₂-(3-oxo-4-ethylpiperazin-1-yl) or —C(CH₃)₂-(3-oxo-4-methylpiperazin-1-yl), preferably R$^c$ is —C(CH₃)₂-4-(oxetan-4-yl)piperazin-1-yl or —C(CH₃)₂-4-(oxetan-3-yl)piperazin-1-yl. In another embodiment of embodiment 22, R$^c$ is heterocyclylalkyl wherein the heterocyclyl in heterocyclylalkyl is substituted with heterocyclyl that is substituted with alkyl on the carbon that is attached to the heterocyclyl ring of heterocyclylalkyl group, preferably R$^c$ is —C(CH₃)₂-4-(3-methyloxetan-4-yl)piperazin-1-yl, or —C(CH₃)₂-4-(3-methyloxetan-3-yl)piperazin-1-yl.

23. A compound listed in Table I and/or a pharmaceutically acceptable salt thereof, including enantiomer or diastereomer thereof if the compound has at least one chiral center, a mixture of the compound and enantiomer or diastereomer thereof if the compound has at least one chiral center, individual E or Z isomer thereof, and a mixture of E and Z isomer thereof.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., or from about 0° C. to about 125° C. or at about room (or ambient) temperature, e.g., about 20° C.

Compounds of Formula (I) wherein

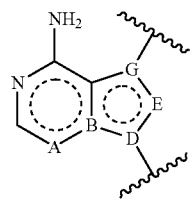

is a group of formula (i), (ii), (iii), or (iv) can be prepared as described in Scheme 1 below.

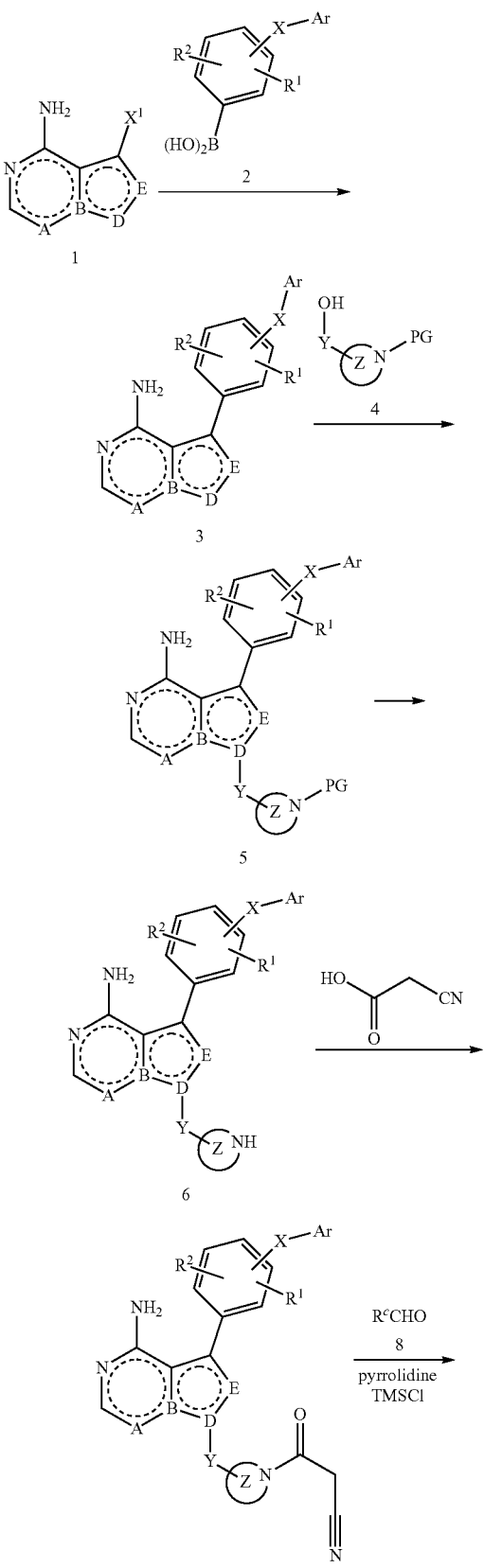

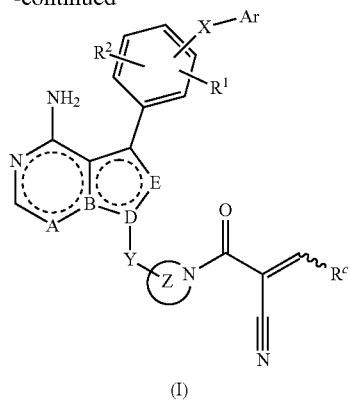

Synthetic precursors useful in Scheme 1 include 3-bromo-1H-pyrrolo[3,2-c]pyridin-4-amine [CASRN 1256813-45-2], 3-iodo-1H-pyrazolo[4,3-c]pyridin-4-amine [CASRN 14351479-27-0], 5-bromo-7H-pyrrolo[2,3-d]pyrimidin-4-amine [CASRN 22276-99-9] and 3-iodo-1H-pyrazolo[3,4-d]pyrimidin-4-amine [570409-85-7] and are commercially available or can be prepared from commercially available precursors. Intermediate of formula 1 wherein $X^1$=H can be halogenated at the 3-position with N-bromo- or N-iodo-succinimide if required. A compound of Formula (I) where

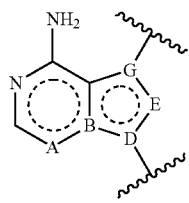

is a group of formula (ii) can also be prepared from commercially available 4-chloro-3-iodo-1H-pyrazolo[4,3-c]pyridine [CASRN 1186647-69-7] by treating it with a solution of ammonia in water or an organic solvent such as methanol. Alternatively the amine group can be installed by sequential displacement of chloride with dimethoxy-benzylamine followed by debenzylation by treatment with trifluoroacetic acid. Treatment of compound of formula 1 with a compound of formula 2, where Ar, X, $R^1$ and $R^2$ are as defined in the Summary, under Suzuki-Miyama coupling conditions provides a compound of formula 3. The coupling is conveniently carried out in a solvent such as toluene, dioxane, dimethoxyethane or tetrahydrofuran using a suitable catalyst, for example, bis-(tri-o-tolylphosphine)-palladium-(II)-chloride, tris-(dibenzylideneacetone)-dipalladium (0)/tris-o-tolylphosphine, tris-(dibenzylideneacetone)-dipalladium(0)/tris-(2-furyl)phosphan, tris-(dibenzylideneacetone)-dipalladium(1)/2,2'-bis-(diphenylphosphino)-1-,1'-binaphthyl, tetrakis-(triphenylphosphine)-palladium(0), 1,1'-bis-(diphenylphosphino)-ferrocene-palladium-dichloride or Pd(II)(OAc)$_2$/1,3-bis-(triphenylphosphino)-propane, preferably in the presence of a base such as sodium-tert-butoxide, bis-(trimethylsilyl)-lithium amide, potassium carbonate, cesium carbonate or triethylamine at a temperature between 0 and 150° C., preferably 20 to 100° C. Optimal protocols for a specific Suzuki-Miyama coupling can readily identified by one skilled in the art Compounds of formula 3 can be coupled with an alcohol of formula 4 where Y and ring Z are as defined in the Summary and PG is a suitable nitrogen protecting group, under Mitsunobu conditions to afford a compound of formula 5. Compounds of formula 4 such as tert-butyl 3-hydroxypiperidine-1-carboxylate [CASRN85275-45-2], tert-butyl 4-hydroxypiperidine-1-carboxylate [CASRN 109384-19-2], tert-butyl 3-hydroxyazetidine-1-carboxylate [CASRN 141699-55-7], tert-butyl 3-hydroxyazepane-1-carboxylate {[CASRN 478841-10-0] or tert-butyl 4-hydroxyazepane-1-carboxylate [CASRN478832-21-2] are commercially available. Alcohols of formula 4 wherein in Y is $CH_2$ also can be prepared by reduction of an ester such as 1-(tert-butyl) 2-methyl pyrrolidine-1,2-dicarboxylate [CASRN 145681-01-2] or 1-(tert-butyl) 3-methyl pyrrolidine-1,3-dicarboxylate [CASRN 122684-33-7] with LiAlH$_4$. One skilled in the art will appreciate that when stereoisomerism is possible both racemates and the R- and S-isomers are readily obtainable and may be used. Mitsunobu conditions (D. L. Hughes, The Mitsunobu Reaction, in *Organic Reactions*, Volume 42, 1992, John Wiley & Sons, New York; pp. 335-656) comprise activating alcohols with a mixture of a phosphine such as a trialkylphosphine like tributylphosphine ((n-Bu)$_3$P), a triphenylphosphine (Ph$_3$P) and the like and diethyl-azodicarboxylate (DEAD), diisopropyl-azodicarboxylate (DIAD) or di-tert-butyl-azodicarboxylate in an inert solvent such as THF, toluene, DCM.

Alternatively compounds of formula 4 can be converted to the corresponding mesylate which can be displaced by compounds formula 3 to afford compounds of formula 5. Mesylates of compounds 4 can be prepared by mesylation of the alcohols. Removal of the amino protecting group provides a compound of formula 6. When the PG is a Boc group, deprotection with an acid such as HCl or TFA affords compound 6. The trifluoroacetamide is deprotected with NaOH.

Acylation of compound 6 with cyanoacetic acid affords compound 7. Acylations can be carried out by activation of a carboxylic acid with 1-[3-(dimethylamino)propyl]-3-ethylcarbodiimide hydrochloride (ECM), 1,1'-carbonyldiimidazole (CDI) or 1,3-dicyclohexylcarbodiimide (DCC) and 1-hydroxy-7-azabenzotriazole (HOAt) or 1-hydroxybenzotriazole hydrate (HOBO, and reacted with the amine in the presence of a base, e.g. triethylamine, in a solvent such as THF, dichloromethane or toluene. One skilled in the art will appreciate there are many alternatives to the reagents identified above which activate a carboxylic acid in like manner. These reactions are typically run at a moderately reduced temperature between about −10 to +10° C. and are typically complete in several hours. The product is recovered by conventional means. Acylation of amines has been reviewed (J. March, *Advanced Organic Chemistry*, pp. 417-425; H. G. Benz, *Synthesis of Amides and Related Compounds in Comprehensive Organic Synthesis*, E. Winterfeldt, ed., vol. 6, Pergamon Press, Oxford 1991 pp. 381-411).

Reacting compound 7 with an aldehyde of formula 8 where $R^c$ is as defined in the Summary or a precursor group thereof in the presence of TMSCl or by methods described in the art, such as WO2014/039899 provides compound of Formula (I).

Compounds of Formula (I) wherein

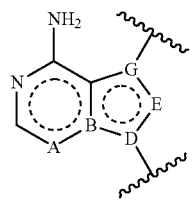

is a group of formula (v) or (vi) can be prepared as described in Scheme 2 below.

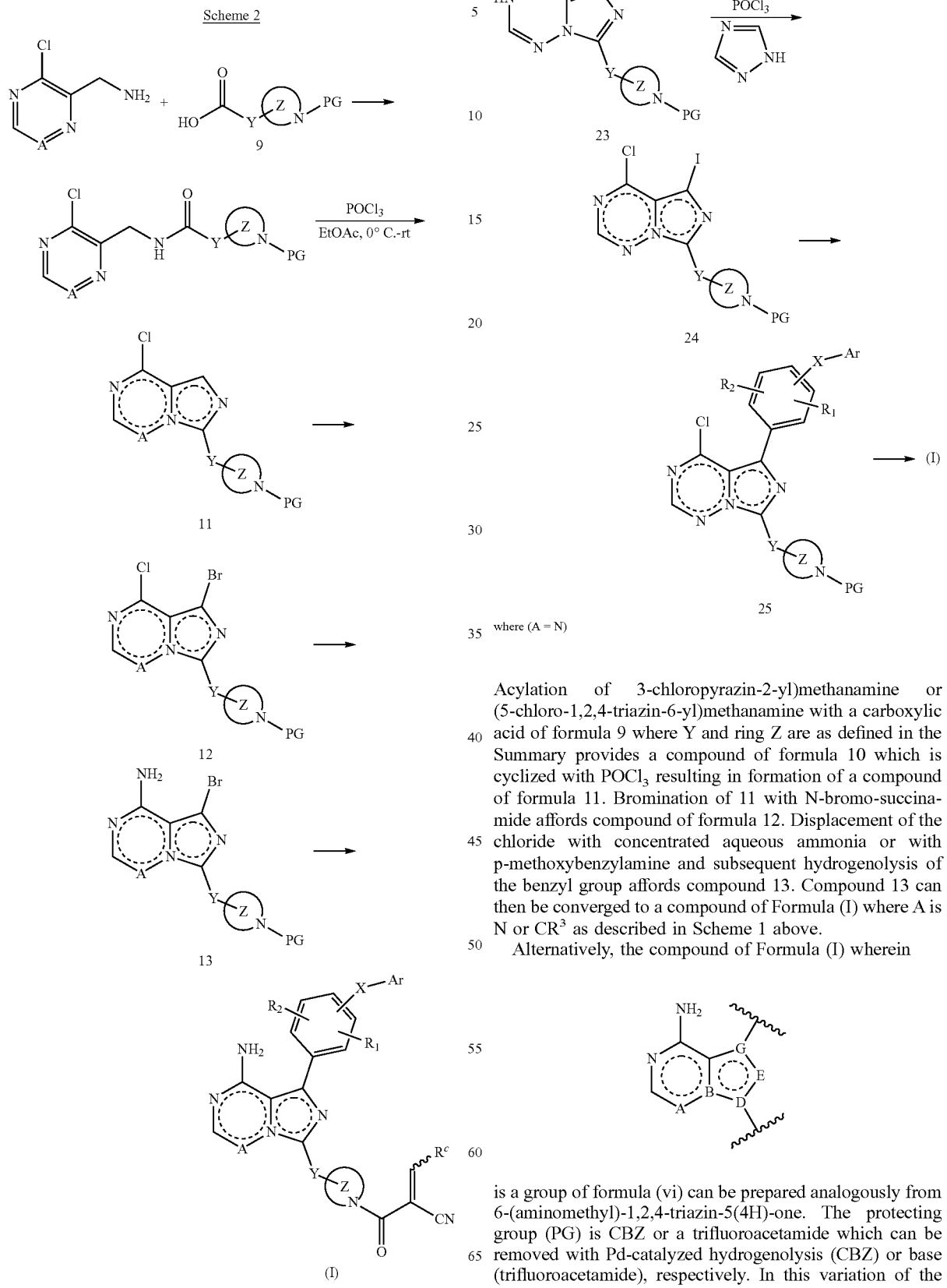

where (A = N)

Acylation of 3-chloropyrazin-2-yl)methanamine or (5-chloro-1,2,4-triazin-6-yl)methanamine with a carboxylic acid of formula 9 where Y and ring Z are as defined in the Summary provides a compound of formula 10 which is cyclized with POCl₃ resulting in formation of a compound of formula 11. Bromination of 11 with N-bromo-succinamide affords compound of formula 12. Displacement of the chloride with concentrated aqueous ammonia or with p-methoxybenzylamine and subsequent hydrogenolysis of the benzyl group affords compound 13. Compound 13 can then be converged to a compound of Formula (I) where A is N or $CR^3$ as described in Scheme 1 above.

Alternatively, the compound of Formula (I) wherein is a group of formula (vi) can be prepared analogously from 6-(aminomethyl)-1,2,4-triazin-5(4H)-one. The protecting group (PG) is CBZ or a trifluoroacetamide which can be removed with Pd-catalyzed hydrogenolysis (CBZ) or base (trifluoroacetamide), respectively. In this variation of the general scheme, the 4-amino substituent is introduced by treating the iodo lactam 23 with 1H-1,2,4 triazole in acetonitrile, POCl$_3$ and Et$_3$N and to afford compound 24. After palladium catalyzed arylation as described above, displacement of the chloride in 25 is accomplished by heating compound 25 with a solution of ammonia in water or an alcohol such as methanol, ethanol, or isopropanol, or by displacement with dimethoxybenzylamine followed by treatment with trifluoroacetic acid to introduce the 4-amino substituent. Deprotection of the PG affords the amine which can be converted to a substituted cyanoacrylamide as described in Scheme 1 above.

Compounds of Formula (I) wherein

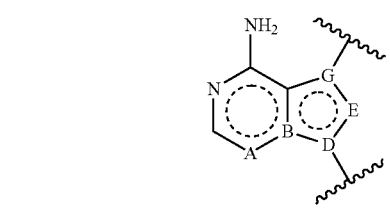

is a group of formula (viii) can be prepared as described in Scheme 3 below.

Scheme 3

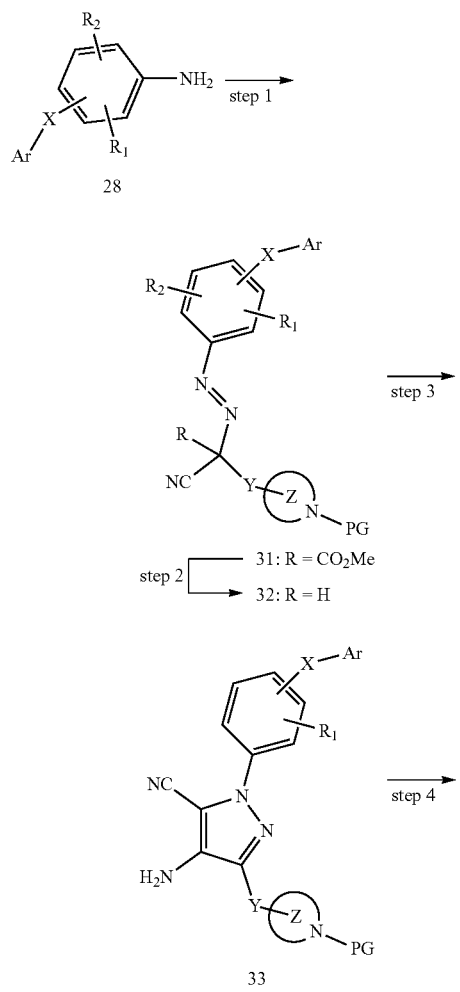

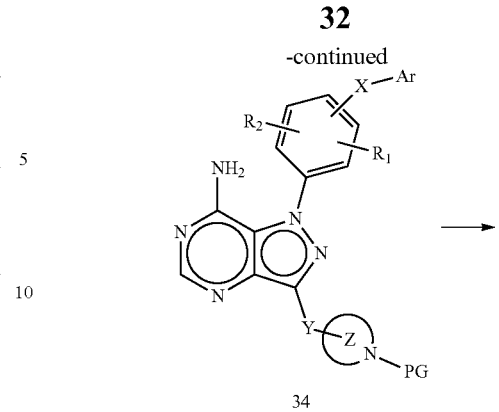

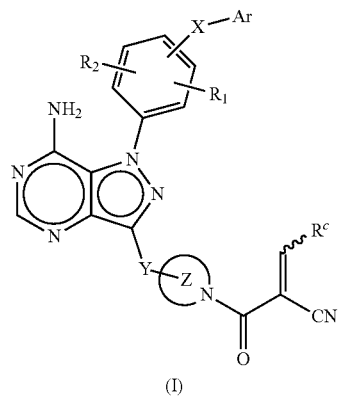

(1) (i) HNO$_3$, (ii) MeO$_2$C(CN)HC—Y—Z N—PG;
(2) NaOH; (3) BrCH$_2$CN; (4) formamidine acetate;

Diazotization of the aniline 28 where R$^1$, R$^2$, X, and Ar are as defined in the Summary, in HNO$_3$ and reacting the diazonium salt with a suitable cyanoacetate derivative affords a diazene of formula 31. Hydrolysis and decarboxylation of 31 affords 32 which can be cyclized with bromoacetonitrile in tert butanol in the presence of sodium tert-butoxide to afford the pyrazole 33. Reaction of 33 with formamidine acetate at 80° C. affords an 1-aryl-1H-pyrazolo[4,3-d]pyrimidine of formula 34. Compound 34 can then be converted to a compound of Formula (I) as described in Scheme 1 above.

Testing

The BTK inhibitory activity of the compounds of the present disclosure can be tested using the in vitro and/or in vivo assays described in Biological Examples 1-4 below. A determination of kinase inhibitory activity by any of those assays is considered to be kinase inhibitory activity within the scope of this disclosure even if any or all of the other assays do not result in a determination of kinase inhibitory activity.

The ability of the compound of the disclosure to form reversible covalent bond with Cys481 of BTK (UniprotKB Sequence ID Q06187), can be determined by the assays described in Examples 5-8 below.

Without being bound to any specific mechanistic theory, in those embodiments wherein the compound of the present disclosure is a reversible covalent inhibitor, it is believed that the cysteine sulfhydryl group and a carbon atom forming part of the carbon-carbon double bond in the group —COC(CN)=CHR$^c$ (i.e. olefin) of the compound of the present disclosure can form a reversible, i.e., labile, covalent bond, defined herein, such as wherein Cys 481 attacks an electron deficient carbon atom of the carbon-carbon double bond in the group —C(CN)=CHR$^c$ in the compound of present disclosure to form a labile thiol adduct (e.g., Michael reaction with cysteine).

In some embodiments, the electron deficient carbon atom of the olefin is distal to the carbon attached to the cyano group and to the electron withdrawing —Z—CO— moiety (see Formula I) in the compounds of the present disclosure. Therefore, the combination of the cyano and the "—CO—" moieties and the olefinic moiety to which they are bonded in the compounds of the present disclosure can increase the reactivity of the olefin to form a thiol adduct with the active site cysteine residue in BTK.

Accordingly, the compounds of the present disclosure bind with BTK in two different manner. In addition to the labile covalent binding, discussed above, they also form non-covalent binding (e.g., via van der Waals binding, hydrogen binding, hydrophobic binding, hydrophilic binding, and/or electrostatic charge binding) with BTK, the non-covalent binding being sufficient to at least partially inhibit the kinase activity of the BTK.

As disclosed herein, the labile covalent binding between the compound of the disclosure and BTK occurs between the olefin in the inhibitor and the cysteine 481 residue thiol side chain at or near the site where the compound has the aforementioned non-covalent binding with the BTK.

As is evident, the compounds of the present disclosure which are reversible covalent inhibitors have both a cysteine-mediated covalent binding and a non-covalent binding with the BTK. This is in contrast with non-covalent reversible inhibitors which inhibit the BTK only via non-covalent binding and lack the cysteine-mediated covalent binding.

The result of the binding of the compounds of the present disclosure with BTK in the two different manners provides a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved an inhibitor that forms a reversible covalent bond with BTK, i.e., the compounds disclosed herein, is stable when the BTK is in certain configurations and susceptible to being broken when the BTK is in different configurations (in both cases under physiologic conditions), whereas the interaction between an inhibitor that forms an irreversible covalent bond with BTK is stable under physiologic conditions even when the BTK is in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drug-target residence time and its implications for lead optimization. *Nat. Rev. Drug Discov.* 5(9), 730-739 (2006).

The presence of a reversible covalent bond in a reversible covalent inhibitor as disclosed herein can lead to an extended residence time when compared to a compound that does not form a covalent bond with BTK. In one embodiment disclosed herein the compounds of the present disclosure that are reversible covalent inhibitors have a residence time of at least about 1 h, residence time may be measured using an occupancy assay in a biochemical or cellular environment (see Biological Example 2 below). Additionally, residence time may be measured using a functional assay following a defined wash-out period.

Compounds that form an irreversible covalent bond in an irreversible covalent inhibitor share these extended residence time properties but may nonetheless be differentiated from a reversible covalent inhibitor using a reversibility assay. The ability of the compound of the disclosure to form reversible covalent bond with BTK (UniprotKB Sequence ID Q06187), can be determined by the assays described in Biological Examples 2, 6, 7, or 8 below. A determination of the binding reversibility of the covalent bond between the cysteine residue and the olefinic bond of the compound of the disclosure by any of Biological Examples 2 and 6-8 below is considered to be binding reversibility within the scope of this disclosure even if one or more of the other methods does not result in a determination of binding reversibility.

Administration and Pharmaceutical Composition

In general, the compounds of this disclosure will be administered in a therapeutically effective amount by any of the accepted modes of administration for agents that serve similar utilities. Therapeutically effective amounts of compounds of Formula (I) and/or a pharmaceutically acceptable salt thereof may range from about 0.01 to about 500 mg per kg patient body weight per day, which can be administered in single or multiple doses. In one embodiment, the dosage level will be about 0.1 to about 250 mg/kg per day. In another embodiment about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions may be provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. Bioavailability of drugs that decompose at stomach pH can be increased by administration of such drugs in a formulation that releases the drug intraduodenally.

The compositions are comprised of in general, a compound of Formula (I) and/or a pharmaceutically acceptable salt thereof in combination with a pharmaceutically acceptable excipient such as binders, surfactants, diluents, buffering agents, antiadherents, glidants, hydrophilic or hydrophobic polymers, retardants, stabilizing agents or stabilizers, disintegrants or superdisintegrants, antioxidants, antifoaming agents, fillers, flavors, colors, lubricants, sorbents, preservatives, plasticizers, or sweeteners, or mixtures thereof, which facilitate processing of the compound of Formula (I) (or embodiments thereof disclosed herein) and/or a pharmaceutically acceptable salt thereof into preparations which can be used pharmaceutically. Any of the well-known techniques and excipients may be used as suitable and as understood in the art, see for example, Remington: The Science and Practice of Pharmacy, Twenty-first Ed., (Pharmaceutical Press, 2005); Liberman, H. A., Lachman, L., and Schwartz, J. B. Eds., Pharmaceutical Dosage Forms, Vol. 1-2 Taylor & Francis 1990; and R. I. Mahato, Ansel's Pharmaceutical Dosage Forms and Drug Delivery Systems, Second Ed. (Taylor & Francis, 2012).

In certain embodiments, the formulations may include one or more pH adjusting agents or buffering agents, for example, acids such as acetic, boric, citric, fumaric, maleic, tartaric, malic, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate, ammonium chloride, and the like. Such buffers used as bases may have other counterions than sodium, for example, potassium, magnesium, calcium, ammonium, or other counterions. Such acids, bases and buffers are included in an amount required to maintain pH of the composition in an acceptable range.

In certain embodiments, the formulations may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments, the formulations may also include one or more antifoaming agents to reduce foaming during processing which can result in coagulation of aqueous dispersions, bubbles in the finished film, or generally impair processing. Exemplary anti-foaming agents include silicon emulsions or sorbitan sesquioleate.

In certain embodiments, the formulations may also include one or more antioxidants, such as non-thiol antioxidants, for example, butylated hydroxytoluene (BHT), sodium ascorbate, ascorbic acid or its derivative, and tocopherol or its derivatives. In certain embodiments, antioxidants enhance chemical stability where required. Other agents such as citric acid or citrate salts or EDTA may also be added to slow oxidation.

In certain embodiments, the formulations may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide, and cetylpyridinium chloride.

In certain embodiments, the formulations may also include one or more binders. Binders impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinyl-pyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum mucilage of isapol husks, polyvinylpyrrolidone (e.g., Polyvidone® CL, Kollidon® CL, Polyplasdone® XL-10), larch arabogalactan, Veegum®, polyethylene glycol, polyethylene oxide, waxes, sodium alginate, and the like.

In certain embodiments, the formulations may also include dispersing agents and/or viscosity modulating agents. Dispersing agents and/or viscosity modulating agents include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, H-PC-SL, and HPC-L), hydroxypropyl methylcelluloses (e.g., HPMC K100, RPMC K4M, HPMC K15M, and HPMC K100M), carboxymethylcellulose sodium, methylcellulose, hydroxyethylcellulose, hydroxypropyl-cellulose, hydroxypropylmethylcellulose phthalate, hydroxypropylmethylcellulose acetate stearate (HPMCAS), non-crystalline cellulose, polyethylene oxides, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F10®8, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate. In general, binder levels of about 10 to about 70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 90% and more typically up to 70% in tablet formulations is common.

In certain embodiments, the formulations may also include one or more diluents which refer to chemical compounds that are used to dilute the compound of interest prior to delivery. Diluents can also be used to stabilize compounds because they can provide a more stable environment Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In certain embodiments, the formulations may also include one or more disintegrant which includes both the dissolution and dispersion of the dosage form when contacted with gastrointestinal fluid. Disintegration agents or disintegrants facilitate the breakup or disintegration of a substance. Examples of disintegration agents include a starch, e.g., a natural starch such as corn starch or potato starch, a pregelatinized starch such as National 1551 or sodium starch glycolate such as Promogel® or Explotab®, a cellulose such as a wood product, methylcrystalline cellulose, e.g., Avicel®, Avicel® PH101, Avicel® PH 102, Avicel® PH105, Elceme® P100, Emcocel®, Vivacel®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In certain embodiments, the formulations may also include erosion facilitators. Erosion facilitators include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

In certain embodiments, the formulations may also include one or more filling agents which include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In certain embodiments, the formulations may also include one or more flavoring agents and/or sweeteners e.g., acacia syrup, acesulfame K, alitame, anise, apple, aspartame, banana, Bavarian cream berry, black currant, butterscotch, calcium citrate, camphor, caramel, cherry, cherry cream chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In certain embodiments, the formulations may also include one or more lubricants and glidants which are compounds that prevent, reduce or inhibit adhesion or friction of materials. Exemplary lubricants include, e.g., stearic acid, calcium hydroxide, talc, sodium stearyl lumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, stearic acid, sodium stearates, glycerol, talc, waxes, boric acid, sodium benzoate, sodium acetate, sodium chloride, leucine, a polyethylene glycol (e.g., PEG4000) or a methoxypolyethylene glycol such as Carbowax®, sodium oleate, sodium benzoate, glyceryl behenate, polyethylene glycol, magnesium or sodium lauryl sulfate, colloidal silica such as Syloid®, Cab-O-Sil®, a starch such as corn starch, silicone oil, a surfactant, and the like.

In certain embodiments, the formulations may also include one or more plasticizers which are compounds used to soften the enteric or delayed release coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl citrate, dibutyl sebacate, triethyl cellulose and triacetin. In some embodiments, plasticizers can also function as dispersing agents or wetting agents.

In certain embodiments, the formulations may also include one or more solubilizers which include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins for example Captisol®, ethanol, n-butanol, isopropyl alcohol, cholesterol, bile salts, polyethylene glycol 200-600, glycofurol, transcutol, propylene glycol, and dimethyl isosorbide and the like. In one embodiment, the solubilizer is vitamin E TPGS and/or Captisol® or β-hydroxypropylcyclodextrin.

In certain embodiments, the formulations may also include one or more suspending agents which include compounds such as polyvinylpyrrolidone, e.g., polyvinylpyrrolidone K112, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gun, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monoleate, povidone and the like.

In certain embodiments, the formulations may also include one or more surfactants which include compounds such as sodium lauryl sulfate, sodium docusate, Tween 20, 60 or 80, triacetin, vitamin E TPGS, sorbitan monooleate, polyoxyethylene sorbitan monooleate, polyoxyethylene sorbitan monolaurate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g. octoxynol 10, octoxynol 40. In some embodiments, surfactants may be included to enhance physical stability or for other purposes.

In certain embodiments, the formulations may also include one or more viscosity enhancing agents which include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol alginates, acacia, chitosans and combinations thereof.

In certain embodiments, the formulations may also include one or more wetting agents which include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Pharmaceutical preparations disclosed herein can be obtained by mixing one or more solid excipient such as carrier, binder, filling agent, suspending agent, flavoring agent, sweetening agent, disintegrating agent, dispersing agent, surfactant, lubricant, colorant diluent, solubilizer, moistening agent, plasticizer, stabilizer, penetration enhancer, wetting agent, anti-foaming agent, antioxidant, preservative, or one or more combination thereof with one or more of the compounds described herein, optionally grinding the resulting mixture, and processing the mixture of granules, after adding suitable excipients, if desired, to obtain tablets.

Pharmaceutical preparations disclosed herein also include capsules made of gelatin, as well as soft, sealed capsules made of gelatin and a plasticizer, such as glycerol or sorbitol. Capsules may also be made of polymers such as hypromellose. The capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, lipids, solubilizers, or liquid polyethylene glycols. In addition, stabilizers may be added. All formulations for oral administration should be in dosages suitable for such administration.

These formulations can be manufactured by conventional pharmacological techniques. Conventional pharmacological techniques include, e.g., one or a combination of methods: (1) dry mixing, (2) direct compression, (3) milling, (4) dry or non-aqueous granulation, (5) wet granulation, (6) fusion, or (7) extrusion. See, e.g., Lachman et al., The Theory and Practice of Industrial Pharmacy, $3^{rd}$ ed. (1986). Other methods include, e.g., spray drying, pan coating, melt granulation, granulation, fluidized bed spray drying or coating (e.g., wurster coating), tangential coating, top spraying, tableting, extruding, extrusion/spheronization, and the like.

It should be appreciated that there is considerable overlap between excipients used in the solid dosage forms described herein. Thus, the above-listed additives should be taken as merely exemplary, and not limiting, of the types of excipient that can be included in solid dosage forms described herein. The type and amounts of such excipient can be readily determined by one skilled in the art, according to the particular properties desired.

In some embodiments, the solid dosage forms described herein are enteric coated oral dosage forms, i.e., as an oral dosage form of a pharmaceutical composition as described herein which utilizes an enteric coating to effect the release of the compound in the intestine of the gastrointestinal tract. An "enterically coated" drug and/or tablet refers to a drug and/or tablet that is coated with a substance that remains intact in the stomach but dissolves and releases the drug once the intestine (in one embodiment small intestine) is reached. As used herein "enteric coating", is a material, such as a polymer material or materials which encase the therapeutically active agent core either as a dosage form or as particles. Typically, a substantial amount or all of the enteric coating material is dissolved before the therapeutically active agent is released from the dosage form, so as to achieve delayed dissolution of the therapeutically active agent core or particles in the small and/or large intestine. Enteric coatings are discussed, for example, Loyd, V. Allen, Remington: The Science and Practice of Pharmacy, Twenty-first Ed., (Pharmaceutical. Press, 2005; and P. J. Tarcha, Polymers for Controlled Drug Delivery, Chapter 3, CRC Press, 1991. Methods for applying enteric coatings to pharmaceutical compositions are well known in the art, and include for example, U.S. Patent Publication No. 2006/0045822.

The enteric coated dosage form may be a compressed or molded or extruded tablet (coated or uncoated) containing granules, powder, pellets, beads or particles of the compound of Formula (I) (or any embodiments thereof) and/or a pharmaceutically acceptable salt thereof and/or other excipients, which are themselves coated or uncoated provided at least the tablet or the compound of Formula (I) and/or a pharmaceutically acceptable salt thereof is coated. The enteric coated oral dosage form may also be a capsule (coated or uncoated) containing pellets, beads or granules of the compound of Formula (I) (or any embodiments thereof) and/or a pharmaceutically acceptable salt thereof and/or other excipients, which are themselves coated or uncoated provided at least one of them is coated. Some examples of coatings that were originally used as enteric coatings are beeswax and glyceryl monostearate; beeswax, shellac and cellulose; and cetyl alcohol, mastic and shellac as well as shellac and stearic acid (U.S. Pat. No. 2,809,918); polyvinylacetate and ethyl cellulose (U.S. Pat. No. 3,835,221), More recently, the coatings used are neutral copolymers of polymethacrylic acid esters (Eudragit L30D). (F. W. Goodhart et al, Pharm. Tech., p. 64-71, April, 1984); copolymers of methacrylic acid and methacrylic acid methyl ester (Eudragit S), or a neutral copolymer of polymethacrylic acid esters containing metallic stearates (Mehta et al U.S. Pat. Nos. 4,728,512 and 4,794,001), cellulose acetate succinate, and hypromellose phthalate.

Any anionic polymer exhibiting a pH-dependent solubility profile can be used as an enteric coating in the methods and compositions described herein to achieve delivery to the intestine. In one embodiment, delivery to the small intestine. In another embodiment, delivery to the duodenum. In some embodiments the polymers described herein are anionic carboxylic polymers. In other embodiments, the polymers and compatible mixtures thereof, and some of their properties, include, but are not limited to:

Shellac:
Also called purified lac, it is a refined product obtained from the resinous secretion of an insect. This coating dissolves in media of pH>7;

Acrylic Polymers:
The performance of acrylic polymers (primarily their solubility in biological fluids) can vary based on the degree and type of substitution. Examples of suitable acrylic polymers include methacrylic acid copolymers and ammonium methacrylate copolymers. The Eudragit series L, S, and RS (manufactured Rohm Pharma and known as Evonik®) are available as solubilized in organic solvent, aqueous dispersion, or dry powders. The Eudragit series RL, NE, and RS are insoluble in the gastrointestinal tract but are permeable and are used primarily for colonic targeting. The Eudragit series L, L-30D and S are insoluble in stomach and dissolve in the intestine and may be selected and formulated to dissolve at a value of pH greater than 5.5 or as low as greater than 5 or as high as greater than 7.

Cellulose Derivatives:
Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP pseudolatex with particles <1 μm. Other components in Aquateric can include pluronics, Tweens, and acetylated monoglycerides. Other suitable cellulose derivatives include; cellulose acetate tritnellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (HPMCAS e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP):
PVAP dissolves in pH>5, and it is much less permeable to water vapor and gastric fluids. Detailed description of above polymers and their pH-dependent solubility can be found at in the article titled "Enteric coated hard gelatin capsules" by Professor Karl Thoma and Karoline Bechtold at http://pop.www.capsugel.com/media/library/enteric-coated-hard-gelatin-capsules.pdf. In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as fluid bed or Wurster coaters, or spray or pan coating are employed to apply coatings. The coating thickness must be sufficient to ensure that the oral dosage form remains intact until the desired site of topical delivery in the intestinal tract is reached.

Colorants, surfactants, anti-adhesion agents, antifoaming agents, lubricants (e.g., carnuba wax or PEG) and other additives may be added to the coatings besides plasticizers to solubilize or disperse the coating material, and to improve coating performance and the coated product.

To accelerate the dissolution of the enteric coat, a half-thickness, double coat of enteric polymer (for instance, Eudragit L30 D-55) may be applied, and the inner enteric coat may have a buffer up to pH 6.0 in the presence of 10% citric acid, followed by a final layer of standard Eudragit L 30 D-55. Applying two layers of enteric coat, each half the thickness of a typical enteric coat, Liu and Basit were able to accelerate enteric coating dissolution compared to a similar coating system applied, unbuffered, as a single layer (Liu, F. and Basit, A. Journal of Controlled Release. 147 (2010) 242-245.)

The intactness of the enteric coating may be measured, for example, by the degradation of the drug within the micropellets. The enteric coated dosage forms or pellets may be tested in dissolution testing first in gastric fluid and separately in intestinal fluid as described in USP to determine its function.

The enteric coated tablets and capsules formulation containing the disclosed compounds can be made by methods well known in the art. For example, tablets containing a compound disclosed herein can be enterically coated with a coating solution containing Eudragit®, diethylphthalate, isopropyl alcohol, talc, and water using a side vented coating pan (Freund Hi-Coater).

Alternatively, a multi-unit dosage form comprising enteric-coated pellets that can be incorporated into a tablet or into a capsule can be prepared as follows.

Core Material:

The core material for the individually enteric coating layered pellets can be constituted according to different principles. Seeds layered with the active agent ((i.e., the compound of Formula (I) (including embodiments disclosed herein) and/or a pharmaceutically acceptable sale thereof), optionally mixed with alkaline substances or buffer, can be used as the core material for the further processing. The seeds which are to be layered with the active agent can be water insoluble seeds comprising different oxides, celluloses, organic polymers and other materials, alone or in mixtures or water-soluble seeds comprising different inorganic salts, sugars, non-pareils and other materials, alone or in mixtures. Further, the seeds may comprise the active agent in the form of crystals, agglomerates, compacts etc. The size of the seeds is not essential for the present invention but may vary between approximately 0.1 and 2 mm. The seeds layered with the active agent are produced either by powder or solution/suspension layering using for instance granulation or spray coating layering equipment.

Before the seeds are layered, active agent may be mixed with further components. Such components can be binders, surfactants, fillers, disintegrating agents, alkaline additives or other and/or pharmaceutically acceptable ingredients alone or in mixtures. The binders are for example polymers such as hydroxypropyl methylcellulose (HPMC), hydroxypropyl-cellulose (HPC), carboxymethylcellulose sodium, polyvinyl pyrrolidone (PVP), or sugars, starches or other pharmaceutically acceptable substances with cohesive properties. Suitable surfactants are found in the groups of pharmaceutically acceptable non-ionic or ionic surfactants such as for instance sodium lauryl sulfate.

Alternatively, the active agent optionally mixed with suitable constituents can be formulated into a core material. Said core material may be produced by extrusion/spheronization, balling or compression utilizing conventional process equipment. The size of the formulated core material is approximately between 0.1 and 4 mm and for example, between 0.1 and 2 mm. The manufactured core material can further be layered with additional ingredients comprising the active agent and/or be used for further processing.

The active agent is mixed with pharmaceutical constituents to obtain preferred handling and processing properties and a suitable concentration of the active agent in the final preparation. Pharmaceutical constituents such as fillers, binders, lubricants, disintegrating agents, surfactants and other pharmaceutically acceptable additives may be used.

Alternatively, the aforementioned core material can be prepared by using spray drying or spray congealing technique.

Enteric Coating Layer(s):

Before applying the enteric coating layer(s) onto the core material in the form of individual pellets, the pellets may optionally be covered with one or more separating layer(s) comprising pharmaceutical excipients optionally including alkaline compounds such as pH-buffering compounds. This/these separating layer(s), separate(s) the core material from the outer layers being enteric coating layer(s). This/these separating layer(s) protecting the core material of active agent should be water soluble or rapidly disintegrating in water.

A separating layer(s) can be optionally applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for the separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium, water soluble salts of enteric coating polymers and others, used alone or in mixtures. Additives such as plasticizers, colorants, pigments, fillers anti-tacking and anti-static agents, such as for instance magnesium stearate, titanium dioxide, talc and other additives may also be included into the separating layer(s).

When the optional separating layer is applied to the core material it may constitute a variable thickness. The maximum thickness of the separating layer(s) is normally only limited by processing conditions. The separating layer may serve as a diffusion barrier and may act as a pH-buffering zone. The optionally applied separating layer(s) is not essential for the invention. However, the separating layer(s) may improve the chemical stability of the active substance and/or the physical properties of the novel multiple unit tableted dosage form.

Alternatively, the separating layer may be formed in situ by a reaction between an enteric coating polymer layer applied on the core material and an alkaline reacting compound in the core material. Thus, the separating layer formed comprises a water soluble salt formed between the enteric coating layer polymer(s) and an alkaline reacting compound which is in the position to form a salt One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used, e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layers contain pharmaceutically acceptable plasticizers to obtain the desired mechanical properties, such as flexibility and hardness of the enteric coating layers. Such plasticizers are for instance, but not restricted to triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to the selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that if a tablet is desired the acid resistance of the pellets covered with enteric coating layer(s) does not decrease significantly during compression of pellets into tablets. The amount of plasticizer is usually above 5% by weight of the enteric coating layer polymer(s), such as 15-50% and further such as 20-50%. Additives such as dispersants, colorants, pigments polymers e.g. poly(ethylacrylate, methylmethacrylate), anti-tacking and anti-foaming agents may also be included into the enteric coating layer(s). Other compounds may be added to increase film thickness and to decrease diffusion of acidic gastric juices into the acid susceptible material. The maximum thickness of the applied enteric coating is normally only limited by processing conditions and the desired dissolution profile.

Over-Coating Layer:

Pellets covered with enteric coating layer(s) may optionally further be covered with one or more over-coating layer(s). The over-coating layer(s) should be water soluble or rapidly disintegrating in water. The over-coating layer(s) can be applied to the enteric coating layered pellets by coating or layering procedures in suitable equipments such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethyl cellulose, hydroxypropyl methyl cellulose, carboxymethylcellulose sodium and others, used alone or in mixtures. Additives such as plasticizers, colorants, pigments, fillers, anti-tacking and anti-static agents, such for instance magnesium stearate, titanium dioxide, talc and other additives may also be included into the over-coating layer(s). The over-coating layer may further prevent potential agglomeration of enteric coating layered pellets, further it may protect the enteric coating layer towards cracking during the compaction process and enhance the tableting process. The maximum thickness of the applied over-coating layer(s) is normally limited by processing conditions and the desired dissolution profile. The over-coating layer may also be used as a tablet film coating layer.

Enteric coating of soft gelatin capsules may contain an emulsion, oil, microemulsion, self-emulsifying system, lipid, triglycerides, polyethylene glycol, surfactants, other solubilizers and the like, and combinations thereof, to solubilize the active agent. The flexibility of the soft gelatin capsule is maintained by residual water and plasticizer. Moreover, for gelatin capsules the gelatin may be dissolved in water so that spraying must be accomplished at a rate with relatively low relative humidity such as can be accomplished in a fluid bed or Wurster. In addition, drying should be accomplished without removing the residual water or plasticizer causing cracking of the capsule shell. Commercially available blends optimized for enteric coating of soft gelatin capsules such as Instamodel EPD (Enteric Polymeric Dispersion), available from Ideal Cures, Pvt. Ltd. (Mumbai, India). On a laboratory scale enteric coated capsules may be prepared by: a) rotating capsules in a flask or dipping capsules in a solution of the gently heated enteric coating material with plasticizer at the lowest possible temperature or b) in a lab scale sprayer/fluid bed and then drying.

For aqueous active agents, it can be especially desirable to incorporate the drug in the water phase of an emulsion. Such "water-in-oil" emulsion provides a suitable biophysical environment for the drug and can provide an oil-water interface that can protect the drug from adverse effects of pH or enzymes that can degrade the drug. Additionally, such water-in-oil formulations can provide a lipid layer, which can interact favorably with lipids in cells of the body, and can increase the partition of the formulation onto the membranes of cells. Such partition can increase the absorption of drugs in such formulations into the circulation and therefore can increase the bioavailability of the drug.

In some embodiments the water-in-oil emulsion contains an oily phase composed of medium or long chain carboxylic acids or esters or alcohols thereof, a surfactant or a surface active agent, and an aqueous phase containing primarily water and the active agent.

Medium and long chain carboxylic acids are those ranging from $C_8$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocarboxylic acids. Examples of these are linoleic acid, ricinoleic acid, linolenic acid, arachidonic acid and behenolic acid. Useful branched acids include, for example, diacetyl tartaric acid. Unsaturated olefinic chains may also be hydroxylated or ethoxylated to prevent oxidation or to alter the surface properties.

Examples of long chain carboxylic acid esters include, but are not limited to, those from the group of: glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate; acetylated glycerides such as distilled acetylated monoglycerides; mixtures of propylene glycol monoesters, distilled monoglycerides, sodium steroyl lactylate and silicon dioxide; d-alpha tocopherol polyethylene glycol 1000 succinate; mixtures of mono- and di-glyceride esters such as Atmul; calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_8$-$C_{30}$ cholesterol/lavosterol esters; and sucrose long chain carboxylic acid esters. Examples of the self-emulsifying long chain carboxylic acid esters include those from the groups of stearates, pamitates, ricinoleates, oleates, behenates, ricinolenates, myristates, laurates, caprylates, and caproates. In some embodiments the oily phase may comprise a combination of 2 or more of the long chain carboxylic acids or esters or alcohols thereof. In some embodiments medium chain surfactants may be used and the oil phase may comprise a mixture of caprylic/capric triglyceride and $C_8/C_{10}$ mono-/di-glycerides of caprylic acid, glyceryl caprylate or propylene glycol monocaprylate or their mixtures.

The alcohols that can be used are exemplified by the hydroxyl forms of the carboxylic acids exemplified above and also stearyl alcohol.

Surface active agents or surfactants are long chain molecules that can accumulate at hydrophilic/hydrophobic (water/oil) interfaces and lower the surface tension at the interface. As a result they can stabilise an emulsion. In some embodiments of this invention, the surfactant may comprise: Tween® (polyoxyethylene sorbate) family of surfactants, Span® (sorbitan long chain carboxylic acid esters) family of surfactants, Pluronic® (ethylene or propylene oxide block copolymers) family of surfactants, Labrasol®, Labrafil® and Labrafac® (each polyglycolized glycerides) families of surfactants, sorbitan esters of oleate, stearate, laurate or other long chain carboxylic acids, poloxamers (polyethylene-polypropylene glycol block copolymers or Pluronic®.), other sorbitan or sucrose long chain carboxylic acid esters, mono and diglycerides, PEG derivatives of caprylic/capric triglycerides and mixtures thereof or mixture of two or more of the above. In some embodiments the surfactant phase may comprise a mixture of Polyoxyethylene (20) sorbitan monooleate (Tween 80®) and sorbitan monooleate (Span 80®).

The aqueous phase may optionally comprise the active agent suspended in water and a buffer.

In some embodiments, such emulsions are coarse emulsions, microemulsions and liquid crystal emulsions. In other embodiments such emulsion may optionally comprise a permeation enhancer. In other embodiments, spray-dried dispersions or microparticles or nanoparticles containing encapsulated microemulsion, coarse emulsion or liquid crystal can be used.

In some embodiments, the solid dosage forms described herein are non-enteric time-delayed release dosage forms. The term "non-enteric time-delayed release" as used herein refers to the delivery so that the release of the drug can be accomplished at some generally predictable location in the intestinal tract more distal to that which would have been accomplished if there had been no delayed release alterations. In some embodiments the method for delay of release is a coating that becomes permeable, dissolves, ruptures, and/or is no longer intact after a designed duration. The coating in the time-delayed release dosage forms can have a fixed time to erode after which the drug is released (suitable coating include polymeric coating such as HPMC, PEO, and the like) or has a core comprised of a superdisintegrant(s) or osmotic agent(s) or water attractant such as a salt, hydrophilic polymer, typically polyethylene oxide or an alkylcellulose, salts such as sodium chloride, magnesium chloride, sodium acetate, sodium citrate, sugar, such as glucose, lactose, or sucrose, or the like, which draw water through a semi-permeable membrane or a gas generating agent such as citric acid and sodium bicarbonate with or without an acid such as citric acid or any of the aforementioned acids incorporated in dosage forms. The semi-permeable membrane, while mostly not permeable to the drug nor the osmotic agent, is permeable to water that permeates at a near constant rate to enter the dosage form to increase the pressure and ruptures after the swelling pressure exceeds a certain threshold over a desired delay time. The permeability through this membrane of the drug should be less than $\frac{1}{10}$ than water and in one embodiment less than $\frac{1}{100}$ the water permeability. Alternatively, a membrane could become porous by leaching an aqueous extractable over a desired delay time.

Osmotic dosage forms have been described in Theeuwes U.S. Pat. No. 3,760,984, and an osmotic bursting dosage form is described in Baker U.S. Pat. No. 3,952,741. This osmotic bursting dosage form can provide a single pulse of release or multiple pulses if different devices with different timings are employed. The timing of the osmotic burst may be controlled by the choice of polymer and the thickness or the area of the semipermeable membrane surrounding the core that contains both the drug and the osmotic agent or attractant. As the pressure in the dosage form increase with additional permeated water, the membrane elongates until its breaking point, and then the drug is released. Alternatively, specific areas of rupture can be created in the membrane by having a thinner, weaker area in the membrane or by adding a weaker material to an area of the coating membrane. Some preferred polymers with high water permeabilities that may be used as semipermeable membranes are cellulose acetate, cellulose acetate butyrate, cellulose nitrate, crosslinked polyvinyl, alcohol, polyurethanes, nylon 6, nylon 6.6, and aromatic nylon. Cellulose acetate is an especially preferred polymer.

In another embodiment, the time-delayed coating that begins this delay to releasing drug after the enteric coating is at least partially dissolved is comprised of hydrophilic, erodible polymers that upon contact with water begin to gradually erode over time. Examples of such polymers include cellulose polymers and their derivatives including, but not limited to, hydroxyalkyl celluloses, hydroxymethyl cellulose, hydroxyethyl cellulose, hydroxypropyl cellulose, hydroxypropylmethyl cellulose, carboxymethylcellulose, microcrystalline cellulose; polysaccharides and their derivatives; polyalkylene oxides, such as polyethylene oxide or polyethylene glycols, particularly high molecular weight polyethylene glycols; chitosan; poly(vinyl alcohol); xanthan gum; maleic anhydride copolymers; poly(vinyl pyrrolidone); starch and starch-based polymers; maltodextrins; poly (2-ethyl-2-oxazoline); poly(ethyleneimine); polyurethane; hydrogels; crosslinked polyacrylic acids; and combinations or blends of any of the foregoing.

Some preferred erodible hydrophilic polymers suitable for forming the erodible coating are poly(ethylene oxide), hydroxypropyl methyl cellulose, and combinations of poly (ethylene oxide) and hydroxypropyl methyl cellulose. Poly (ethylene oxide) is used herein to refer to a linear polymer of unsubstituted ethylene oxide. The molecular weight of the poly(ethylene oxide) polymers can range from about $10^5$ Daltons to about $10^7$. Daltons. A preferred molecular weight range of poly(ethylene oxide) polymers is from about 2 times $10^5$ to 2 times $10^6$ Daltons and is commercially available from The Dow Chemical Company (Midland, Mich.) referred to as SENTRY® POLYOX™ water-soluble resins, NF (National Formulary) grade. When higher molecular weights of polyethylene oxide are used, other hydrophilic agents, such as salts or sugars, like glucose, sucrose, or lactose, that promote erosion or disintegration of this coating, are also included.

The time-delayed dosage form can be a mechanical pill such as an Enterion® capsule or pH sensitive capsule which can release the drug after a pre-programmed time or when it receives a signal which can be transmitted or once it leaves the stomach.

The amount of the compound of the disclosure in a formulation can vary within the full range employed by those skilled in the art. Typically, the formulation will contain, on a weight percent (wt %) basis, from about 0.01-99.99 wt % of a compound of Formula (I) based on the total formulation, with the balance being one or more suitable pharmaceutical excipients. In one embodiment, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of the present disclosure not only with one other active compound, but also with two or more other active compounds. Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore, contemporaneously or sequentially with a compound of the present disclosure. When a compound of the present disclosure is used contemporaneously with one or more other drugs, a pharmaceutical composition containing such other drugs in addition to the compound of the present disclosure is preferred. Accordingly, the pharmaceutical compositions of the present disclosure also include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used.

Where the subject is suffering from or at risk of suffering from an autoimmune disease, an inflammatory disease, or an allergy disease, a compound of Formula (I) and/or a pharmaceutically acceptable salt thereof can be used with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subject can be treated with a compound of Formula (I) and/or a pharmaceutically acceptable salt thereof in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of Formula (I) and/or a pharmaceutically acceptable salt thereof include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula (I) and/or a pharmaceutically acceptable salt thereof include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene;

sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula (I) and/or a pharmaceutically acceptable salt thereof include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazornine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula (I) and/or a pharmaceutically acceptable salt thereof include alkylating agents, antimetabolites, natural products, or hormones, e.g., nitrogen mustards (e.g., mechlorethamine, cyclophosphamide, chlorambucil, etc.), alkyl sulfonates (e.g., busulfan), nitrosoureas (e.g., carmustine, lomustine, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula (I) and/or a pharmaceutically acceptable salt thereof include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula (I) and/or a pharmaceutically acceptable salt thereof include, but are not limited to, nitrogen mustards (e.g., mechlorethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula (I) and/or a pharmaceutically acceptable salt thereof include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an BTK inhibitor compound of the disclosure include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and 11-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a compound of Formula (I) in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

EXAMPLES

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof. The ⌇ line at the alkene carbon, in the compounds below denotes that the compounds are isolated as an undefined mixture of (E) and (Z) isomers.

Intermediate 1

Synthesis of 3-iodo-1H-pyrazolo[4,3-c]pyridin-4-amine

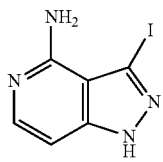 [SMILES: Nc1nccc2[nH]nc(I)c12]

Step 1

To a solution of 4-chloro-1H-pyrazolo[4,3-c]pyridine (5.5 g, 36 mmol) in DMF (50 mL) was added NIS (6.9 g, 69 mmol). The resulted mixture was stirred at 100° C. overnight. Then the mixture was cooled and diluted with water, the precipitate was collected by filtration and dried to give 4-chloro-3-iodo-1H-pyrazolo[4,3-c]pyridine (8.5 g, 85%) as a light yellow solid.

Step 2

To a solution of 4-chloro-3-iodo-1H-pyrazolo[4,3-c]pyridine (8.5 g, 30 mmol) in DMSO (100 mL) was added (2,4-dimethoxyphenyl)methanamine (15.3 g, 90 mmol). The mixture was heated at 120° C. for 3 h. The mixture was diluted EtOAc (200 mL), washed with water and brine, dried over Na₂SO₄, concentrated to afford N-(2,4-dimethoxybenzyl)-3-iodo-1H-pyrazolo[4,3-c]pyridin-4-amine (8.6 g, 70%) as a yellow oil which was used for next step without further purification.

Step 3

A mixture of N-(2,4-dimethoxybenzyl)-3-iodo-1H-pyrazolo[4,3-c]pyridin-4-amine (8.6 g, 21 mmol) in TFA (50 mL) was heated to 50° C. for 3 h. After the solvent was removed, the residue was adjusted to pH=8 with sodium bicarbonate aqueous solution and extracted with EtOAc. The organic layer was washed with brine dried over anhydrous sodium sulfate, filtered, evaporated under vacuum. The residue was purified by column chromatography to afford 3-iodo-1H-pyrazolo[4,3-c]pyridin-4-amine (4.3 g, 60%) as a white solid. MS (ESI, pos. ion) m/z: 260.7 (M+1).

Intermediate 2

Synthesis of (S)-tert-butyl 2-(((methylsulfonyl)oxy) methyl)pyrrolidine-1-carboxylate

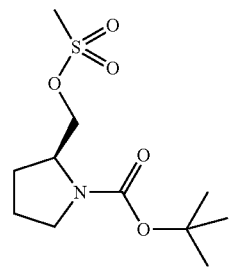 [SMILES: CC(C)(C)OC(=O)N1CCC[C@H]1COS(C)(=O)=O]

Into a 500-mL round-bottom flask, was placed (S)-tert-butyl 2-(hydroxymethyl)-pyrrolidine-1-carboxylate (16 g, 79.50 mmol, 1.00 equiv), dichloromethane (250 mL), TEA (24 g, 237.18 mmol, 3.00 equiv). This was followed by the addition of a solution of MsCl (13.78 g, 1.50 equiv) in dichloromethane (100 mL) dropwise with stirring at 0° C. over 30 min. The resulting solution was stirred for 2 h at room temperature. The reaction was then quenched by the addition of water. The resulting solution was extracted with dichloromethane and the organic layers combined. The resulting mixture was washed with brine. The mixture was dried over anhydrous sodium sulfate and concentrated under vacuum. This resulted in 20.1 g (91%) of (S)-tert-butyl 2-(((methylsulfonyl)oxy)methyl)pyrrolidine-1-carboxylate as an oil which was used without further purification.

Example 1

Synthesis 2-((S)-2-((4-amino-3-(2-fluoro-4-phenoxyphenyl)-1H-pyrazolo[4,3-c]pyridin-1-yl) methyl)pyrrolidine-1-carbonyl)-4-methyl-4-(4-methylpiperazin-1-yl)pent-2-enenitrile

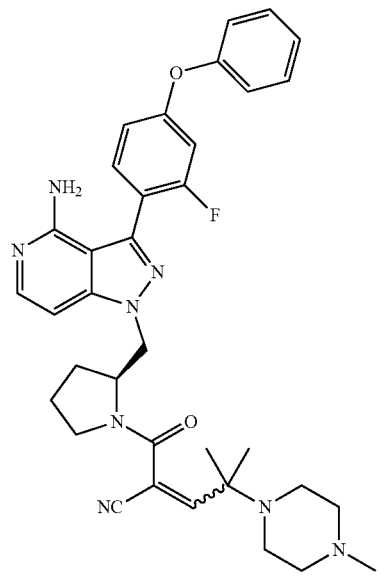 [SMILES: CN1CCN(C(C)(C)C=C(C#N)C(=O)N2CCC[C@H]2Cn2nc(-c3ccc(Oc4ccccc4)cc3F)c3c(N)nccc32)CC1]

Step 1:

A 50-mL round-bottom flask, was charged with tort-butyl (2S)-2-[(methanesulfonyl-oxy)methyl]pyrrolidine-1-carboxylate (6.44 g, 23.05 mmol, 1.50 equiv), 3-iodo-1H-pyrazolo[4,3-c]pyridin-4-amine (4 g, 15.38 mmol, 1.00 equiv), $Cs_2CO_3$ (15.05 g, 46.19 mmol, 3.00 equiv) and NMP (15 mL). The resulting solution was stirred overnight at 90° C. The resulting solution was extracted with of ethyl acetate. The combined extracts were washed with water. The mixture was dried ($Na_2SO_4$), filtered and concentrated in vacuo. The residue was purified by $SiO_2$ chromatography eluting with EtOAc/MeOH (30:1) that afforded 3.34 g (49%) of tert-butyl (2S)-2-([4-amino-3-iodo-1H-pyrazolo[4,3-c]pyridin-1-yl]methyl)pyrrolidine-1-carboxylate as a yellow solid.

Step 2:

A 100-mL round-bottom flask, was charged with tert-butyl (2S)-2-([4-amino-3-iodo-1H-pyrazolo[4,3-c]pyridin-1-yl]methyl)pyrrolidine-1-carboxylate (1.6 g, 3.61 mmol, 1.00 equiv), (2-fluoro-4-phenoxyphenyl)boronic acid (1.26 g, 5.43 mmol, 1.50 equiv), sodium carbonate (1.15 g, 10.85 mmol, 3.00 equiv), Pd(dppt)$Cl_2$ (260 mg, 0.36 mmol, 0.10 equiv), dioxane (18 mL) and water (3 mL). The resulting solution was stirred overnight at 90° C. The resulting mixture was dried ($Na_2SO_4$), filtered and concentrated in vacuo. The residue was applied onto a silica gel column with EA/MeOH (30:1). This resulted in 1.73 g (95%) of tert-butyl (2S)-2-[[4-amino-3-(2-fluoro-4-phenoxyphenyl)-1H-pyrazolo[4,3-c]pyridin-1-yl]methyl]pyrrolidine-1-carboxylate as a yellow solid.

Step 3:

A solution of tert-butyl (2S)-2-[[4-amino-3-(2-fluoro-4-phenoxyphenyl)-1H-pyrazolo[4,3-c]pyridin-1-yl]methyl]pyrrolidine-1-carboxylate (1.73 g, 3.44 mmol, 1.00 equiv), HCl (12M in dioxane, 10 mL) and dioxane (20 mL) was stirred for 2 h at RT. The reaction was then quenched by the addition of sat'd. $NaHCO_3$. The resulting solution was extracted with EtOAc/MeOH (10:1). The combined extracts were washed with sat'd. brine. The mixture was dried ($Na_2SO_4$), filtered and concentrated in vacuo to afford 1.3 g (94%) of 3-(2-fluoro-4-phenoxyphenyl)-1-[(2S)-pyrrolidin-2-ylmethyl]-1H-pyrazolo[4,3-c]pyridin-4-amine as a brown solid.

Step 4:

A 50-mL round-bottom flask, was charged with 3-(2-fluoro-4-phenoxyphenyl)-1-[(2S)-pyrrolidin-2-ylmethyl]-1H-pyrazolo[4,3-c]pyridin-4-amine (1.3 g, 3.22 mmol, 1.00 equiv), 2-cyanoacetic acid (260 mg, 3.06 mmol, 0.95 equiv), HATU (1.84 g, 4.84 mmol, 1.50 equiv), TEA (977 mg, 9.66 mmol, 3.00 equiv) and DMF (10 mL and stirred for 2 h at RT. The resulting solution was extracted with ethyl acetate. The combined extracts were washed with water. The mixture was dried ($Na_2SO_4$), filtered and concentrated in vacuo. The residue was purified by $SiO_2$ chromatography eluting with EtOAc/MeOH (30:1) to afford 1.06 g (70%) of 3-[(2S)-2-[[4-amino-3-(2-fluoro-4-phenoxy-phenyl)-1H-pyrazolo[4,3-c]pyridin-1-yl]methyl]pyrrolidin-1-yl]-3-oxopropanenitrile as a yellow solid.

Step 5:

A 8-mL vial was charged with 3-[(2S)-2-[[4-amino-3-(2-fluoro-4-phenoxyphenyl)-1H-pyrazolo[4,3-c]pyridin-1-yl]methyl]pyrrolidin-1-yl]-3-oxopropanenitrile (150 mg, 0.32 mmol, 1.00 equiv), 2-methyl-2-(4-methylpiperazin-1-yl)propanal (163 mg, 0.96 mmol, 3.00 equiv), TMSCl (172 mg, 1.58 mmol, 5.00 equiv), pyrrolidine (113 mg, 1.59 mmol, 5.00 equiv) and $CH_2Cl_2$ (2 mL). The resulting solution was stirred for 3 h at RT. The resulting mixture was concentrated in vacuo. The residue was purified by Prep-TLC with DCM/MeOH (20:1). The crude product was purified with a Shimadzu (HPLC-10) prep-HPLC with the following conditions: Column, The crude product was purified with a Shimadzu (HPLC-10) prep-HPLC with the following conditions: Column, XSelect CSH Prep C18 OBD Column, 19×150 mm 5 μm; mobile phase; mobile phase, $H_2O$ containing 0.05% TFA and MeCN (gradient of 20 to 50% ACN over 8 min) and afforded 59.5 mg (30%) of the title compound as a yellow solid. LC-MS m/z: 623.3 (M+1)

Example 2

Synthesis of 2-((S)-2-((4-amino-3-(2-fluoro-4-phenoxyphenyl)-1H-pyrazolo[4,3-c]pyridin-1-yl)methyl)pyrrolidine-1-carbonyl)-4-methyl-4-(4-(oxetan-3-yl)piperazin-1-yl)pent-2-enenitrile

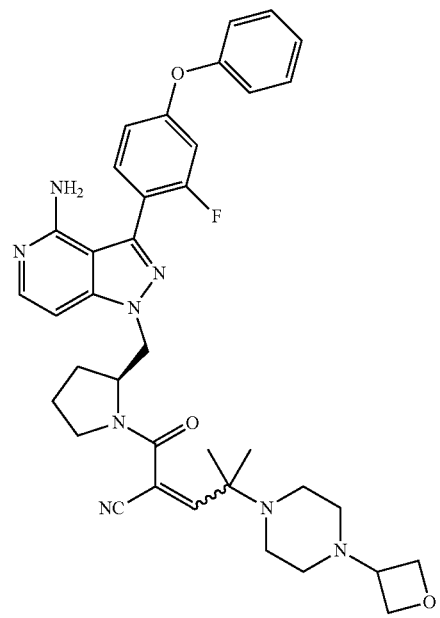 [SMILES: CC(C)(C=C(C#N)C(=O)N1CCC[C@H]1Cn1nc(-c2ccc(Oc3ccccc3)cc2F)c2c(N)nccc21)N1CCN(C2COC2)CC1]

A 8 mL vial was charged with 3-[(2S)-2-[[4-amino-3-(2-fluoro-4-phenoxyphenyl)-1H-pyrazolo[4,3-c]pyridin-1-yl]methyl]pyrrolidin-1-yl]-3-oxopropanenitrile (150 mg, 0.32 mmol, 1.00 equiv), 2-methyl-2-[4-(oxetan-3-yl)piperazin-1-yl]propanal (203 mg, 0.96 mmol, 3.00 equiv), TMSCl (172 mg, 1.58 mmol, 5.00 equiv), pyrrolidine (113 mg, 1.59 mmol, 5.00 equiv) and $CH_2Cl_2$ (2 mL) and stirred for 3 h at room temperature (RT). The resulting mixture was concentrated in vacuo. The residue was purified by Prep-TLC with DCM/MeOH (20:1). The crude product was purified by Prep-HPLC with the following conditions (2#-AnalyseHPLC-SHIMADZU (HPLC-10)): Column, XSelect CSH Prep C18 OBD Column, 19*150 mm 5 um 13 nm; mobile phase, Water with 0.05% trifluoroacetic acid and MeCN (20.0% MeCN up to 50.0% in 8 min); Detector, 254 nm. This resulted in 62.8 mg (30%) of the title compound as a light yellow solid. LC-MS m/z: 665.3 (M+1)

Example 3

Synthesis of (S)-2-(2-((8-amino-1-(2-fluoro-4-phenoxyphenyl)imidazo[1,5-a]pyrazin-3-yl)-methyl)pyrrolidine-1-carbonyl)-4,4-dimethylpent-2-enenitrile

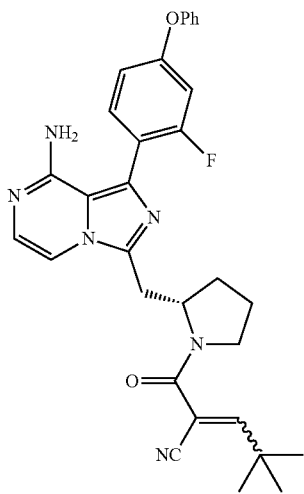 [SMILES: CC(C)(C)C=C(C#N)C(=O)N1CCC[C@H]1Cc1nc(-c2ccc(Oc3ccccc3)cc2F)c2c(N)nccn12]

Step 1:

To a solution of 2-chloro-3-cyanopyrazine (10.0 g, 72 mmol) and in AcOH (150 mL) was added Raney Ni (1 g, in water) and the mixture was stirred for 16 h under a hydrogen atmosphere maintained with a balloon at RT. The mixture was filtered and the filtrate was concentrated under in vacuo to afford a crude product, which was dissolved in 250 mL of 2M aqueous HCl and extracted with EtOAc (200 mL×2). The aqueous layer was concentrated in vacuo to afford crude (3-chloropyrazin-2-yl)methanamine as a brown solid. (8 g, 77.6%) which was used without additional purification.

Step 2:

To a mixture of (3-chloropyrazin-2-yl)methanamine (5 g, 35 mmol), (S)-2-(1-(tert-butoxycarbonyl)pyrrolidin-2-yl)acetic acid (8 g, 35 mmol) and HATU (13.3 g, 35 mmol) in DCM (80 mL) was added Et$_3$N (10.6 g, 105 mmol), the mixture was stirred for 18 h at room temperature. The mixture was concentrated in vacuo and diluted with water (80 mL), extracted with DCM. The combined organic layers were washed with brine, dried (Na$_2$SO$_4$), filtered and concentrated. The residue was purified by SiO$_2$ chromatography eluting with a PE/EtOAc gradient (25% to 100% EtOAc) to afford (S)-tort-butyl 2-(2-((3-chloropyrazin-2-yl)methylamino)-2-oxoethyl)pyrrolidine-1-carboxylate (5.5 g 44.3%).

Step 3:

To a solution of (S)-tert-butyl 2-(2-((3-chloropyrazin-2-yl)methylamino)-2-oxoethyl)pyrrolidine-1-carboxylate (5.5 g, 15.5 mmol) in EtOAc (80 mL) was added slowly POCl$_3$ (16.5 g, 105 mmol) and DMF (4 mL) at 0° C. and then stirred at RT for 2 h. The reaction was cooled in an ice bath and added slowly to a mixture of crushed ice and aq. NH$_4$OH (100 mL) cooled in an ice bath. The resultant mixture was extracted with EtOAc, washed with brine, dried over anhydrous Na$_2$SO$_4$, filtered and concentrated. The residue was purified by silica gel chromatography (PE/EtOAc=3:1 to EtOAc) to afford (S)-tert-butyl 2-((8-chloroimidazo[1,5-a]pyrazin-3-yl)methyl)pyrrolidine-1-carboxylate (3.5 g, 67.3%).

Step 4:

(S)-tert-butyl 2-((8-chloroimidazo[1,5-a]pyrazin-3-yl)methyl)pyrrolidine-1-carboxylate (3.5 g, 10.4 mmol) was dissolved in DMF (40 mL) and cooled to 0° C. NBS (2.4 g, 13.5 mmol) dissolved in 4 mL of DMF was added slowly and stirred for 1 h at RT. The reaction mixture was quenched with saturated NaHCO$_3$ (50 mL) and extracted with EtOAc. The combined organic phase was washed with brine and dried (Na$_2$SO$_4$), filtered and concentrated to give a crude residue (S)-tert-butyl 2-((1-bromo-8-chloroimidazo[1,5-a]pyrazin-3-yl)methyl) pyrrolidine-1-carboxylate (3.5 g).

Step 5:

(S)-tert-butyl 2-((1-bromo-8-chloroimidazo[1,5-a]pyrazin-3-yl)methyl) pyrrolidine-1-carboxylate (3.5 g, 8.45 mmol) dissolved in 30 mL of 7 M NH$_3$/MeOH. The mixture was heated for 2 h at 120° C. The reaction was concentrated and then dissolved in EtOAc and washed with H$_2$O. The aqueous layer was extracted with EtOAc. The combined organic layers were washed with brine (60 mL), dried (Na$_2$SO$_4$), filtered and concentrated to afford a crude product (S)-tert-butyl 2-((8-amino-1-bromoimidazo[1,5-a]pyrazin-3-yl)methyl) pyrrolidine-1-carboxylate (3.0 g, 90%).

Step 6:

A flask was charged with (S)-tert-butyl 2-((8-amino-1-bromoimidazo[1,5-a]pyrazin-3-yl)methyl) pyrrolidine-1-carboxylate (3.0 g, 7.6 mmol), (2-fluoro-4-phenoxyphenyl)boronic acid (1.76 g, 7.6 mmol), Na$_2$CO$_3$ (1.61 g, 15.2 mmol) and PdCl$_2$(dppf) (556 mg, 0.76 mmol), then dioxane (50 mL) and water (10 mL) were added. The solution was stirred at 85° C. for 3 h then cooled to RT. Water (40 mL) was added and the solution extracted with EtOAc. The combined organic layers were washed with water and brine, dried (Na$_2$SO$_4$), filtered and concentrated in vacuo. The crude residue, which was purified by SiO$_2$ chromatography eluting with a PE/EtOAc gradient (25% to 100% EtOAc) to afford (S)-tert-butyl 2-((8-amino-1-(2-fluoro-4-phenoxyphenyl)imidazo[1,5-a]pyrazin-3-yl)methyl)pyrrolidine-1-carboxylate as yellow oil (2.6 g, 68.4%).

Step 7:

To a stirred solution of (S)-tert-butyl 2-((8-amino-1-(2-fluoro-4-phenoxyphenyl)-imidazo[1,5-a]pyrazin-3-yl)methyl)pyrrolidine-1-carboxylate (2.6 g, 5.2 mmol) in DCM (4 mL) was added TFA (4 mL). The solution was stirred at RT for 2 h, concentrated in vacuo, then water (30 mL) was added. The mixture was extracted with EtOAc, the aqueous layer was adjusted to pH ca. 10 with aq. NaHCO$_3$, The mixture was extracted with EtOAc and the combined organic layers were dried (Na$_2$SO$_4$), filtered and concentrated in vacuo to afford (S)-1-(2-fluoro-4-phenoxyphenyl)-3-(pyrrolidin-2-ylmethyl)imidazo[1,5-a]pyrazin-8-amine as yellow oil (2.2 g, crude).

Step 8:

To a solution of (S)-1-(2-fluoro-4-phenoxyphenyl)-3-(pyrrolidin-2-ylmethyl)-imidazo[1,5-a]pyrazin-8-amine (1.5 g, 3.72 mmol), 2-cyanoacetic acid (380 mg, 4.47 mmol), HOBt (854 mg, 5.58 mmol), EDC (1.06 g, 5.58 mmol) in DMF (20 mL) was added DIPEA (1.44 g, 11.16 mmol). The mixture was stirred at RT for 2 h then extracted with EtOAc, The organic layer was washed with brine, dried (Na$_2$SO$_4$), filtered and concentrated in vacuo to afford (S)-3-(2-((8-amino-1-(2-fluoro-4-phenoxyphenyl)imidazo-

[1,5-a]pyrazin-3-yl)methyl)pyrrolidin-1-yl)-3-oxopropanenitrile (0.8 g, crude) as yellow solid.

Step 9:

To a solution of (S)-3-(2-((8-amino-1-(2-fluoro-4-phenoxyphenyl)imidazo[1,5-a]pyrazin-3-yl)methyl)pyrrolidin-1-yl)-3-oxopropanenitrile (150 mg, 0.32 mmol), pivalaldehyde (41 mg, 0.48 mmol) and pyrrolidine (0.6 mL) in DCM (4 mL) at RT was slowly added dropwise chloro(trimethyl)silane (0.4 mL). After 1 h the reaction was diluted with DCM (20 mL) and washed with aq. NaHCO₃). The organic layer was dried (Na₂SO₄), filtered and concentrated in vacuo to afford a crude residue, which was purified by Prep-TLC to afford the title compound as a white solid (21 mg, 12.2%). [M+H]+=538.9

Example 4

Synthesis of (S)-2-(2-((8-amino-1-(2-fluoro-4-phenoxyphenyl)imidazo[1,5-a]pyrazin-3-yl)methyl)pyrrolidine-1-carbonyl)-4-methyl-4-morpholinopent-2-enenitrile

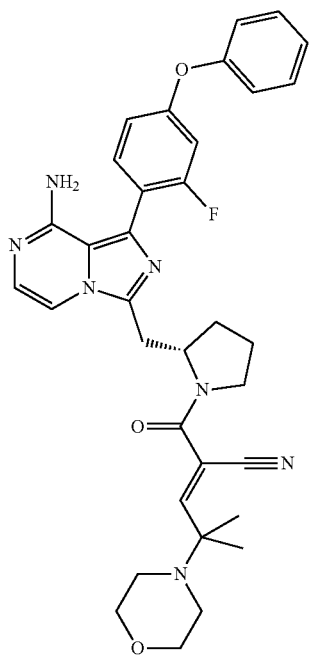 [SMILES: CC(C)(/C=C(\C#N)C(=O)N1CCC[C@H]1Cc1nc(-c2ccc(Oc3ccccc3)cc2F)c2c(N)nccn12)N1CCOCC1]

To a solution of (S)-3-(2-((8-amino-1-(2-fluoro-4-phenoxyphenyl)imidazo[1,5-a]pyrazin-3-yl)methyl)pyrrolidin-1-yl)-3-oxopropanenitrile (150 mg, 0.32 mmol), 2-methyl-2-morpholinopropanal (75 mg, 0.48 mmol) and pyrrolidine (0.6 mL) in DCM (4 mL) at RT was slowly added dropwise chloro(trimethyl)silane (0.4 mL). After 1 h the reaction was diluted with DCM (20 mL) and washed with aq. NaHCO₃ (20 mL). The organic layer was dried (Na₂SO₄), filtered and concentrated in vacuo and the crude residue, which was purified by Prep-TLC to afford the title compound as white solid (13 mg, 7%). [M=H]+=609.9

Proceeding as described above, 2-(3-((4-amino-3-(2-fluoro-4-phenoxyphenyl)-1H-pyrazolo[4,3-c]pyridin-1-yl)methyl)pyrrolidine-1-carbonyl)-4-methyl-4-(4-methylpiperazin-1-yl)pent-2-enenitrile was prepared using 2-methyl-2-(4-methylpiperazin-1-yl)propanal.

Example 5

Synthesis of (S)-2-(2-((8-amino-1-(2-fluoro-4-phenoxyphenyl)imidazo[1,5-a]pyrazin-3-yl)-methyl)pyrrolidine-1-carbonyl)-4-methyl-4-(methyl(oxetan-3-yl)amino)pent-2-enenitrile

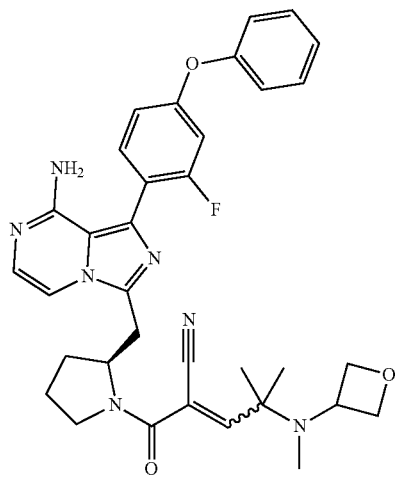 [SMILES: CN(C1COC1)C(C)(C)C=C(C#N)C(=O)N1CCC[C@H]1Cc1nc(-c2ccc(Oc3ccccc3)cc2F)c2c(N)nccn12]

Step 1:

To a solution of 2-methyl-propanal (1 g, 13.9 mmol) in DCM (15 mL) cooled to 0° C. was slowly added bromine (2.6 g, 16.7 mmol). After the bromine was added the reaction mixture was stirred at RT for 2 h then quenched with saturated Na₂S₂O₃ and saturated NaHCO₃ (1:1) and extracted with DCM. The solvent was removed at lower temperature to afford crude 2-bromo-2-methylpropanal (1 g) which was used in the next step without additional purification.

Step 2:

A solution of 2-bromo-2-methylpropanal (1 g, 6.7 mmol), N-methyloxetan-3-amine (250 mg, 2.87 mmol) and Et₃N (1.35 g, 13.4 mmol) in DCM (10 mL) at 0° C. was stirred for 3 h. The solvent was removed to give a residue, which was purified by SiO₂ chromatography eluting with PE:EtOAc (1:1) to afford 2-methyl-2-(methyl(oxetan-3-yl)amino)propanal (200 mg, 44.4%) as a oil.

Step 3:

To a solution of (S)-3-(2-((8-amino-1-(2-fluoro-4-phenoxyphenyl)imidazo[1,5-a]pyrazin-3-yl)methyl)pyrrolidin-1-yl)-3-oxopropanenitrile (150 mg, 0.32 mmol), methyl-2-(methyl(oxetan-3-yl)amino)propanal (200 mg, 1.27 mmol) and pyrrolidine (0.5 mL) in DCM (4 mL) at RT was slowly added dropwise chloro(trimethyl)silane (0.4 mL). After 1 h the reaction was diluted with DCM and washed with aq. NaHCO₃. The organic layer was dried (Na₂SO₄), filtered and concentrated in vacuo. The crude residue was purified by Prep-TLC to afford the title compound (25 mg, 13%) as white solid. [M+H]⁺=609.9.

Example 6

Synthesis of (R)-2-(3-(4-amino-3-(2-fluoro-4-phenoxyphenyl)-1H-pyrazolo[4,3-c]pyridin-1-yl)piperidine-1-carbonyl)-4,4-dimethylpent-2-enenitrile

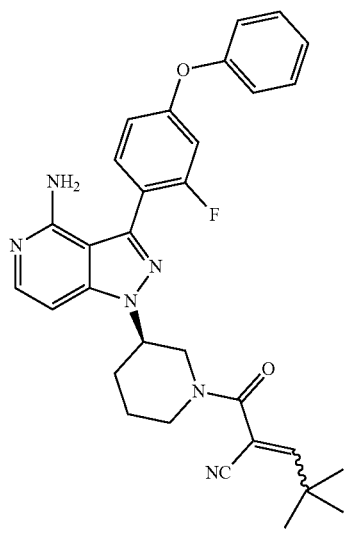 [SMILES: CC(C)(C)C=C(C#N)C(=O)N1CCC[C@@H](n2nc(-c3ccc(Oc4ccccc4)cc3F)c3c(N)nccc32)C1]

Step 1:

Into a 250-mL 3-necked round-bottom flask purged and maintained under an inert atmosphere of nitrogen, was placed tert-butyl (3S)-3-hydroxypiperidine-1-carboxylate (5 g, 24.84 mmol, 1.00 equiv) and TEA (7.54 g, 74.51 mmol, 3.00 equiv) in CH$_2$Cl$_2$ (100 mL). MsCl (5.70 g, 49.78 mmol, 2.00 equiv) was added at 0° C. and the resulting solution was stirred for 2 h at 0° C. in a water/ice bath. The reaction was quenched by the addition of sat'd. NaHCO$_3$ and the resulting solution was extracted with CH$_2$Cl$_2$ and the organic layers combined. The resulting mixture was washed with sat'd. NaCl. The mixture was dried (Na$_2$SO$_4$), filtered and concentrated in vacuo to afford 6.3 g (91%) of tert-butyl (3S)-3-(methanesulfonyloxy)piperidine-1-carboxylate as a yellow solid.

Step 2:

A 100-mL round-bottom flask, was charged with tert-butyl (3S)-3-(methane-sulfonyloxy)piperidine-1-carboxylate (1.61 g, 5.76 mmol, 1.50 equiv), 3-iodo-1H-pyrazolo [4,3-c]pyridin-4-amine (1 g, 3.85 mmol, 1.00 equiv), Cs$_2$CO$_3$ (3.76 g, 11.54 mmol, 3.00 equiv) and NMP (38 mL). The resulting solution was stirred for 5 h at 90° C. in an oil bath. The resulting solution was extracted with ethyl acetate and the organic layers combined. The resulting mixture was washed with water. The mixture was dried (Na$_2$SO$_4$), filtered and concentrated in vacuo. The residue was purified by SiO$_2$ chromatography eluting with EtOAc/MeOH (30:1 containing 3 mL NH$_3$ (25%)/L) to afford 460 mg (27%) of tert-butyl (3R)-3-[4-amino-3-iodo-1H-pyrazolo[4,3-c]pyridin-1-yl]-piperidine-1-carboxylate as a yellow solid.

Step 3:

A 50-mL round-bottom flask was charged with tert-butyl (3R)-3-[4-amino-3-iodo-1H-pyrazolo[4,3-c]pyridin-1-yl]piperidine-1-carboxylate (460 mg, 1.04 mmol, 1.00 equiv), (2-fluoro-4-phenoxyphenyl)boronic acid (361 mg, 1.56 mmol, 1.50 equiv), Na$_2$CO$_3$ (330 mg, 3.11 mmol, 3.00 equiv), Pd(dppf)Cl$_2$ (76 mg, 0.10 mmol, 0.10 equiv), dioxane (15 mL) and water (3 mL). The resulting solution was stirred for 3 h at 90° C. in an oil bath. The reaction mixture was extracted with EtOAc and the organic layers combined. The resulting mixture was washed with sat'd NaCl. The mixture was dried (Na$_2$SO$_4$), filtered and concentrated in vacuo. The residue was purified by SiO$_2$ chromatography eluting with EtOAc/MeOH (30:1 containing 3 mL NH$_3$ (25%)/L) to afford 520 mg (100%) of tert-butyl (3R)-3-[4-amino-3-(2-fluoro-4-phenoxyphenyl)-1H-pyrazolo[4,3-c]pyridin-1-yl]-piperidine-1-carboxylate as a yellow solid.

Step 4:

A 50-mL round-bottom flask was charged with tert-butyl (3R)-3-[4-amino-3-(2-fluoro-4-phenoxyphenyl)-1H-pyrazolo[4,3-c]pyridin-1-yl]piperidine-1-carboxylate (520 mg, 1.03 mmol, 1.00 equiv), HCl (2 mL, 12 M in dioxane) and dioxane (10 mL). The resulting solution was stirred for 1 h at RT. The reaction was then quenched by the addition of sat'd. NaHCO$_3$. The resulting solution was extracted with 3×100 mL of ethyl acetate. The combined organic layers were washed with 1×100 mL of sat'd. brine. The mixture was dried (Na$_2$SO$_4$), filtered and concentrated in vacuo to afford 450 mg (crude) of 3-(2-fluoro-4-phenoxyphenyl)-1-[(3R)-piperidin-3-yl]-1H-pyrazolo[4,3-c]pyridin-4-amine as a brown solid.

Step 5:

A 50-mL round-bottom flask was charged with 3-(2-fluoro-4-phenoxyphenyl)-1-[(3R)-piperidin-3-yl]-1H-pyrazolo[4,3-c]pyridin-4-amine (450 mg, 1.12 mmol, 1.00 equiv), 2-cyanoacetic acid (90 mg, 1.06 mmol, 0.95 equiv), HATU (636 mg, 1.67 mmol, 1.50 equiv), TEA (338 mg, 3.34 mmol, 3.00 equiv), DMF (10 mL). The resulting solution was stirred for 2 h at RT. The resulting solution was extracted with ethyl acetate. The combined organic layers were washed with water. The mixture was dried (Na$_2$SO$_4$), filtered and concentrated in vacuo. The residue was purified by SiO$_2$ chromatography eluting with EtOAc/MeOH (30:1 containing 3 mL NH$_3$ (25%)/L) to afford 400 mg (76%) of 3-[(3R)-3-[4-amino-3-(2-fluoro-4-phenoxyphenyl)-1H-pyrazolo[4,3-c]-pyridin-1-yl]piperidin-1-yl]-3-oxopropanenitrile as a yellow solid.

Step 6:

Into a 8-mL vial, was placed 3-[(3R)-3-[4-amino-3-(2-fluoro-4-phenoxyphenyl)-1H-pyrazolo[4,3-c]pyridin-1-yl]piperidin-1-yl]-3-oxopropanenitrile (100 mg, 0.21 mmol, 1.00 equiv), 2,2-dimethylpropanal (55 mg, 0.64 mmol, 3.00 equiv), TMSCl (115 mg, 1.06 mmol, 5.00 equiv), pyrrolidine (76 mg, 1.07 mmol, 5.00 equiv) and CH₂Cl₂ (2 mL). The resulting solution was stirred overnight at RT. The resulting solution was extracted with 2×20 mL of ethyl acetate. The combined extracts were washed with 1×20 mL of sat'd. brine. The mixture was dried (Na₂SO₄), filtered and concentrated in vacuo. The crude product was purified with a Shimadzu (HPLC-10) prep-HPLC with the following conditions: Column, Gemini-NX C18 AXAI Packed, 21.2× 150 mm 5 μm; mobile phase, H₂O containing 0.05% TFA and MeCN (gradient of 20 to 50% ACN over 8 min) and afforded 20 mg (17%) of the title compound as a white solid. LC-MS m/z: 539.2 (M+1)

(109 mg, 0.64 mmol, 3.00 equiv), TMSCl (115 mg, 1.06 mmol, 5.00 equiv), pyrrolidine (76 mg, 1.07 mmol, 5.00 equiv), CH₂Cl₂ (2 mL). The resulting solution was stirred overnight at room temperature. The resulting solution was extracted with ethyl acetate. The combined extracts were washed with sat'd. brine. The mixture was dried (Na₂SO₄), filtered and concentrated in vacuo. The crude product was purified with a Shimadzu (HPLC-10) prep-HPLC with the following conditions: Column, Gemini-NX C18 AXAI Packed, 21.2×150 mm 5 μm; mobile phase, H₂O containing 0.05% TFA and MeCN (gradient of 20 to 50% ACN over 8 min) and afforded 52.7 mg (40%) of the title compound as a light yellow solid. LC-MS m/z: 623.1 (M+1)

Example 7

Synthesis of (R)-2-(3-(4-amino-3-(2-fluoro-4-phenoxyphenyl)-1H-pyrazolo[4,3-c]pyridin-1-yl)piperidine-1-carbonyl)-4-methyl-4-(4-methylpiperazin-1-yl)pent-2-enenitrile Example 8

Synthesis of 2-((R)-3-(4-amino-3-(2-fluoro-4-phenoxyphenyl)-1H-pyrazolo[4,3-c]pyridin-1-yl)piperidine-1-carbonyl)-4-methyl-4-morpholinopent-2-enenitrile

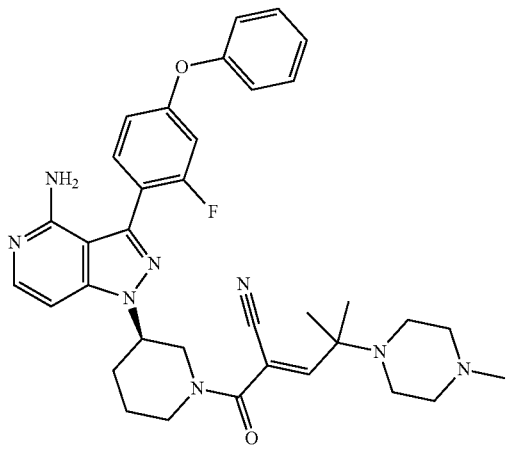 [SMILES: CN1CCN(C(C)(C)/C=C(\C#N)C(=O)N2CCC[C@@H](n3nc(-c4ccc(Oc5ccccc5)cc4F)c4c(N)nccc43)C2)CC1]

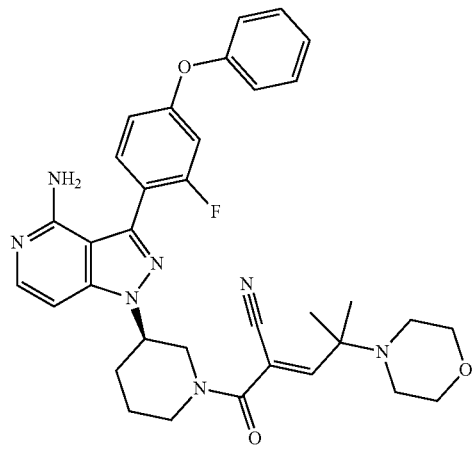 [SMILES: CC(C)(/C=C(\C#N)C(=O)N1CCC[C@@H](n2nc(-c3ccc(Oc4ccccc4)cc3F)c3c(N)nccc32)C1)N1CCOCC1]

Step 1:

A 100-mL round-bottom flask was charged with 2-bromo-2-methylpropanal (3.05 g, 20.20 mmol, 1.00 equiv) in ether (30 mL). 1-Methylpiperazine (7.12 g, 71.08 mmol, 3.50 equiv) was added at 0° C. and the resulting solution was stirred overnight at RT. The solids were filtered and the pH of the solution was adjusted to 8 with K₂CO₃. The solids were filtered and the filtrate was washed with water. The mixture was dried (Na₂SO₄), filtered and concentrated in vacuo to afford 1.65 g (48%) of 2-methyl-2-(4-methylpiperazin-1-yl)propanal as light yellow oil.

Step 2:

An 8-mL vial was charged with 3-[(3R)-3-[4-amino-3-(2-fluoro-4-phenoxyphenyl)-1H-pyrazolo[4,3-c]pyridin-1-yl] piperidin-1-yl]-3-oxopropanenitrile (100 mg, 0.21 mmol, 1.00 equiv), 2-methyl-2-(4-methylpiperazin-1-yl)propanal A 8-mL vial was charged with 3-[(3R)-3-[4-amino-3-(2-fluoro-4-phenoxyphenyl)-1H-pyrazolo[4,3-c]pyridin-1-yl] piperidin-1-yl]-3-oxopropanenitrile (100 mg, 0.21 mmol, 1.00 equiv), 2-methyl-2-(morpholin-4-yl)propanal (100 mg, 0.64 mmol, 3.00 equiv, CASRN 16042-91-4), TMSCl (115 mg, 1.06 mmol, 5.00 equiv), pyrrolidine (76 mg, 1.07 mmol, 5.00 equiv) and CH₂Cl₂ (2 mL). The resulting solution was stirred overnight at RT. The resulting solution was extracted with EtOAc. The combined extracts washed with sat'd. brine. The mixture was dried (Na₂SO₄), filtered and concentrated in vacuo. The crude product was purified was purified with a Shimadzu (HPLC-10) prep-HPLC with the following conditions: Column, Gemini-NX C18 AXAI Packed, 21.2×150 mm 5 μm; mobile phase, H₂O containing 0.05% TFA and MeCN (gradient of 20 to 50% ACN over 8 min) and afforded 37.7 mg (29%) of the title compound as a white solid. LC-MS m/z: 610.2 (M+1)

Example 9

Synthesis of (R)-2-(3-(4-amino-3-(2-fluoro-4-phenoxyphenyl)-1H-pyrazolo[4,3-c]pyridin-1-yl)piperidine-1-carbonyl)-4-methyl-4-(4-(oxetan-3-yl)piperazin-1-yl)pent-2-enenitrile

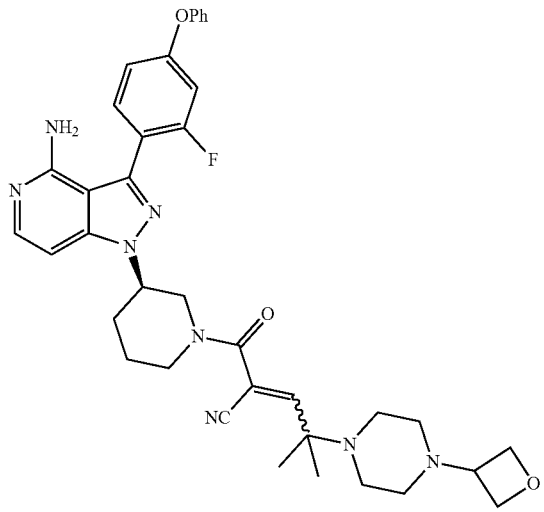 [SMILES: CC(C)(C=C(C#N)C(=O)N1CCC[C@@H](n2nc(-c3ccc(Oc4ccccc4)cc3F)c3c(N)nccc32)C1)N1CCN(C2COC2)CC1]

To a solution of 3-[(3R)-3-[4-amino-3-(2-fluoro-4-phenoxyphenyl)-1H-pyrazolo[4,3-c]pyridin-1-yl]piperidin-1-yl]-3-oxopropanenitrile (80 mg, 0.1700 mmol), 2-methyl-2-(4-(oxetan-3-yl)piperazin-1-yl)propanal (108.9 mg, 0.510 mmol) in CH$_2$Cl$_2$ (10 mL) cooled to 0° C. was added trimethylsilyl chloride (0.0863 mL, 0.6801 mmol) and pyrrolidine (0.0838 mL, 1.0202 mmol). After the addition was complete the cooling bath was removed and the reaction stirred at RT for 3 h. The solvent was evaporated and the residue adsorbed on a SiO$_2$ column and eluted with a CH$_2$Cl$_2$/MeOH gradient (0-5, 9 and 10/% MeOH) to afford 29 mg of the title compound.

Example 10

Synthesis of (R)-2-(3-(4-amino-3-(2-fluoro-4-phenoxyphenyl)-1H-pyrazolo[4,3-c]pyridin-1-yl)piperidine-1-carbonyl)-4-methyl-4-(4-(3-methyloxetan-3-yl)piperazin-1-yl)pent-2-enenitrile

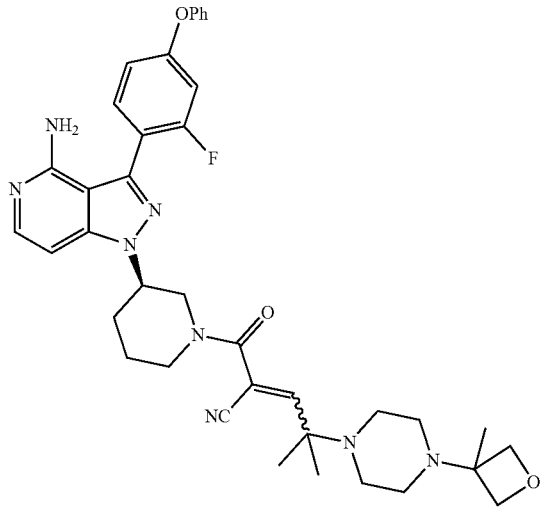 [SMILES: CC(C)(C=C(C#N)C(=O)N1CCC[C@@H](n2nc(-c3ccc(Oc4ccccc4)cc3F)c3c(N)nccc32)C1)N1CCN(C2(C)COC2)CC1]

To a solution of 3-[(3R)-3-[4-amino-3-(2-fluoro-4-phenoxyphenyl)-1H-pyrazolo[4,3-c]pyridin-1-yl]piperidin-1-yl]-3-oxopropanenitrile (55 mg, 0.1170 mmol), 2-methyl-2-(4-(3-methyloxetan-3-yl)piperazin-1-yl)propanal (79.37 mg, 0.351 mmol) in CH$_2$Cl$_2$ (10 mL) cooled to 0° C. was added trimethylsilyl chloride (0.059 mL, 0.4680 mmol) and pyrrolidine (0.058 mL, 0.7010 mmol). After the addition was complete the cooling bath was removed and the reaction stirred at RT for 3 h. The solvent was evaporated and the residue adsorbed on a preparative SiO$_2$ plate and developed with 5% MeOH/CH$_2$Cl$_2$) to afford 52 mg of the title compound. MS [M+H]$^+$=680.3

2-Methyl-2-(4-(3-methyloxetan-3-yl)piperazin-1-yl)propanal can be prepared by treating 2-bromo-2-methylpropanal with 1-(3-methyl-3-oxetanyl)piperazine [CASRN-1515866-65-1].

Example 11

Synthesis of (R)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(3-methyloxetan-3-yl)piperazin-1-yl)pent-2-enenitrile

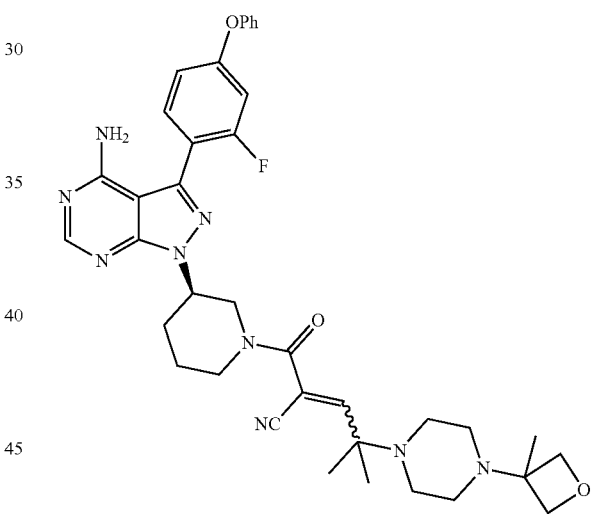

To a solution of (R)-3-(3-(4-amino-3-(2-fluoro-4-phenoxyphenyl)-1H-pyrazolo[3,4-d]pyrimidin-1-yl)piperidin-1-yl)-3-oxopropanenitrile (177 mg, 0.783 mmol), 2-methyl-2-(4-(3-methyloxetan-3-yl)piperazin-1-yl)propanal (123 mg, 0.261 mmol) in CH$_2$Cl$_2$ (10 mL) cooled to 0° C. was added trimethylsilyl chloride (0.132 mL, 1.04 mmol) and pyrrolidine (1.28 mL, 1.56 mmol). After the addition was complete the cooling bath was removed and the reaction stirred at RT for 3 h. The solvent was evaporated and the residue adsorbed on a preparative SiO$_2$ plate and developed with 5% MeOH/CH$_2$Cl$_2$) to afford 145 mg of the title compound. MS [M+H]$^+$=681.3.

(R)-3-(3-(4-amino-3-(2-fluoro-4-phenoxyphenyl)-1H-pyrazolo[3,4-d]pyrimidin-1-yl)piperidin-1-yl)-3-oxopropanenitrile was prepared as described in PCT Int. Appl., 20131e965.

Example 12

Synthesis of (R)-2-(3-(8-amino-1-(2-fluoro-4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile

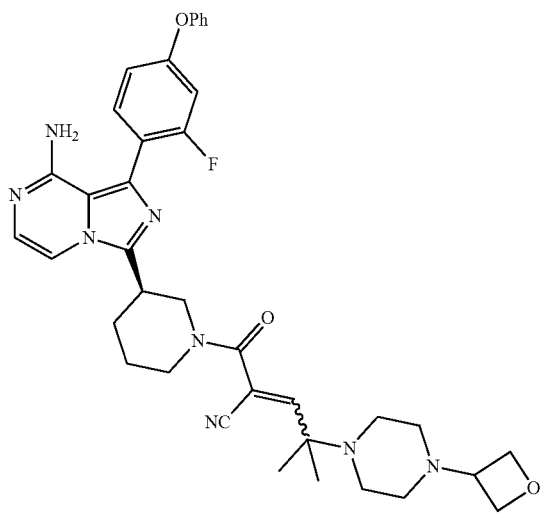 [SMILES: CC(C)(C=C(C#N)C(=O)N1CCC[C@@H](c2nc(-c3ccc(Oc4ccccc4)cc3F)c3c(N)nccn23)C1)N1CCN(C2COC2)CC1]

Step 1:

To a solution of 3-chloropyrazine-2-carbonitrile (15.0 g, 108 mmol) in AcOH (200 mL) was added Raney Ni (3 g, in water), and the mixture was stirred for 48 h under an atmosphere of hydrogen with a balloon at rt. The mixture was filtered and the filtrate was concentrated in vacuo to give a crude product, which was dissolved in 250 mL of aqueous HCl (2M) and extracted with EtOAc (200 mL×2). The aqueous layer was concentrated under vacuo to give 14.5 g of (3-chloropyrazin-2-yl)methanamine hydrochloride as a brown solid which was used in the next step without further purification.

Step 2:

To a mixture of (3-chloropyrazin-2-yl)methanamine hydrochloride (7.29 g, 40.5 mmol), (R)-1-(tert-butoxycarbonyl)piperidine-3-carboxylic acid (11.1 g, 48.6 mmol) and HATU (18.42 g, 48.6 mmol) in DCM (250 mL) was added DIPEA (15.7 g, 121.5 mmol), the mixture was stirred for 18 h at rt. The mixture was concentrated in vacuo and diluted with water (80 mL), extracted with DCM (150 mL×3). The combined organic layer was washed with brine (100 mL), dried over anhydrous Na$_2$SO$_4$, filtered and concentrated. The residue was purified by silica gel chromatography (PE/EtOAc=3:1 to EtOAc) to give 12 g of (R)-tert-butyl 3-((3-chloropyrazin-2-yl)methylcarbamoyl)piperidine-1-carboxylate.

Step 3:

To a solution of (R)-tert-butyl 3-((3-chloropyrazin-2-yl)methylcarbamoyl)piperidine-1-carboxylate (11 g, 31 mmol) in ACN (220 mL) at 0° C. were added POCl$_3$ (2.86 mL) and DMF (0.286 mL) slowly, after stirring for 6 h at room temperature, the reaction was cooled in an ice bath and quenched by slow addition of a mixture of crushed ice and aq. NH$_4$OH (100 mL). The resultant mixture was extracted with EtOAc (80 mL×3), washed with brine (100 mL), dried over anhydrous Na$_2$SO$_4$, filtered and concentrated. The residue was purified by silica gel chromatography (PE/EtOAc=3:1 to EtOAc) to afford 6.9 g of (R)-tert-butyl 3-(8-chloroimidazo[1,5-a]pyrazin-3-yl)piperidine-1-carboxylate.

Step 4:

(R)-tert-butyl 3-(8-chloroimidazo[1,5-a]pyrazin-3-yl)piperidine-1-carboxylate (6.9 g, 20.4 mmol) was dissolved in DMF (80 mL) and cooled to 0° C. NBS (3.64 g, 20.4 mmol) dissolved in 8 mL of DMF was added slowly and stirred for 1 h at rt. The reaction mixture was quenched with saturated NaHCO$_3$ and extracted with EtOAc. The combined organic phase was washed with brine and dried over anhydrous Na$_2$SO$_4$, filtered and concentrated to yield 8.4 g of (R)-tert-butyl 3-(1-bromo-8-chloroimidazo[1,5-a]pyrazin-3-yl)piperidine-1-carboxylate which was used in the next step without further purification.

Step 5:

(R)-tert-butyl 3-(1-bromo-8-chloroimidazo[1,5-a]pyrazin-3-yl)piperidine-1-carboxylate (8.41 g, 20.2 mmol) was dissolved in 90 mL of 7 M ammonia in MeOH. The mixture was heated for 2 h at 120° C. The reaction was concentrated and then dissolved in EtOAc (50 mL) and washed with H$_2$O (40 mL). The aqueous layer was extracted with EtOAc (50 mL). The combined organic layers were washed with brine (60 mL), dried over anhydrous Na$_2$SO$_4$ and concentrated to afford 4.3 g of (R)-tert-butyl 3-(8-amino-1-bromoimidazo[1,5-a]pyrazin-3-yl)piperidine-1-carboxylate which was used in the next step without further purification.

Step 6:

To a flask were added (R)-tert-butyl 3-(8-amino-1-bromoimidazo[1,5-a]pyrazin-3-yl)piperidine-1-carboxylate (3.0 g, 7.6 mmol), (2-fluoro-4-phenoxyphenyl)boronic acid (2.11 g, 9.09 mmol), Na$_2$CO$_3$ (1.61 g, 15.2 mmol) and PdCl$_2$(dppf) (277 mg, 0.379 mmol), followed by addition of dioxane (30 mL) and water (10 mL). After stirring at 85° C. for 3 h, the reaction was cooled to rt, diluted with water, and extracted with EtOAc. The combined organic layer was washed sequentially with water and brine, dried over anhydrous Na$_2$SO$_4$, filtered and concentrated in vacuo. Purification by silica gel chromatography (PE/EtOAc=3:1 to EtOAc) afforded 2.3 g of (R)-tert-butyl 3-(8-amino-1-(2-fluoro-4-phenoxyphenyl)imidazo[1,5-a]pyrazin-3-yl)piperidine-1-carboxylate as a yellow oil.

Step 7:

To a stirred solution of (R)-tert-butyl 3-(8-amino-1-(2-fluoro-4-phenoxyphenyl)imidazo[1,5-a]pyrazin-3-yl)piperidine-1-carboxylate (2.3 g, 4.6 mmol) in DCM (24 mL) was added (8 mL). The solution was stirred at rt for 2 h, then concentrated in vacuo. The residue was partitioned between water and EtOAc, the aqueous layer was neutralized with aqueous sodium bicarbonate to pH=10 and extracted with EtOAc. The combined organic layer was dried over anhydrous $Na_2SO_4$, filtered and concentrated in vacuo to afford 1.83 g of (R)-1-(2-fluoro-4-phenoxyphenyl)-3-(piperidin-3-yl)imidazo[1,5-a]pyrazin-8-amine as yellow oil which was used without further purification.

Step 8:

To a solution of (R)-1-(2-fluoro-4-phenoxyphenyl)-3-(piperidin-3-yl)imidazo[1,5-a]pyrazin-8-amine (1.83 g, 4.55 mmol), 2-cyanoacetic acid (348 mg, 4.1 mmol), HOBt (904 mg, 5.91 mmol), EDC (1.12 g, 5.91 mmol) in DCM (50 mL) was added DIPEA (1.17 g, 9.1 mmol). The mixture was stirred at rt for 2 h before diluting with EtOAc. The organic layer was washed with brine, dried over anhydrous $Na_2SO_4$, filtered and evaporated in vacuo to give 0.8 g of (R)-3-(3-(8-amino-1-(2-fluoro-4-phenoxyphenyl)imidazo[1,5-a]pyrazin-3-yl)piperidin-1-yl)-3-oxopropanenitrile as yellow solid which could be used in the next step without further purification.

Step 9:

To a solution of (R)-3-(3-(8-amino-1-(2-fluoro-4-phenoxyphenyl)imidazo[1,5-a]pyrazin-3-yl)piperidin-1-yl)-3-oxopropanenitrile (100 mg, 0.213 mmol), 2-methyl-2-(4-(oxetan-3-yl)piperazin-1-yl)propanal (90 mg, 0.43 mmol) and pyrrolidine (62 mg, 0.87 mmol) in DCM (3 mL) at rt was slowly added chloro(trimethyl)silane (69 mg, 0.64 mmol) dropwise. After 1 h, the reaction was diluted with DCM and washed with aq. $NaHCO_3$. The organic layer was dried over anhydrous sodium sulfate, filtered and concentrated. Purification by Prep-TLC afforded 25 mg of (R)-2-(3-(8-amino-1-(2-fluoro-4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile as a white solid. MS $[M+H]^+=665.7$.

Example 13

Synthesis of (R)-2-(3-(8-amino-1-(2-fluoro-4-phenoxyphenyl)imidazo[1,5-a]pyrazin-3-yl)piperidine-1-carbonyl)-4-methyl-4-(4-methyl-3-oxopiperazin-1-yl)pent-2-enenitrile

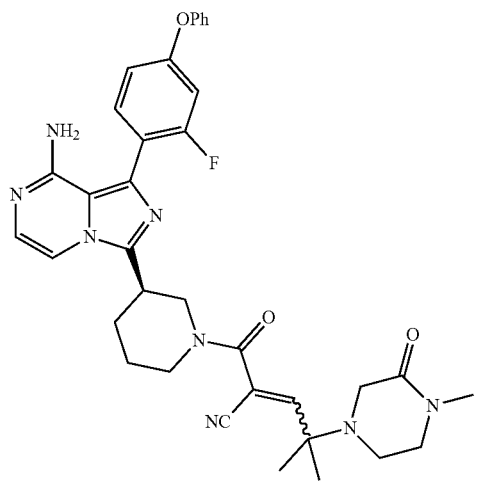 [SMILES: CN1CCN(C(C)(C)C=C(C#N)C(=O)N2CCC[C@@H](c3nc(-c4ccc(Oc5ccccc5)cc4F)c4c(N)nccn34)C2)CC1=O]

Following the procedure in Step 9, Example 12, but replacing 2-methyl-2-(4-(oxetan-3-yl)piperazin-1-yl)propanal with 2-methyl-2-(4-methyl-3-oxopiperazin-1-yl)propanal affords the title compound. MS $[M+H]^+=637.7$.

Example 14

Synthesis of (R)-2-(3-(8-amino-1-(2-fluoro-4-phenoxyphenyl)imidazo[1,5-a]pyrazin-3-yl)piperidine-1-carbonyl)-3-(4-methyltetrahydro-2H-pyran-4-yl)acrylonitrile

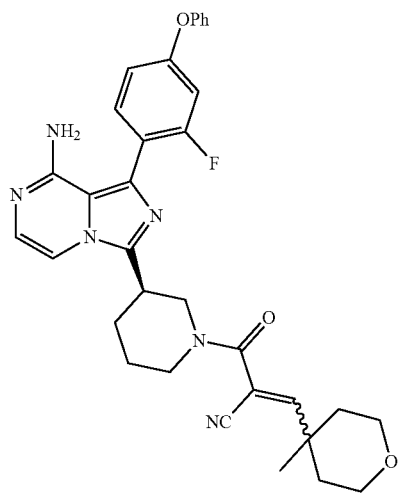 [SMILES: CC1(C=C(C#N)C(=O)N2CCC[C@@H](c3nc(-c4ccc(Oc5ccccc5)cc4F)c4c(N)nccn34)C2)CCOCC1]

Following the procedure in Step 9, Example 12, but replacing 2-methyl-2-(4-(oxetan-3-yl)piperazin-1-yl)propanal with 4-methyltetrahydro-2H-pyran-4-carbaldehyde affords the title compound. MS $[M+H]^+=582.2$.

Example 15

Synthesis of (R)-2-(3-(8-amino-1-(2-fluoro-4-phenoxyphenyl)imidazo[1,5-a]pyrazin-3-yl)piperidine-1-carbonyl)-4-methyl-4-(4-(3-methyloxetan-3-yl)piperazin-1-yl)pent-2-enenitrile

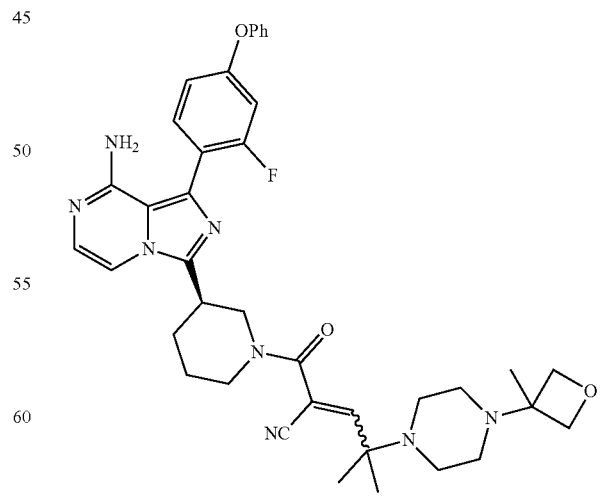

Following the procedure in Step 9, Example 12, but replacing 2-methyl-2-(4-(oxetan-3-yl)piperazin-1-yl)propanal with 2-methyl-2-(4-(3-methyloxetan-3-yl)piperazin-1-yl)propanal affords the title compound. MS $[M+H]^+=680.3$.

Example 16

Synthesis of (R)-methyl 4-(5-(3-(8-amino-1-(2-fluoro-4-phenoxyphenyl)imidazo[1,5-a]pyrazin-3-yl)piperidin-1-yl)-4-cyano-2-methyl-5-oxopent-3-en-2-yl)piperazine-1-carboxylate

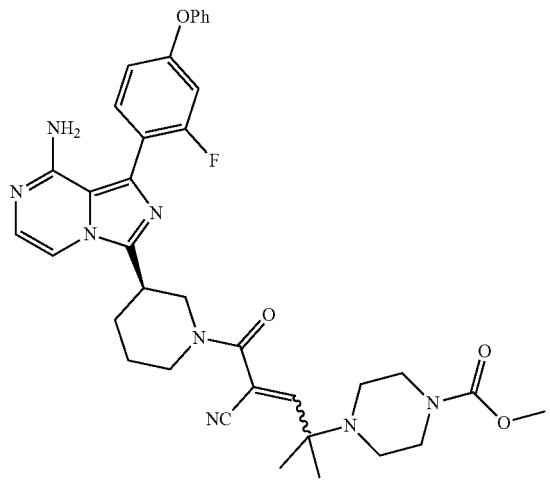 [SMILES: COC(=O)N1CCN(C(C)(C)C=C(C#N)C(=O)N2CCC[C@@H](c3nc(-c4ccc(Oc5ccccc5)cc4F)c4c(N)nccn34)C2)CC1]

Step 1

Into a 100-mL round-bottom flask, was placed methyl piperazine-1-carboxylate (1.9 g, 12.5 mmol, 2.00 equiv), diethyl ether (100 mL), and 2-bromo-2-methylpropanal (1 g, 6.29 mmol, 1.00 equiv). The resulting solution was stirred for overnight at 25° C. The resulting mixture was concentrated under vacuum affording 1.5 g of methyl 4-(2-methyl-1-oxopropan-2-yl)piperazine-1-carboxylate as a light yellow oil which was used without further purification.

Step 2

Following the procedure in Step 9, Example 12, but replacing 2-methyl-2-(4-(oxetan-3-yl)piperazin-1-yl)propanal with methyl 4-(2-methyl-1-oxopropan-2-yl)piperazine-1-carboxylate affords the title compound. MS [M+H]⁺=667.4.

Example 17

Synthesis of (R)-4-(4-acetylpiperazin-1-yl)-2-(3-(8-amino-1-(2-fluoro-4-phenoxyphenyl)imidazo[1,5-a]pyrazin-3-yl)piperidine-1-carbonyl)-4-methylpent-2-enenitrile

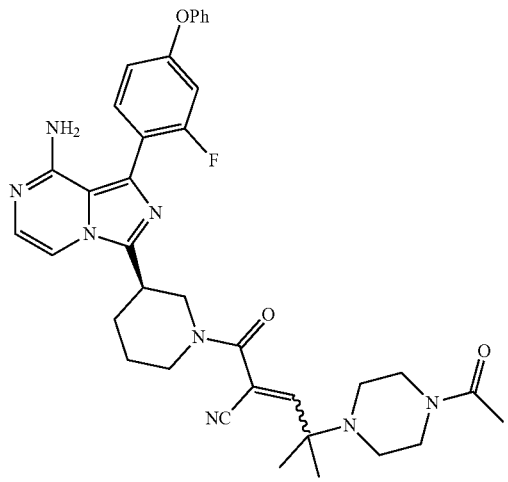 [SMILES: CC(=O)N1CCN(C(C)(C)C=C(C#N)C(=O)N2CCC[C@@H](c3nc(-c4ccc(Oc5ccccc5)cc4F)c4c(N)nccn34)C2)CC1]

Following the procedure in Step 9, Example 12, but replacing 2-methyl-2-(4-(oxetan-3-yl)piperazin-1-yl)propanal with 2-(4-acetylpiperazin-1-yl)-2-methylpropanal affords the title compound. MS [M+H]⁺=651.5.

Example 18

Synthesis of (R)-2-(3-(8-amino-1-(2-fluoro-4-phenoxyphenyl)imidazo[1,5-a]pyrazin-3-yl)piperidine-1-carbonyl)-4,4-dimethylpent-2-enenitrile

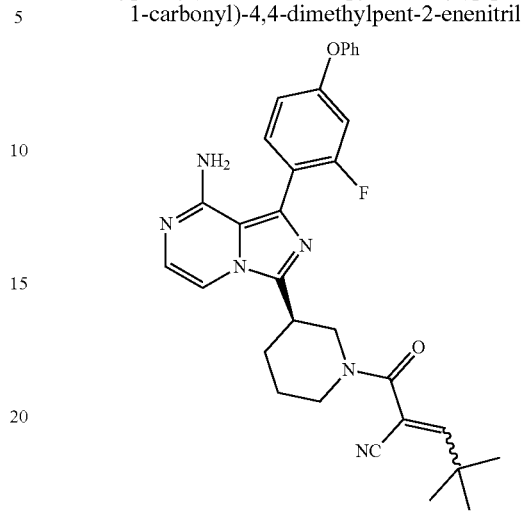

Into a 25-mL round-bottom flask, was placed 3-(2-fluoro-4-phenoxyphenyl)-1-[(3R)-piperidin-3-yl]imidazo[1,5-a]pyrazin-4-amine (800 mg, 1.98 mmol, 1.00 equiv), N,N-dimethylformamide (5 mL), 2-cyano-4,4-dimethylpent-2-enoic acid (365 mg, 2.38 mmol, 1.20 equiv), TEA (602 mg, 5.95 mmol, 3.00 equiv), and HATU (904 mg, 2.38 mmol, 1.20 equiv). The resulting solution was stirred for 1.5 h at rt. The reaction was then quenched by the addition of water, the resulting solution was extracted with of ethyl acetate and the organic layers combined. The resulting mixture was washed with saturated sodium chloride. The mixture was dried over anhydrous sodium sulfate and concentrated under vacuum. The crude material was purified by preparative chromatography to yield 109 mg of 2-[[(3R)-3-[4-amino-3-(2-fluoro-4-phenoxyphenyl)imidazo[1,5-a]pyrazin-1-yl]piperidin-1-yl]carbonyl]-4,4-dimethylpent-2-enenitrile as the trifluoroacetic acid salt. MS [M+H]⁺=539.1.

Example 19

Synthesis of (S)-2-(2-((8-amino-1-(2-fluoro-4-phenoxyphenyl)imidazo[1,5-a]pyrazin-3-yl)methyl)pyrrolidine-1-carbonyl)-4-methyl-4-(4-(oxetan-3-yl)piperazin-1-yl)pent-2-enenitrile

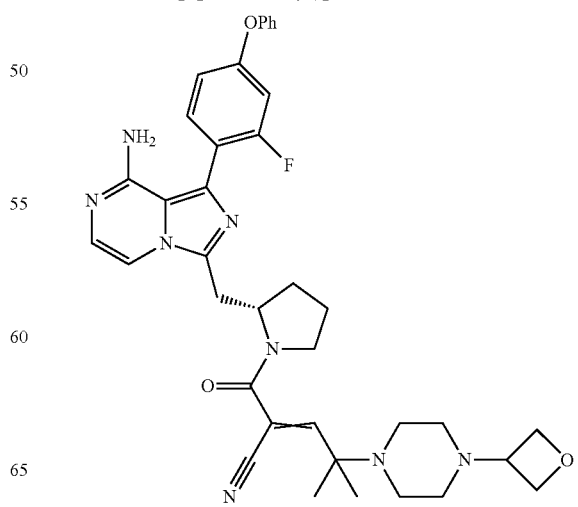

Step 1

To a mixture of 3-chloropyrazin-2-yl)methanamine (5 g, 35 mmol), (S)-2-(1-(tert-butoxycarbonyl)pyrrolidin-2-yl) acetic acid (8 g, 35 mmol) and HATU (13.3 g, 35 mmol) in DCM (80 mL) was added Et3N (10.6 g, 105 mmol), the mixture was stirred for 18 h at rt. The mixture was concentrated in vacuo and diluted with water before extracting with DCM. The combined organic layer was washed with brine, dried over anhydrous Na$_2$SO$_4$, filtered and concentrated. The residue was purified by silica gel chromatography to give 5.5 g of (S)-tert-butyl 2-(2-(((3-chloropyrazin-2-yl)methyl)amino)-2-oxoethyl)pyrrolidine-1-carboxylate which was used without further purification.

Step 2

To a solution of (S)-tert-butyl 2-(2-(((3-chloropyrazin-2-yl)methyl)amino)-2-oxoethyl)pyrrolidine-1-carboxylate (5.5 g, 15.5 mmol) in EtOAc (80 mL) was added POCl3 (16.5 g, 105 mmol) and DMF (4 mL) slowly at 0° C. and for 2 h at rt. The reaction was cooled in an ice bath and then a mixture of crushed ice and aq. NH4OH was added slowly. The resultant mixture was extracted with EtOAc, washed with brine, dried over anhydrous Na$_2$SO$_4$, filtered and concentrated. The residue was purified by silica gel chromatography to afford 3.5 g of (S)-tert-butyl 2-((8-chloroimidazo[1,5-a]pyrazin-3-yl)methyl)pyrrolidine-1-carboxylate.

Step 3

(S)-tert-butyl 2-((8-chloroimidazo[1,5-a]pyrazin-3-yl)methyl)pyrrolidine-1-carboxylate (3.5 g, 10.4 mmol) was dissolved in DMF (40 mL) and cooled to 0° C. NBS (2.4 g, 13.5 mmol) dissolved in 4 mL of DMF was added slowly and stirred for 1 h at rt. The reaction mixture was quenched with saturated NaHCO3 and extracted with EtOAc. The combined organic phase was washed with brine and dried over anhydrous Na$_2$SO$_4$, filtered and concentrated to give 3.5 g of (S)-tert-butyl 2-((1-bromo-8-chloroimidazo[1,5-a]pyrazin-3-yl)methyl)pyrrolidine-1-carboxylate which was used in the next step without further purification.

Step 4

(S)-tert-butyl 2-((1-bromo-8-chloroimidazo[1,5-a]pyrazin-3-yl)methyl)pyrrolidine-1-carboxylate (3.5 g, 8.45 mmol) dissolved in 30 mL of 7 M NH3/MeOH. The mixture was heated for 2 h at 120° C. The reaction was concentrated and then dissolved in EtOAc (50 mL) and washed with H$_2$O (40 mL). The aqueous layer was extracted with EtOAc (50 mL). The combined organic layers were washed with brine (60 mL), dried over anhydrous Na$_2$SO$_4$ and concentrated to afford 3 g of (S)-tert-butyl 2-((8-amino-1-bromoimidazo[1,5-a]pyrazin-3-yl)methyl)pyrrolidine-1-carboxylate which was used without further purification.

Step 5

To a flask were added (S)-tert-butyl 2-((8-amino-1-bromoimidazo[1,5-a]pyrazin-3-yl)methyl)pyrrolidine-1-carboxylate (3.0 g, 7.6 mmol), (2-fluoro-4-phenoxyphenyl) boronic acid (1.76 g, 7.6 mmol), Na$_2$CO$_3$ (1.61 g, 15.2 mmol) and PdCl$_2$dppf (556 mg, 0.76 mmol), then dioxane (50 mL) and water (10 mL) were added. The solution was stirred at 85° C. for 3 h. After cooling to rt, water was added and the mixture extracted with EtOAc. The combined organic layer was washed with water and then brine, dried over anhydrous Na$_2$SO$_4$, filtered and concentrated in vacuo to give a crude residue, which was purified by silica gel chromatography to afford 2.6 g of (S)-tert-butyl 2-((8-amino-1-(2-fluoro-4-phenoxyphenyl)imidazo[1,5-a]pyrazin-3-yl)methyl)pyrrolidine-1-carboxylate as a yellow oil.

Step 6

To a stirred solution of (S)-tert-butyl 2-((8-amino-1-(2-fluoro-4-phenoxyphenyl)imidazo[1,5-a]pyrazin-3-yl)methyl)pyrrolidine-1-carboxylate (2.6 g, 5.2 mmol) in DCM (4 mL) was added TFA (4 mL). The solution was stirred at rt for 2 h, concentrated in vacuo, then water was added. The mixture was extracted with EtOAc, and the aqueous layer was neutralized by aq. sodium bicarbonate to pH=10 and extracted with EtOAc and the combined organic layer was dried over anhydrous Na$_2$SO$_4$. The mixture was filtered and concentrated in vacuo to afford 2.2 g of (S)-1-(2-fluoro-4-phenoxyphenyl)-3-(pyrrolidin-2-ylmethyl)imidazo[1,5-a]pyrazin-8-amine as yellow oil which was used in the next step without further purification.

Step 7

To a solution of (S)-1-(2-fluoro-4-phenoxyphenyl)-3-(pyrrolidin-2-ylmethyl)imidazo[1,5-a]pyrazin-8-amine (1.5 g, 3.72 mmol), 2-cyanoacetic acid (380 mg, 4.47 mmol), HOBt (854 mg, 5.58 mmol), EDC (1.06 g, 5.58 mmol) in DMF (20 mL) was added DIPEA (1.44 g, 11.16 mmol). The mixture was stirred at rt for 2 h before eluting with EtOAc, the organic layer was washed with brine, dried over anhydrous Na$_2$SO$_4$, filtered and evaporated in vacuo to give 0.8 g of (S)-3-(2-((8-amino-1-(2-fluoro-4-phenoxyphenyl)imidazo[1,5-a]pyrazin-3-yl)methyl)pyrrolidin-1-yl)-3-oxopropanenitrile as a yellow solid which was used without further purification.

Step 8

To a solution of (S)-3-(2-((8-amino-1-(2-fluoro-4-phenoxyphenyl)imidazo[1,5-a]pyrazin-3-yl)methyl)pyrrolidin-1-yl)-3-oxopropanenitrile (200 mg, 0.426 mmol), 2-methyl-2-(4-(oxetan-3-yl)piperazin-1-yl)propanal (180 mg, 0.851 mmol) and pyrrolidine (125 mg, 1.75 mmol) in DCM (5 mL) at rt was slowly added chloro(trimethyl)silane (153 mg, 1.4 mmol) dropwise. 1 h later, the reaction was diluted with DCM and washed with aq. NaHCO$_3$. The organic layer was dried over anhydrous Na$_2$SO$_4$, filtered and concentrated to give a crude residue, which was purified by Prep-TLC to afford 100 g of (S)-2-(2-((8-amino-1-(2-fluoro-4-phenoxyphenyl)imidazo[1,5-a]pyrazin-3-yl)methyl)pyrrolidine-1-carbonyl)-4-methyl-4-(4-(oxetan-3-yl)piperazin-1-yl)pent-2-enenitrileas white solid. MS [M+H]$^+$=664.8.

Example 20

Synthesis of (R)-2-(3-(8-amino-1-(2-methyl-4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile

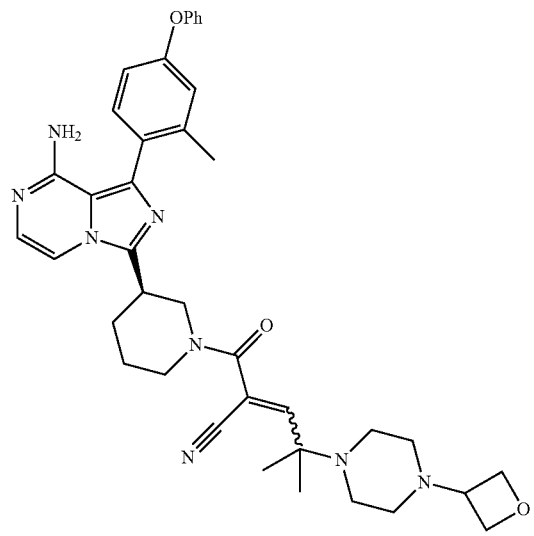 [SMILES: Cc1cc(Oc2ccccc2)ccc1-c1nc([C@@H]2CCCN(C(=O)C(C#N)=CC(C)(C)N3CCN(C4COC4)CC3)C2)n2ccnc(N)c12]

Step 1

A solution of 4-fluoro-2-methyl-1-nitrobenzene 2-methyl-1-nitro-4-phenoxybenzene (27.3 g, 290 mmol), phenol (43.4 g, 280 mmol) and K$_2$CO$_3$ (80 g, 580 mmol) in DMF (300 mL) was heated at 80° C. for 18 h. The mixture was cooled. Water (2000 mL) was added and washed with petroleum ether. The combined organic layer was washed sequentially with 5% NaOH and water, dried over Na$_2$SO$_4$. The solvent was concentrated to afford 2-methyl-1-nitro-4-phenoxybenzene (63 g, 98%) as a yellow oil which was used without further purification.

Step 2

A solution of 2-methyl-1-nitro-4-phenoxybenzene (63 g, 275 mmol) in MeOH (500 mL) was added Pd/C (10 g). The mixture was stirred under H2 atmosphere (1 atm) for 18 h. The mixture was filtered and concentrated to afford 2-methyl-4-phenoxyaniline (51 g, 93%) as a brown solid which was used in the next step without purification.

Step 3

A suspension of 2-methyl-4-phenoxyaniline (19 g, 95.5 mmol) in water (375 mL) was added HBr (150 mL, 40%) at 0° C. After 30 min, NaNO$_2$ (6.9 g, 100 mmol) in water (75 mL) was added at 0° C. After 30 min, the mixture was added to a pre-heated suspension of CuBr (14.3 g, 100 mmol) in water (375 mL) at 65° C. The mixture was stirred at 65° C. for 30 min, cooled, and extracted with petroleum ether. The combined organic layer was washed with water and dried over Na$_2$SO$_4$. Purification by silica gel column chromatography afforded 1-bromo-2-methyl-4-phenoxybenzene (15 g, 60%) as a yellow oil.

Step 4

A mixture of 1-bromo-2-methyl-4-phenoxybenzene (15 g, 57 mmol), 4,4,4',4',5,5,5',5'-octamethyl-2,2'-bi(1,3,2-dioxaborolane) (16 g, 63 mmol), Pd(dppf)2Cl2 (2 g, 2.85 mmol) and potassium acetate (16.7 g, 170 mmol) in DMF (170 mL) was heated to 80° C. for 18 h. The mixture was cooled and concentrated. Purification by silica gel column chromatography afforded 4,4,5,5-tetramethyl-2-(2-methyl-4-phenoxyphenyl)-1,3,2-dioxaborolane (10 g, 57%) as a colourless oil.

Step 5

A solution of 4,4,5,5-tetramethyl-2-(2-methyl-4-phenoxyphenyl)-1,3,2-dioxaborolane (186 mg, 0.6 mmol), (R)-3-(3-(4-amino-3-iodo-1H-pyrazolo[4,3-c]pyridin-1-yl)piperidin-1-yl)-3-oxopropanenitrile (164 mg, 0.4 mmol), Pd(dppf)$_2$Cl$_2$ (15 mg, 0.02 mmol) and Na2CO3 (85 mg, 0.8 mmol) in Dioxane/H2O (3 mL, v/v=3:1) was stirred at 80° C. for 18 h. After cooling to rt, the reaction was concentrated in vacuo and purified by silica gel chromatography to afford (R)-3-(3-(4-amino-3-(2-methyl-4-phenoxyphenyl)-1H-pyrazolo[4,3-c]pyridin-1-yl)piperidin-1-yl)-3-oxopropanenitrile (115 mg, 62%) as a yellow foam.

Step 6

A solution of (R)-3-(3-(4-amino-3-(2-methyl-4-phenoxyphenyl)-1H-pyrazolo[4,3-c]pyridin-1-yl)piperidin-1-yl)-3-oxopropanenitrile (115 mg, 0.25 mmol), 2-methyl-2-(4-(oxetan-3-yl)piperazin-1-yl)propanal (104 mg, 0.49 mmol), pyrrolidine (0.5 mL) and TMSCl (0.2 mL) in DCM (2 mL) was stirred at rt for 1 h, then concentrated in vacuo and purified by silica gel column chromatography (DCM/MeOH=20:1) to afford 2-((3R)-3-(4-amino-3-(2-methyl-4-phenoxyphenyl)-1H-pyrazolo[4,3-c]pyridin-1-yl)cyclohexanecarbonyl)-4-methyl-4-(4-(oxetan-3-yl)piperazin-1-yl)pent-2-enenitrile (50 mg, 30%) as a white solid. MS [M+H]$^+$=661.0.

BIOLOGICAL EXAMPLES

Example 1

BTK Enzymatic Activity Assay

A Caliper-based kinase assay (Caliper Life Sciences, Hopkinton, Mass.) was used to measure inhibition of BTK kinase activity of a compound of the present disclosure. Serial dilutions of test compounds were incubated with human recombinant BTK (0.5 nM), ATP (16 µM) and a phosphoacceptor peptide substrate FAM-GEEP-LYWSFPAKKK-NH$_2$ (1 µM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated. This value is presented as the IC$_{50}$. The IC$_{50}$ for certain compounds of the disclosure are provided below.

| Compound No. in Compound Table I | IC$_{50}$ (nM) |
|---|---|
| 1 | 1.4 |
| 2 | 1.9 |
| 7 | 0.8 |
| 8 | 0.3 |
| 9 | 8.6 |
| 10 | 1.9 |
| 11 | 2.0 |
| 12 | 14 |
| 13 | 7.4 |
| 15 | 22.4 |
| 16 | 1.7 |
| 17 | 2.9 |
| 18 | 4.3 |
| 19 | 23.5 |
| 20 | 19.1 |
| 21 | 18.6 |
| 22 | 2.5 |
| 23 | 1.6 |
| 24 | 1.7 |
| 25 | 4.4 |
| 26 | 3.0 |
| 27 | 1.3 |
| 28 | 0.9 |
| 29 | 0.8 |
| 30 | 2.2 |
| 31 | 11.5 |
| 32 | 8.9 |
| 33 | 45.7 |
| 34 | 1.9 |
| 35 | 2.1 |
| 39 | 1.3 |
| 40 | 2.4 |
| 41 | 2.4 |
| 42 | 2.6 |
| 43 | 2.0 |
| 44 | 2.2 |
| 45 | 4.6 |
| 46 | 2.1 |
| 47 | 4.1 |
| 48 | 3.1 |
| 49 | 1.8 |
| 50 | 4.2 |
| 51 | 2.6 |
| 52 | 1.8 |
| 53 | 2.0 |
| 54 | 1.7 |
| 55 | 2.4 |
| 56 | 1.2 |
| 57 | 1.1 |
| 58 | 2.8 |
| 59 | 1.4 |
| 62 | 2.2 |
| 63 | 0.9 |
| 64 | 0.8 |
| 65 | 0.6 |
| 66 | 0.3 |
| 67 | 0.2 |
| 72 | 2.0 |

Example 2

Measurement of BTK Engagement in Human Ramos B Cell Line

The potency of compounds for inhibition of BTK activity can be assessed by binding of compounds to the target in human Ramos B cells that contain BTK. The extent of BTK occupancy is measured after treating the cells with compounds and detecting unoccupied BTK through binding of N-(2-(4-((E)-4-((R)-3-(4-amino-3-(4-phenoxyphenyl)-1H-pyrazolo[3,4-d]pyrimidin-1-yl)piperidin-1-yl)-4-oxobut-2-en-1-yl)piperazin-1-yl)ethyl)-6-(6-(5-(2-oxohexahydro-1H-thieno[3,4-d]imidazol-4-yl)pentanamido)hexanamido) hexanamide as the probe.

Briefly, Ramos cells are added to 96 well plates at a density of $10^6$ cells per well. Serial dilutions of the compounds to be tested for potency are added such the final concentrations started at 1 μM and were serially diluted 3 fold for a total of 8 serial dilutions. The final DMSO concentration is 0.09% in each well. The compounds are allowed to interact with the cells for 1 hr. A BTK selective probe is then added to each well for a final concentration of 330 nM. Treatment with the probe is for 1 hr. The cells are then collected by centrifugation and lysed for 15-30 minutes on ice. The binding of the probe to BTK is then detected by Alphascreen (Perkin Elmer) using a kit for the specific label on the BTK probe. The percent occupancy of BTK at each compound concentration is then calculated based on detection of unoccupied BTK bound by the labeled probe. BTK occupancy is then plotted as a function of the log of the compound concentration and the $IC_{50}$ values are calculated. The assay to measure BTK occupancy is modified to measure the durability of BTK binding in cells by removing the compound from the culture medium and incubating the cells for varying time periods followed by measurement of remaining occupancy as described above.

Example 3

Blockade of CD69 Expression in Human Whole Blood Samples

Activation of the B cell receptor leads to increased BTK activity, calcium mobilization and B cell activation (see Honigberg L. A., et. al., Proc Natl Acad Sci USA. 107: 13075-80. 2010). BTK inhibitors have been shown to block B cell activation as measured by CD69 expression (see Karp, R., et. al., Inhibition of BTK with AVL-292 Translates to Protective Activity in Animal Models of Rheumatoid Arthritis. Inflammation Research Association Meeting, September, 2010). CD69 was expressed following B cell activation as a measure of BTK activity in whole blood. Aliquots of whole blood were pre-incubated with serial dilutions of test compound for 30 minutes followed by activation with anti-IgM (goat Fab' 2, 50 μg/ml). Samples were incubated overnight at 37° C. and then stained with PE labeled anti-CD20 and APC labeled anti-CD69 (BD Pharmingen) for 30 minutes according to the manufacturer's directions. Whole blood was then lysed and cells gated on CD20 expression were quantified for CD 69 expression by FACS. The percent inhibition was calculated based on a DMSO control for no inhibition and plotted as a function of test compound concentration from which an $IC_{50}$ value was calculated. The $IC_{50}$ for certain compounds of the disclosure are provided below.

| Compound # in Compound Table I | $IC_{50}$ (μm) |
|---|---|
| 1 | 0.1088 |
| 7 | 0.1139 |
| 9 | 0.5263 |
| 10 | 0.289 |
| 11 | 0.2003 |
| 12 | 0.8741 |
| 13 | 1.2948 |
| 14 | 0.1807 |
| 16 | 0.9307 |
| 17 | 0.1651 |
| 18 | 0.1297 |
| 19 | 0.1778 |
| 22 | 0.5112 |
| 23 | 0.538 |
| 24 | 0.5772 |
| 25 | 0.4301 |
| 26 | 0.3672 |

Example 4

Inhibition of Mouse Collagen-Induced Arthritis

Inhibition of murine collagen-induced arthritis (mCIA) is a standard animal disease model for rheumatoid arthritis. Previous studies have demonstrated that inhibition of BTK is efficacious in blocking mCIA (see Honigberg L. A., et. al., Proc Natl Acad Sci USA. 107:13075-80. 2010). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by Elisa at the end of the study (Bolder BioPath, Boulder, Colo.).

Example 5

Recovery of Kinase Activity Upon Dialysis to Evaluate Irreversible Vs. Reversible Covalent Binding A compound and/or pharmaceutically acceptable salt of the present disclosure at a concentration 10 times greater than its $IC_{50}$ value is added to a solution of protein kinase (5 nM) in a buffer containing 20 mM Hepes [pH 7.5], 5 mM $MgCl_2$, 0.01% Triton X-100, and 1 mM dithiothreitol. After 60 min at 22° C., the reactions are transferred to a dialysis cassette (0.1-0.5 mL Slide-A-Lyzer, MWCO 10 kDa, Pierce) and dialyzed against 1 L of buffer (20 mM Hepes [pH 7.5], 5 mM $MgCl_2$, 0.01% Triton X-100, and 1 mM dithiothreitol.) at 22° C. The dialysis buffer is exchanged twice per day until the end of the experiment. Aliquots are removed from the dialysis cassettes every 24 h and analyzed for protein kinase activity. Kinase activity for each sample was normalized to the DMSO control for that time point and expressed as the mean±SD.

Example 6

Mass Spectral Analysis

A protein kinase that is inhibited by compound of Formula (I) and/or a pharmaceutically acceptable salt of the present disclosure may be subjected to mass spectral analysis to assess the formation of permanent, irreversible covalent adducts. Suitable analytical methods to examine intact full protein or peptide fragments generated upon tryptic cleavage of the protein kinase are generally known in the art. Such methods identify permanent, irreversible covalent protein adducts by observing a mass peak that corresponds to the mass of a control sample plus the mass of an irreversible adduct. Two such methods are described below.

Mass Spectral Analysis of Intact Full Kinase
Method:

A protein kinase (5 µM) is incubated with a compound of the present disclosure (25 µM, 5 equiv) for 1 h at room temperature in buffer (20 mM Hepes [pH 8.0], 100 mM NaCl, 10 mM MgCl2). A control sample is also prepared which does not have a compound of the present disclosure. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software.

Results: High-resolution intact mass spectrometry analysis of a kinase that is inhibited by a compound of the present disclosure will reveal a spectrum similar to the kinase in the absence of inhibitor (e.g. control sample). There will be no formation of a new peak in the mass spectrum corresponding to the molecular mass of the kinase plus the molecular mass of the compound of Formula I. On the basis of this experiment, as can be applied to a compound and/or pharmaceutically acceptable salt as disclosed herein, no permanent, irreversible protein adduct will be apparent to one skilled in the art.

Mass Spectral Analysis of Kinase Tryptic Digest
Method:

A protein (10-100 pmols) is incubated with a compound and/or pharmaceutically acceptable salt of the present disclosure (100-1000 pmols, 10 equiv) for 3 h prior to tryptic digestion. Iodoacetamide may be used as the alkylating agent after compound incubation. A control sample is also prepared which does not utilize the compound and/or pharmaceutically acceptable salt of the present disclosure. For tryptic digests a 1 µl aliquot (3.3 pmols) ise diluted with 10 µl of 0.1% TFA prior to micro C18 Zip Tipping directly onto the MALDI target using alpha cyano-4-hydroxy cinnamic acid as the desorption matrix (5 mg/mol in 0.1% TFA:Acetonitrile 50:50) or Sinapinic acid as the desorption matrix (10 mg/mol in 0.1% TFA:Acetonitrile 50:50).

Results: High-resolution mass spectrometry analysis of the tryptic fragments of a kinase that is inhibited by a compound and/or pharmaceutically acceptable salt of the present disclosure will reveal a spectrum similar to the kinase in the absence of inhibitor (e.g. control sample). There will be no evidence of any modified peptides that are not present in the control sample. On the basis of this experiment, no permanent, irreversible protein adducts will be apparent to one skilled in the art.

Cellular assays are also optionally used to assess the inhibiting properties of a compound of the present disclosure. Cellular assays include cells from any appropriate source, including plant and animal cells (such as mammalian cells). The cellular assays are also optionally conducted in human cells. Cellular assays of BTK inhibition are well known in the art, and include methods in which an inhibitor is delivered into the cell (e.g. by electroporation, passive diffusion, microinjection and the like) and an activity endpoint is measured, such as the amount of phosphorylation of a cellular substrate, the amount of expression of a cellular protein, or some other change in the cellular phenotype known to be affected by the catalytic activity of BTK. For example, phosphorylation of a particular cellular substrate is optionally assessed using a detection antibody specific or the phosphorylated cellular substrate followed by western blotting techniques and visualization using any appropriate means (e.g. fluorescent detection of a fluorescently labeled antibody).

Measuring the reduction in the BTK catalytic activity in the presence of the present disclosure relative to the activity in the absence of the present disclosure is optionally performed using a variety of methods known in the art, such as the assays described in the Examples section below. Other methods for assaying BTK activity are known in the art.

Example 7

Determination of Drug-Kinase Residence Time

The following is a protocol that can be used to distinguish whether a compound displays a slow or non-existent dissociation rate from BTK, such as typically would occur if a covalent bond is formed between the compound and the target. The read-out for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM $MgCl_2$, 0.01% Triton X-100, and 1 mM EGTA.

The first step of the procedure was incubation of 500 nM BTK (Invitrogen Cat. #PV3587) with 1.5 µM of a compound of the present disclosure for 30 minutes in a volume of 10 µL. The mixture was then diluted 5-fold by addition of 40 µL of buffer. A 10 µL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For BTK, the competition solution contained 1.5 µM Tracer 178 (Invitrogen Cat. #PV5593), which is a proprietary high affinity ligand for BTK coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in BTK.

After addition of 10 µL of the competition solution to the Greiner plate, the mixture was incubated for one hour or greater to allow time for dissociation of non-covalent inhibitors and binding of the high affinity tracer. It is to be expected that covalent and slow dissociating inhibitors will block binding of the tracer while rapidly dissociating non-covalent inhibitors will not Binding of the tracer to BTK is detected using TR-FRET between the Europium moiety of the Anti-histidine antibody and the AlexaFluor 647 group of Tracer 178. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of BTK from the reaction, If the compound is an irreversible covalent inhibitor, tracer will be completely blocked from binding to the target throughout the entire course of the experiment.

Example 8

Reversibility of Binding

The following approach was developed to differentiate compounds that form irreversible covalent bond with their targets, such as non-cyano containing acrylamide compounds, from compound that form reversible covalent bond i.e., compounds and/or pharmaceutically acceptable salts of the present disclosure. Reactions are prepared with the protein target at a higher concentration than the compounds of interest. Both irreversible and reversible covalent compounds bind the target and became depleted from solution. The reactions are then treated with perturbations including both denaturation with 5 M guanidine hydrochloride and digestion with trypsin, disrupting proper folding of the target. It is found that the perturbation returned reversible covalent compounds to solution due to dissociation from the target while irreversible covalent compounds remained bound to the target. The concentration of compound in solution is assessed both preceding and following perturbation using high performance liquid chromatography (HPLC) coupled to tandem mass spectrometry. Using this technique, it can be demonstrated that irreversible covalent compound is depleted from solution in both the native and perturbed state, while compounds and/or pharmaceutically acceptable salts disclosed herein are depleted in the folded state but returned to solution following perturbation of the target evidencing that compounds and/or pharmaceutically acceptable salts disclosed herein form reversible covalent bond.

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
| --- | --- |
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
| --- | --- |
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL The foregoing disclosure has been described in some detail by way of illustration and example, for purposes of clarity and understanding. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed:

1. A compound chosen from:

| Name | Structure |
| --- | --- |
| (R)-2-(3-(8-amino-1-(2-fluoro-4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile; | 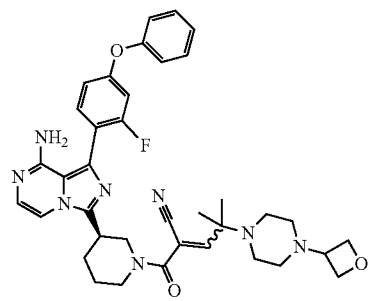 [SMILES: CC(C)(C=C(C#N)C(=O)N1CCC[C@@H](c2nc(-c3ccc(Oc4ccccc4)cc3F)c3c(N)nccn23)C1)N1CCN(C2COC2)CC1] |
| (S)-2-(2-((8-amino-1-(2-fluoro-4-phenoxyphenyl)imidazo[1,5-a]pyrazin-3-yl)methyl)pyrrolidine-1-carbonyl)-4,4-dimethylpent-2-enenitrile; | 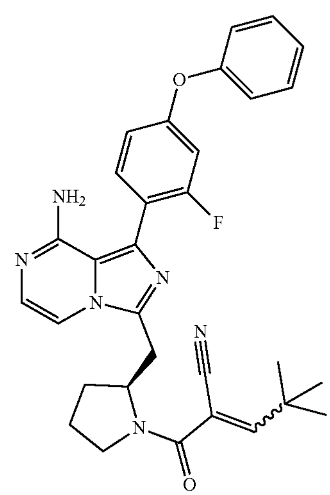 [SMILES: CC(C)(C)C=C(C#N)C(=O)N1CCC[C@H]1Cc1nc(-c2ccc(Oc3ccccc3)cc2F)c2c(N)nccn12] |
| (S)-2-(2-((8-amino-1-(2-fluoro-4-phenoxyphenyl)imidazo[1,5-a]pyrazin-3-yl)methyl)pyrrolidine-1-carbonyl)-4-methyl-4-morpholinopent-2-enenitrile; | 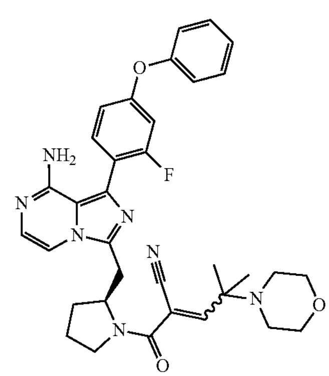 [SMILES: CC(C)(C=C(C#N)C(=O)N1CCC[C@H]1Cc1nc(-c2ccc(Oc3ccccc3)cc2F)c2c(N)nccn12)N1CCOCC1] |

| Name | Structure |
|---|---|
| (S)-2-(2-((8-amino-1-(2-fluoro-4-phenoxyphenyl)imidazo[1,5-a]pyrazin-3-yl)methyl)pyrrolidine-1-carbonyl)-4-methyl-4-(methyl(oxetan-3-yl)amino)pent-2-enenitrile; | 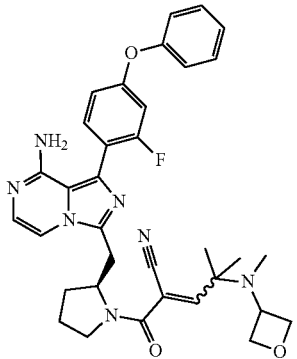 [SMILES: CN(C1COC1)C(C)(C)C=C(C#N)C(=O)N1CCC[C@H]1Cc1nc(-c2ccc(Oc3ccccc3)cc2F)c2c(N)nccn12] |
| (S)-2-(2-((8-amino-1-(2-fluoro-4-phenoxyphenyl)imidazo[1,5-a]pyrazin-3-yl)methyl)pyrrolidine-1-carbonyl)-4-methyl-4-(4-(oxetan-3-yl)piperazin-1-yl)pent-2-enenitrile; and | 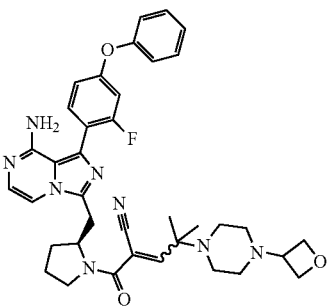 [SMILES: CC(C)(C=C(C#N)C(=O)N1CCC[C@H]1Cc1nc(-c2ccc(Oc3ccccc3)cc2F)c2c(N)nccn12)N1CCN(C2COC2)CC1] |
| (R)-2-(3-(8-amino-1-(4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile, | 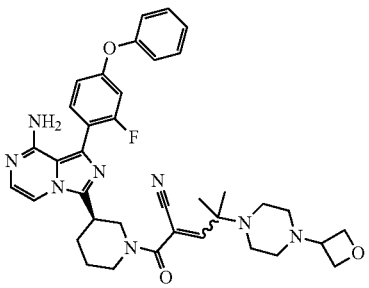 [SMILES: CC(C)(C=C(C#N)C(=O)N1CCC[C@@H](c2nc(-c3ccc(Oc4ccccc4)cc3F)c3c(N)nccn23)C1)N1CCN(C2COC2)CC1] | or a stereoisomer of any of the above compounds, or an E or Z isomer thereof, or a pharmaceutically acceptable salt of any of the above compounds.

2. The compound of claim 1 chosen from:

| Name | Structure |
|---|---|
| (R)-2-(3-(8-amino-1-(2-fluoro-4-phenoxyphenyl)imidazo[1,5-a]pyrazin-3-yl)piperidine-1-carbonyl)-4-methyl-4-(4-(oxetan-3-yl)piperazin-1-yl)pent-2-enenitrile; | 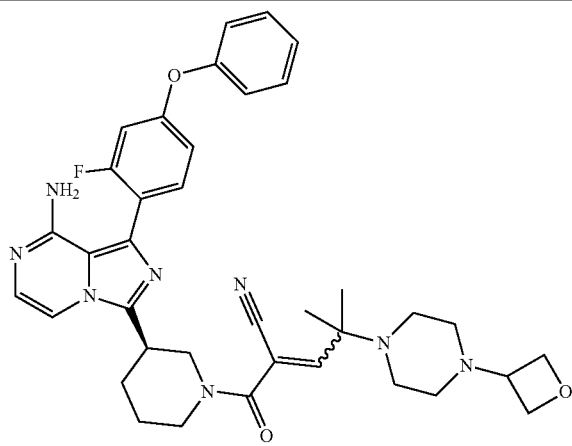 | or a stereoisomer,
or an E or Z isomer thereof,
or a pharmaceutically acceptable salt thereof.

3. A pharmaceutical composition comprising:
a compound of claim 1 or a pharmaceutically acceptable salt thereof; and
a pharmaceutically acceptable excipient.

4. A pharmaceutical composition comprising:
a compound of claim 2 or a pharmaceutically acceptable salt thereof; and
a pharmaceutically acceptable excipient.

* * * * *